(12) United States Patent
Siddiqui-Jain et al.

(10) Patent No.: US 12,338,261 B2
(45) Date of Patent: *Jun. 24, 2025

(54) ALVOCIDIB PRODRUGS HAVING INCREASED BIOAVAILABILITY

(71) Applicant: SUMITOMO PHARMA ONCOLOGY, INC., Marlborough, MA (US)

(72) Inventors: Adam Siddiqui-Jain, South Jordan, UT (US); David J. Bearss, Alpine, UT (US)

(73) Assignee: Sumitomo Pharma Oncology, Inc., Marlborough, MA (US)

( * ) Notice: Subject to any disclaimer, the term of this patent is extended or adjusted under 35 U.S.C. 154(b) by 372 days.

This patent is subject to a terminal disclaimer.

(21) Appl. No.: 17/314,896

(22) Filed: May 7, 2021

(65) Prior Publication Data
US 2021/0261585 A1 Aug. 26, 2021

Related U.S. Application Data

(60) Continuation of application No. 16/727,693, filed on Dec. 26, 2019, now abandoned, which is a continuation of application No. 16/279,958, filed on Feb. 19, 2019, now Pat. No. 10,562,925, which is a division of application No. 15/673,213, filed on Aug. 9, 2017, now Pat. No. 10,259,835, which is a division of application No. 15/158,206, filed on May 18, 2016, now Pat. No. 9,758,539.

(60) Provisional application No. 62/163,188, filed on May 18, 2015.

(51) Int. Cl.
| | |
|---|---|
| C07F 9/6558 | (2006.01) |
| A61K 31/38 | (2006.01) |
| A61P 35/02 | (2006.01) |
| C07D 311/22 | (2006.01) |
| C07D 311/30 | (2006.01) |
| C07D 405/04 | (2006.01) |

(52) U.S. Cl.
CPC .......... *C07F 9/65586* (2013.01); *A61K 31/38* (2013.01); *A61P 35/02* (2018.01); *C07D 311/22* (2013.01); *C07D 311/30* (2013.01); *C07D 405/04* (2013.01)

(58) Field of Classification Search
CPC ............................ A61K 31/675; A61K 9/2054
See application file for complete search history.

(56) References Cited

U.S. PATENT DOCUMENTS

| | | | |
|---|---|---|---|
| 4,132,710 A | 1/1979 | Gauthier |
| 4,146,629 A | 3/1979 | Kubela et al. |
| 4,522,811 A | 6/1985 | Eppstein et al. |
| 4,676,980 A | 6/1987 | Segal et al. |
| 4,816,567 A | 3/1989 | Cabilly et al. |
| 4,900,727 A | 2/1990 | Kattige et al. |
| 4,946,778 A | 8/1990 | Ladner et al. |
| 4,971,909 A | 11/1990 | Kaneoya et al. |
| 5,225,539 A | 7/1993 | Winter |
| 5,284,856 A | 2/1994 | Naik et al. |
| 5,310,763 A | 5/1994 | Campion et al. |
| 5,545,806 A | 8/1996 | Lonberg et al. |
| 5,545,807 A | 8/1996 | Surani et al. |
| 5,569,825 A | 10/1996 | Lonberg et al. |
| 5,587,458 A | 12/1996 | King et al. |
| 5,625,126 A | 4/1997 | Lonberg et al. |
| 5,633,425 A | 5/1997 | Lonberg et al. |

(Continued)

FOREIGN PATENT DOCUMENTS

| | | |
|---|---|---|
| CN | 1583776 A | 2/2005 |
| EP | 0137193 A2 | 4/1985 |

(Continued)

OTHER PUBLICATIONS

Adlard et al., "Prediction of the response of colorectal cancer to systemic therapy," *The Lancet Oncology* 3:75-82 (2002).

Ait-Ikhlef et al., "The motoneuron degeneration in the wobbler mouse is independent of the overexpression of a Bc12 transgene in neurons," *Neurosci Lett* 199:163-166 (1995).

Akgul, C., "Mcl-1 is a Potential Therapeutic Target in Multiple Types of Cancer", Cell. Mol. Life Sci., 66:1326-1336 (2009).

Almarzooqi et al., "Comparison of Peripheral Blood versus Bone Marrow Blasts Immunophenotype in Pediatric Acute Leukemias," *Ibnosina Journal of Medicine and Biomedical Sciences*, pp. 195-204 (2011). (10 pages).

(Continued)

*Primary Examiner* — Kevin E Weddington
(74) *Attorney, Agent, or Firm* — Hamilton, Brook, Smith & Reynolds, P.C.

(57) ABSTRACT

Compounds having the following structure (I):

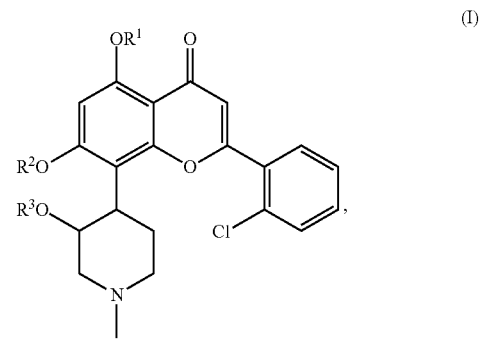

or a stereoisomer, tautomer or pharmaceutically acceptable salt thereof, wherein one of $R^1$, $R^2$ or $R^3$ is —P(=O)(OH)$_2$, and the other two of $R^1$, $R^2$ and $R^3$ are each H, are provided. Pharmaceutical compositions comprising the compounds, and methods for use of the compounds for treating diseases associated with overexpression of a cyclin-dependent kinase (CDK) are also provided.

10 Claims, 13 Drawing Sheets

(56) References Cited

U.S. PATENT DOCUMENTS

| | | |
|---|---|---|
| 5,661,016 A | 8/1997 | Lonberg et al. |
| 5,674,980 A | 10/1997 | Frankel et al. |
| 5,747,498 A | 5/1998 | Schnur et al. |
| 5,792,783 A | 8/1998 | Tang et al. |
| 5,804,604 A | 9/1998 | Frankel et al. |
| 5,834,504 A | 11/1998 | Tang et al. |
| 5,849,733 A | 12/1998 | Kim |
| 5,861,510 A | 1/1999 | Piscopio et al. |
| 5,863,949 A | 1/1999 | Robinson et al. |
| 5,877,305 A | 3/1999 | Huston et al. |
| 5,883,113 A | 3/1999 | Tang et al. |
| 5,886,020 A | 3/1999 | Tang et al. |
| 5,908,934 A | 6/1999 | Kim |
| 5,916,771 A | 6/1999 | Hori et al. |
| 5,932,595 A | 8/1999 | Bender et al. |
| 5,939,598 A | 8/1999 | Kucherlapati et al. |
| 5,965,703 A | 10/1999 | Horne et al. |
| 6,077,864 A | 6/2000 | Burgess et al. |
| 6,087,366 A | 7/2000 | Park et al. |
| 6,087,392 A | 7/2000 | Reiter |
| 6,090,852 A | 7/2000 | Dack et al. |
| 6,110,964 A | 8/2000 | Robinson |
| 6,136,981 A | 10/2000 | Brion et al. |
| 6,147,061 A | 11/2000 | Reiter |
| 6,153,609 A | 11/2000 | Robinson et al. |
| 6,177,401 B1 | 1/2001 | Ullrich et al. |
| 6,207,669 B1 | 3/2001 | Cockerill et al. |
| 6,214,872 B1 | 4/2001 | Robinson |
| 6,225,473 B1 | 5/2001 | Breipohl et al. |
| 6,258,540 B1 | 7/2001 | Lo et al. |
| 6,284,764 B1 | 9/2001 | Kath et al. |
| 6,291,455 B1 | 9/2001 | Thomas et al. |
| 6,294,532 B1 | 9/2001 | Thomas et al. |
| 6,303,636 B1 | 10/2001 | Robinson, Jr. et al. |
| 6,362,336 B1 | 3/2002 | Lohmann et al. |
| 6,399,633 B1 | 6/2002 | Dumont et al. |
| 6,406,912 B1 | 6/2002 | Holla |
| 6,437,136 B2 | 8/2002 | Breiphol et al. |
| 6,492,383 B1 | 12/2002 | Munchhof et al. |
| 6,495,568 B1 | 12/2002 | Dack et al. |
| 6,511,993 B1 | 1/2003 | Dack et al. |
| 6,576,647 B2 | 6/2003 | Bafus et al. |
| 6,596,726 B1 | 7/2003 | Bridges et al. |
| 6,599,890 B1 | 7/2003 | McClure et al. |
| 6,723,726 B1 | 4/2004 | Cockerill et al. |
| 6,821,990 B2 | 11/2004 | Kesseler |
| 6,828,320 B2 | 12/2004 | Cockerill et al. |
| 6,849,631 B2 | 2/2005 | Carini |
| 7,064,193 B1 | 6/2006 | Cory et al. |
| 7,119,090 B2 | 10/2006 | Tang et al. |
| 7,332,582 B2 | 2/2008 | Hardy et al. |
| 7,417,055 B2 | 8/2008 | Cannizzaro |
| 7,452,901 B2 | 11/2008 | Boojamra et al. |
| 7,488,802 B2 | 2/2009 | Collins et al. |
| 7,572,924 B2 | 8/2009 | Tang et al. |
| 7,695,715 B2 | 4/2010 | Hardy et al. |
| 7,714,005 B2 | 5/2010 | Chen et al. |
| 7,790,902 B2 | 9/2010 | Larson et al. |
| 7,816,398 B2 | 10/2010 | Swindell et al. |
| 7,829,662 B2 | 11/2010 | Korsmeyer et al. |
| 7,868,133 B2 | 1/2011 | Korsmeyer et al. |
| 7,884,127 B2 | 2/2011 | Lal et al. |
| 7,943,743 B2 | 5/2011 | Korman et al. |
| 8,008,449 B2 | 8/2011 | Korman et al. |
| 8,168,179 B2 | 5/2012 | Honjo et al. |
| 8,168,755 B2 | 5/2012 | Cardone et al. |
| 8,217,149 B2 | 7/2012 | Irving et al. |
| 8,221,966 B2 | 7/2012 | Letai |
| 8,304,449 B2 | 11/2012 | Lal et al. |
| 8,354,509 B2 | 1/2013 | Craven et al. |
| 8,372,819 B2 | 2/2013 | Jones et al. |
| 8,460,927 B2 | 6/2013 | Chen |
| 8,552,154 B2 | 10/2013 | Freeman et al. |
| 8,552,156 B2 | 10/2013 | Takayanagi et al. |
| 8,686,119 B2 | 4/2014 | Roten-Yehudar et al. |
| 8,735,553 B1 | 5/2014 | Li et al. |
| 8,758,752 B2 | 6/2014 | Govindan et al. |
| 8,779,108 B2 | 7/2014 | Queva et al. |
| 8,822,526 B2 | 9/2014 | Rathos et al. |
| 8,841,418 B2 | 9/2014 | Karsunky et al. |
| 8,907,053 B2 | 12/2014 | Sasikumar et al. |
| 8,927,697 B2 | 1/2015 | Davis et al. |
| 8,975,239 B2 | 3/2015 | Green et al. |
| 8,993,731 B2 | 3/2015 | Tyson |
| 9,102,727 B2 | 8/2015 | Freeman et al. |
| 9,138,485 B2 | 9/2015 | Govindan et al. |
| 9,163,087 B2 | 10/2015 | Kuchroo et al. |
| 9,175,082 B2 | 11/2015 | Zhou et al. |
| 9,199,973 B2 | 12/2015 | Carter et al. |
| 9,205,148 B2 | 12/2015 | Langermann et al. |
| 9,241,941 B2 | 1/2016 | Wendal et al. |
| 9,244,059 B2 | 1/2016 | Triebel et al. |
| 9,340,524 B2 | 5/2016 | Chen et al. |
| 9,360,473 B2 | 6/2016 | Cardone |
| 9,493,454 B2 | 11/2016 | Zeng et al. |
| 9,505,839 B2 | 11/2016 | Lonberg et al. |
| 9,540,674 B2 | 1/2017 | Letai |
| 9,605,070 B2 | 3/2017 | Seabatos-Peyton et al. |
| 9,683,048 B2 | 6/2017 | Freeman et al. |
| 9,758,539 B2 | 9/2017 | Siddiqui-Jain et al. |
| 9,856,303 B2 | 2/2018 | Korsmeyer et al. |
| 9,901,574 B2 | 2/2018 | Warner et al. |
| 9,902,759 B2 | 2/2018 | Korsmeyer et al. |
| 9,925,192 B2 | 3/2018 | Strack et al. |
| 9,988,452 B2 | 6/2018 | Freeman et al. |
| 10,132,797 B2 | 11/2018 | Bearss et al. |
| 10,259,835 B2 | 4/2019 | Siddiqui-Jain et al. |
| 10,267,787 B2 | 4/2019 | Bearss et al. |
| 10,357,488 B2 | 7/2019 | Warner et al. |
| 10,422,788 B2 | 9/2019 | Bearss et al. |
| 10,562,925 B2 * | 2/2020 | Siddiqui-Jain ........ A61P 43/00 |
| 10,568,887 B2 | 2/2020 | Bearss et al. |
| 10,624,880 B2 | 4/2020 | Warner et al. |
| 10,682,356 B2 | 6/2020 | Bearss et al. |
| 10,793,915 B2 | 10/2020 | Dettman et al. |
| 10,835,537 B2 | 11/2020 | Bearss et al. |
| 11,034,710 B2 | 6/2021 | Siddiqui-Jain et al. |
| 11,279,694 B2 * | 3/2022 | Siddiqui-Jain ...... C07F 9/65586 |
| 11,497,756 B2 | 11/2022 | Bearss et al. |
| 11,530,231 B2 * | 12/2022 | Siddiqui-Jain ....... A61K 9/2054 |
| 11,793,802 B2 | 10/2023 | Bearss et al. |
| 2001/0021704 A1 | 9/2001 | Ghyczy et al. |
| 2002/0016293 A1 | 2/2002 | Ratain et al. |
| 2002/0115613 A1 | 8/2002 | Kumar |
| 2002/0177609 A1 | 11/2002 | Swindell et al. |
| 2003/0065023 A1 | 4/2003 | Swindell et al. |
| 2003/0073661 A1 | 4/2003 | Matsuyama et al. |
| 2003/0119816 A1 | 6/2003 | Haesslein et al. |
| 2004/0106647 A1 | 6/2004 | Schneider et al. |
| 2004/0171809 A1 | 9/2004 | Korsmeyer et al. |
| 2004/0235783 A1 | 11/2004 | Ghyczy et al. |
| 2005/0026959 A1 | 2/2005 | Kesseler |
| 2005/0153991 A1 | 7/2005 | Gianella-Borradori et al. |
| 2005/0261253 A1 | 11/2005 | Cannizzaro et al. |
| 2006/0079478 A1 | 4/2006 | Boojamra et al. |
| 2007/0093490 A1 | 4/2007 | Prien et al. |
| 2008/0027105 A1 | 1/2008 | Suarez et al. |
| 2008/0108657 A1 | 5/2008 | Kesseler |
| 2009/0030005 A1 | 1/2009 | Kamb et al. |
| 2009/0142337 A1 | 6/2009 | Squires |
| 2010/0143350 A1 | 6/2010 | Green et al. |
| 2010/0286057 A1 | 11/2010 | Walensky et al. |
| 2011/0008371 A1 | 1/2011 | Michelson |
| 2011/0251240 A1 | 10/2011 | Suarez et al. |
| 2012/0225851 A1 | 9/2012 | Cardone et al. |
| 2013/0079424 A1 | 3/2013 | Gerber et al. |
| 2013/0122492 A1 | 5/2013 | Khosravi et al. |
| 2013/0210024 A1 | 8/2013 | Yu et al. |
| 2014/0140956 A1 | 5/2014 | Fairfax et al. |
| 2014/0286861 A1 | 9/2014 | Govindan et al. |
| 2014/0303167 A1 | 10/2014 | Choidas et al. |
| 2015/0051249 A1 | 2/2015 | Walensky |
| 2015/0150869 A1 | 6/2015 | Cardone et al. |
| 2015/0259420 A1 | 9/2015 | Triebel et al. |

(56) References Cited

U.S. PATENT DOCUMENTS

| | | |
|---|---|---|
| 2015/0301053 A1 | 10/2015 | Pierceall et al. |
| 2015/0352097 A1 | 12/2015 | Cardone et al. |
| 2015/0362479 A1 | 12/2015 | Letai et al. |
| 2016/0178612 A1 | 6/2016 | Cardone |
| 2016/0231314 A1 | 8/2016 | Ryan et al. |
| 2016/0235779 A1 | 8/2016 | Marcus |
| 2016/0258933 A1 | 9/2016 | Letai |
| 2016/0273020 A1 | 9/2016 | Pierceall et al. |
| 2016/0279106 A1 | 9/2016 | Udea et al. |
| 2017/0184567 A1 | 6/2017 | Letai |
| 2017/0260268 A1 | 9/2017 | Beatty et al. |
| 2018/0280407 A1 | 10/2018 | Warner et al. |
| 2019/0314357 A1 | 10/2019 | Bearss et al. |
| 2020/0048228 A1 | 2/2020 | Siddiqui-Jain et al. |
| 2020/0131210 A1 | 4/2020 | Siddiqui-Jain et al. |
| 2020/0200737 A1 | 6/2020 | Bearss et al. |
| 2020/0276174 A1 | 9/2020 | Bearss et al. |
| 2020/0276215 A1 | 9/2020 | Bearss et al. |
| 2020/0281949 A1 | 9/2020 | Warner et al. |
| 2020/0316084 A1 | 10/2020 | Bearss et al. |
| 2021/0052568 A1 | 2/2021 | Warner et al. |
| 2021/0228582 A1 | 7/2021 | Bearss et al. |
| 2021/0277037 A1 | 9/2021 | Siddiqui-Jain |
| 2021/0332071 A1 | 10/2021 | Siddiqui-Jain et al. |
| 2021/0379402 A1 | 12/2021 | Smith et al. |
| 2022/0125776 A1 | 4/2022 | Bearss et al. |
| 2022/0257581 A1 | 8/2022 | Bearss et al. |
| 2022/0305037 A1 | 9/2022 | Bearss et al. |
| 2022/0339172 A1 | 10/2022 | Warner et al. |
| 2023/0250116 A1 | 8/2023 | Siddiqui-Jain et al. |

FOREIGN PATENT DOCUMENTS

| | | |
|---|---|---|
| EP | 0241003 B1 | 10/1987 |
| EP | 0321918 B1 | 6/1989 |
| EP | 0253739 B1 | 10/1989 |
| EP | 0253738 B1 | 1/1990 |
| EP | 0366061 B1 | 2/1990 |
| EP | 0474129 B1 | 3/1992 |
| EP | 0507278 A2 | 10/1992 |
| EP | 0 780 386 A1 | 6/1997 |
| EP | 0606046 B1 | 10/1997 |
| EP | 0818442 A2 | 1/1998 |
| EP | 0931788 A2 | 7/1999 |
| EP | 1004578 A2 | 5/2000 |
| EP | 0979824 B1 | 10/2004 |
| FR | 2338043 | 8/1977 |
| FR | 2338043 A1 | 8/1977 |
| GB | 9912961.1 | 6/1999 |
| IN | CHENP-2007-03645 A | 11/2007 |
| JP | 2003-519698 | 6/2003 |
| JP | 2004529125 A | 9/2004 |
| JP | 2007-291111 A | 11/2007 |
| JP | 2008-513494 A | 5/2008 |
| JP | 2009-507820 A | 2/2009 |
| JP | 2011-511803 A | 4/2011 |
| JP | 2013-533213 A | 8/2013 |
| RU | 2438664 C2 | 1/2012 |
| RU | 2474582 C2 | 10/2013 |
| RU | 2552642 C2 | 10/2015 |
| WO | 90/05719 A1 | 5/1990 |
| WO | 91/00360 A1 | 1/1991 |
| WO | 92/20373 A1 | 11/1992 |
| WO | 1992/009589 A1 | 11/1992 |
| WO | 93/08829 A1 | 5/1993 |
| WO | 94/02602 A1 | 2/1994 |
| WO | 94/11026 A2 | 5/1994 |
| WO | 95/19970 A1 | 7/1995 |
| WO | 95/21613 A1 | 8/1995 |
| WO | 96/15263 A1 | 5/1996 |
| WO | 96/27011 A1 | 9/1996 |
| WO | 96/27583 A1 | 9/1996 |
| WO | 96/33172 A1 | 10/1996 |
| WO | 96/33735 A1 | 10/1996 |
| WO | 96/34096 A1 | 10/1996 |
| WO | 97/05265 A1 | 2/1997 |
| WO | 97/13760 A1 | 4/1997 |
| WO | 97/16447 A1 | 5/1997 |
| WO | 97/22596 A1 | 6/1997 |
| WO | 97/30174 A1 | 8/1997 |
| WO | 97/32856 A1 | 9/1997 |
| WO | 97/42949 A1 | 11/1997 |
| WO | 98/02434 A1 | 1/1998 |
| WO | 98/02437 A1 | 1/1998 |
| WO | 98/02438 A1 | 1/1998 |
| WO | 98/03516 A1 | 1/1998 |
| WO | 98/07697 A1 | 2/1998 |
| WO | 98/13344 A1 | 4/1998 |
| WO | 98/14451 A1 | 4/1998 |
| WO | 98/30566 A1 | 7/1998 |
| WO | 98/33768 A1 | 8/1998 |
| WO | 98/33798 A2 | 8/1998 |
| WO | 98/34915 A1 | 8/1998 |
| WO | 98/34918 A1 | 8/1998 |
| WO | 98/50356 A1 | 11/1998 |
| WO | 98/54093 A1 | 12/1998 |
| WO | 99/07675 A1 | 2/1999 |
| WO | 99/10349 A1 | 3/1999 |
| WO | 99/16755 A1 | 4/1999 |
| WO | 99/16787 A1 | 4/1999 |
| WO | 99/24440 A1 | 5/1999 |
| WO | 99/29667 A1 | 6/1999 |
| WO | 99/35132 A1 | 7/1999 |
| WO | 99/35146 A1 | 7/1999 |
| WO | 99/52889 A1 | 10/1999 |
| WO | 99/52910 A1 | 10/1999 |
| WO | 99/53049 A1 | 10/1999 |
| WO | 99/61422 A1 | 12/1999 |
| WO | 99/62890 A1 | 12/1999 |
| WO | 00/06134 A2 | 2/2000 |
| WO | 00/12071 A2 | 3/2000 |
| WO | 00/44362 A2 | 8/2000 |
| WO | 00/59526 A1 | 10/2000 |
| WO | 01/12661 A2 | 2/2001 |
| WO | 01/60814 A2 | 8/2001 |
| WO | 02/20568 A2 | 3/2002 |
| WO | 03/028001 A1 | 4/2003 |
| WO | 03/040168 A2 | 5/2003 |
| WO | 2004/022580 A2 | 3/2004 |
| WO | 2004/058804 A1 | 7/2004 |
| WO | 2005/017107 A2 | 2/2005 |
| WO | 2005/044839 A2 | 5/2005 |
| WO | 2006/099667 A2 | 9/2006 |
| WO | 2006/101846 A1 | 9/2006 |
| WO | 2006/121168 A1 | 11/2006 |
| WO | 2007/123791 A2 | 11/2007 |
| WO | 2008/021484 A1 | 2/2008 |
| WO | 2008/106635 A1 | 9/2008 |
| WO | 2008/132601 A1 | 11/2008 |
| WO | 2009/044273 A2 | 4/2009 |
| WO | 2010/019570 A2 | 2/2010 |
| WO | 2010/027827 A2 | 3/2010 |
| WO | 2010/030727 A1 | 3/2010 |
| WO | 2010/093742 A1 | 8/2010 |
| WO | 2010/147961 A1 | 12/2010 |
| WO | WO 2011/054553 A1 | 5/2011 |
| WO | 2011/066342 A1 | 6/2011 |
| WO | 2011/088137 A2 | 7/2011 |
| WO | 2011/143660 A2 | 11/2011 |
| WO | 2011/153374 A1 | 12/2011 |
| WO | WO 2012/075383 A2 | 6/2012 |
| WO | 2012/122370 A1 | 9/2012 |
| WO | 2012/145493 A1 | 10/2012 |
| WO | 2013/079174 A1 | 6/2013 |
| WO | 2013/082660 A1 | 6/2013 |
| WO | 2013/138702 A2 | 9/2013 |
| WO | 2013/170176 A2 | 11/2013 |
| WO | 2013/170176 A3 | 11/2013 |
| WO | 2013/182519 A1 | 12/2013 |
| WO | 2013/188355 A1 | 12/2013 |
| WO | 2013/188978 A1 | 12/2013 |
| WO | 2014/022758 A1 | 2/2014 |
| WO | 2014/047342 A1 | 3/2014 |
| WO | 2014/055897 A2 | 4/2014 |

(56) References Cited

FOREIGN PATENT DOCUMENTS

| | | |
|---|---|---|
| WO | 2014/059028 A1 | 4/2014 |
| WO | 2014/066848 A1 | 5/2014 |
| WO | 2014/100079 A1 | 6/2014 |
| WO | 2014/140180 A1 | 9/2014 |
| WO | 2014/179664 A2 | 11/2014 |
| WO | 2014/194302 A2 | 12/2014 |
| WO | 2014/209804 A1 | 12/2014 |
| WO | 2015/010094 A1 | 1/2015 |
| WO | 2015/017788 A1 | 2/2015 |
| WO | 2015/042249 A1 | 3/2015 |
| WO | 2015/047510 A1 | 4/2015 |
| WO | 2015/061668 A1 | 4/2015 |
| WO | 2015/066305 A1 | 5/2015 |
| WO | 2015/070020 A2 | 5/2015 |
| WO | 2015/081158 A1 | 6/2015 |
| WO | 2015/085847 A1 | 6/2015 |
| WO | 2015/109124 A2 | 7/2015 |
| WO | 2015/112800 A1 | 7/2015 |
| WO | 2015/112805 A1 | 7/2015 |
| WO | 2015/116539 A1 | 8/2015 |
| WO | 2015/130585 A1 | 9/2015 |
| WO | 2015/161247 A1 | 10/2015 |
| WO | 2015/181342 A1 | 12/2015 |
| WO | 2015/195163 A1 | 12/2015 |
| WO | 2015/200119 A1 | 12/2015 |
| WO | 2016/000619 A1 | 1/2016 |
| WO | 2016/028672 A1 | 2/2016 |
| WO | 2016/061144 A1 | 4/2016 |
| WO | 2016/071448 A1 | 5/2016 |
| WO | 2016/073913 A1 | 5/2016 |
| WO | 2016/092419 A1 | 6/2016 |
| WO | 2016/111947 A2 | 7/2016 |
| WO | 2016/115105 A1 | 7/2016 |
| WO | 2016/144803 A2 | 9/2016 |
| WO | 2016/149613 A2 | 9/2016 |
| WO | 2016/154380 A1 | 9/2016 |
| WO | 2016/161248 A1 | 10/2016 |
| WO | 2016/161270 A1 | 10/2016 |
| WO | 2016/172214 A1 | 10/2016 |
| WO | 2016/176288 A1 | 11/2016 |
| WO | 2016/176299 A1 | 11/2016 |
| WO | 2016/187316 A1 | 11/2016 |
| WO | 2017/024073 A1 | 2/2017 |
| WO | 2017/075349 A2 | 5/2017 |
| WO | WO 2017/187316 A1 | 11/2017 |
| WO | 2018/013918 A2 | 1/2018 |
| WO | 2018/094275 A1 | 5/2018 |
| WO | 2018/119000 A1 | 6/2018 |
| WO | 2019/055579 A1 | 3/2019 |
| WO | 2019/200243 A1 | 10/2019 |
| WO | 2019/246421 A1 | 12/2019 |
| WO | 2020/077300 A1 | 4/2020 |
| WO | 2020/092615 A1 | 5/2020 |
| WO | 2020/117988 A1 | 6/2020 |
| WO | 2020/118252 A1 | 6/2020 |
| WO | 2020/191326 A1 | 9/2020 |
| WO | 2021/007316 A1 | 1/2021 |
| WO | 2021/007314 A2 | 2/2021 |
| WO | WO 2021/113688 A1 | 6/2021 |

OTHER PUBLICATIONS

Al-Mawali, "Leukemic Stem Cells Shows the Way for Novel Target of Acute Myeloid Leukemia Therapy", J Stem Cell Res Ther, 3(4):1-8 (2013).

Altschul et al., *Nucleic Acids Res.* 25:3389-3402 (1997).

Alvocidib, definition of alvocidib, NCI Dictionary of Cancer Terms-National Cancer Institute, retrieved from URL: https://www.cancer.gov/publications/dictionaries/cancer-terms/def/alvocidib on Jan. 7, 2021, 1 page.

"Alvocidib Biomarker-driven Phase 2 AML Study," Sumitomo Dainippon Pharma Oncology, ClinicalTrials.gov identifier: NTC02520011, URL:https://www.clinicaltrials.gov/ct2/show/NCT02520011, Accessed: Dec. 31, 2020, 8 pages.

Araki et al., "Allogeneic Hematopoietic Cell Transplantation for Acute Myeloid Leukemia: Time to Move Toward a Minimal Residual Disease-Based Definition of Complete Remission?" J Clin Oncol 34(4):329-336 (2016).

Arguello et al., "Flavopiridol induces apoptosis of normal lymphoid cells, causes immunosuppression, and has potent antitumor activity in vivo against human leukemia and lymphoma xenografts," *Blood* 91(7):2482-2490 (1998).

Attal, M., et al., "Lenalidomide Maintenance after Stem-Cell Transplantation for Multiple Myeloma," The New England Journal of Medicine, 366:1782-1791 (2012).

Awan, F. T., et al., "A Phase I Clinical Trial of Flavopiridol Consolidation in Chronic Lymphocytic Leukemia Patients Following Chemoimmunotherapy", Ann Hematol, 95:1137-1143 (2016).

Bae et al., "Underphosphorylated BAD interacts with diverse antiapoptotic BCL-2 family proteins to regular apoptosis," *Apoptosis* 6:319-330 (2001).

Barretina et al., "The Cancer Cell Line Encyclopedia enables predictive modelling of anticancer drug sensitivity," *Nature* 483(7391):603-607 (2012); Erratum in: *Nature* 492(7428):290 (2012).

Bearss, "NOXA Priming—Predictive Biomarker for Patients With Acute Myeloid Leukemia to Improve Treatment Outcomes," 2016, retrieved from https://openforum.hbs.org/challenge/precision-medicine/submit-ideas/noxa-priming-predic . . . , 7 pages.

Bearss, "Targeting MCL1 dependent cancers by CDK9 inhibition," Abstract for Keynote Address, 9th International Conference on Leukemia and Hematologic Oncology, Oct. 5-6, 2017 London, UK, *J Hematol Thrombo Dis* 5(5 Suppl), 2017.

Beauchamp, et al., "Amino Acid Ester Prodrugs of Acyclovir", Antiviral Chemistry and Chemotherapy, 3(3):157-164 (1992).

Belikov, V.G., in *Pharamceutical Chemistry*, vol. 1, Moscow, High School, pp. 43-47 (1993) with English translation.

Belmar, J. and Fesik, S.W., "Small Molecule Mcl-1 Inhibitors for the Treatment of Cancer", Pharmacol Ther., 145:76-84 (2015).

Benyon, B., "FDA Grants Venclexta an Accelerated Approval for AML Treatment", Nov. 21, 2018, 2 pages, URL: https://www.curetoday.com/articles/fda-grants-venclexta-an-accelerated-approval-for-aml-treatment.

Berge, et al., "Pharmaceutical Salts", Journal of Pharmaceutical Sciences 66(1):1-19 (1977).

Besbes, S. and Billard, C., "First MCL-1-Selective BH3 Mimetics as Potential Therapeutics for Targeted Treatment of Cancer", Cell Death and Disease, 6:2 pages (2015).

Bible et al., "Cytotoxic Synergy Between Flavopiridol (NSC 649890, L86-8275) and Various Antineoplastic Agents: The Importance of Sequence of Administration," *Cancer Research* 57:3375-3380 (1997).

Billard, C., "BH3 Mimetics: Status of the Field and New Developments", Mol Cancer Ther, 12(9):1671-1700 (2013).

Blachly et al., "Emerging Drug Profile: Cyclin-Dependent Kinase Inhibitors," *Leuk Lymphoma* 54:2133-2143 (2013). (22 pages).

Blum, W., et al., "Phase I Clinical and Pharmakokinetic Study of a Novel Schedule of Flavopiridol in Relapsed and Refractory Acute Leukemias", Haematologica, 95(7):1098-1105 (2010).

Bodet et al., "BH3-only protein Bik is involved in both apoptosis induction and sensitivity to oxidative stress in multiple myeloma," *Br. J. Cancer* 103:1808-1814 (2010).

Boffo et al., "CDK9 Inhibitors in Acute Myeloid Leukemia," Journal of Experimental & Clinical Cancer Research, 37(36):1-10 (2018).

Bogenberger, et al., "BCL-2 Family Proteins as 5-Azacytidine-Sensitizing Targets and Determinants of Response in Myeloid Malignancies", Leukemia, 28:1657-1665 (2014).

Bogenberger et al., "Combined venetoclax and alvocidib in acute myeloid leukemia," Oncotarget 8(63):107206-107222 (2017).

Bose et al., "Mcl-1 as a therapeutic target in acute myelogenous leukemia (AML)," *Leukemia Research Reports* 2:12-14 (2013).

Bouillet et al., "Proapoptotic Bcl-2 Relative Bim Required for Certain Apoptotic Responses, Leukocyte Homeostasis, and to Preclude Autoimmunity," *Science* 286:1735-1738 (1999).

Boyd et al., "Bik, a novel death-inducing protein shares a distinct sequence motif with Bcl-2 family proteins and interacts with viral and cellular survival-promoting proteins," *Oncogene* 11(9):1921-1928 (1995).

(56) References Cited

OTHER PUBLICATIONS

Bradbury, et al., "Optimisation of a Series of Bivalent Triazolopyridazine Base Bromodomain and Exterminal Inhibitos: The Discovery of (3R)-4-[2-[4-[1-(3-methoxy-[1,2,4]triazolo[4,3-b]pyridazin-6-yl)-4-piperidyl]phenoxy]ethyl]-1,3-dimethyl-piperzin-2-one (AZD5153)", Journal of Medicinal Chemistry, 59(17):7801-7817 (2016).
Brady et al., "Reflections on a peptide," Nature 368:692-693 (1994).
Braun et al., "Preclinical Study of the Bromodomain Inhibitor OTX015 in Acute Myeloid (AML) and Lymphoid (ALL) Leukemias," Blood 122:4218 (2013). (5 pages) (Abstract Only).
Brennan et al., "Preparation of Bispecific Antibodies by Chemical Recombination of Monoclonal Immunoglobulin G1 Fragments," Science 229:81 (1985).
Brooks E. E.,et al., "CVT-313, a specific and potent inhibitor of CDK2 that prevents neointimal formation", J. Biol. Chem., 272:299207-29911 (1997).
Brunelle et al., "MCL-1-dependent leukemia cells are more sensitive to chemotherapy than BCL-2-dependent counterparts," J. Cell. Biol. 187(3):429-442 (2009).
Brunetto et al., "First-in-human, Pharmacokinetic and Pharmacodynamic Phase I Study of Resminostat, and Oral Histone Deacetylase Inhibitor, in Patients with Advanced Solid Tumors," Clinical Cancer Research 19:5494-5504 (2013).
Brüsselbach, et al., "Cell Cycle-Independent Induction of Apoptosis by the Anti-Tumor Drug Flavopiridol in Endothelial Cells", Int. J. Cancer, 77:146-152 (1998).
Buccisano, et al., "Prognostic and Therapeutic Implications of Minimal Residual Disease Detection in Acute Myeloid Leukemia", Blood, 119(2):332-341 (2012).
Buggy et al., "CRA-024781: a novel synthetic inhibitor of histone deacetylase enzymes with antitumor activity in vitro and in vivo," Mol Cancer Ther 5:1309-1317 (2006).
Buijs et al., "A novel CBFA2 single-nucleotide Mutation in Familial Platelet Disorder with Propensity to Develop Myeloid Malignancies," Blood 98(9):2856-2858 (2001).
Bundgard, H., in Design of Prodrugs, Bungard, H. ed., (NY:Elsevier),pp. 7-9 and 21-24 (1985).
Buron et al., "Use of human cancer cell lines mitochondria to explore the mechanisms of BH3 peptides and ABT-737-induced mitochondrial membrane permeabilization," PLoS One 5(3):e9924 (2010).
Burrer et al., "Selective Peptide Inhibitors of Antiapoptotic Cellular and Viral Bcl-2 Proteins Lead to Cytochrome C Release During Latent Kaposi's Sarcoma-Associated Herpesvirus Infection," Virus Res. 211:86-88 (2016). (Author's manuscript).
Byrd et al., "Flavopiridol Induces Apoptosis in Chronic Lymphocytic Leukemia Cells Via Activation of Caspase-3 Without Evidence of bcl-2 Modulation or Dependence on Functional p53," Blood 92:3804-3816 (1998).
Byrd et al., "Chronic Lymphocytic Leukemia," Hematology, pp. 163-183 (2004). (21 pages).
Byrd et al., "Flavopiridol Administered as a Pharmacologically-Derived Schedule Demonstrates Marked Clinical Activity in Refractory, Genetically High Risk, Chronic Lymphocytic Leukemia (CLL)," Blood 104:341 (2004). (2 pages).
Byrd et al., "Sequential Phase II Studies of Flavopiridol by 72-Hour Continuous Infusion and 1-Hour Intravenous Bolus for the Treatment of Relapsed B-Cell Chronic Lymphocytic Leukemia: Results from CALGB Study 19805," Blood 104:3485 (2004). (2 pages).
Byrd et al., "Treatment of Relapsed Chronic Lymphocytic Leukemia by 72-Hour Continuous Infusion or 1-Hour Bolus Infusion of Flavopiridol: Results from Cancer and Leukemia Group B Study 19805," Clin Cancer Res 11:4176-4181 (2005).
Byrd, et al., "Flavopirdol Administered Using a Pharmacologically Derived Schedule is Associated with Marked Clinical Efficacy in Refractory, Genetically High-Risk Chronic Lymphocytic Leukemia," Blood, 109(2):399-404 (2007).
Byrd, J.C., et al., "Pretreatment Cytogenetic Abnormalities are Predictive of Induction Success, Cumulative Incidence of Relapse, and Overall Survival in Adult Patients with de novo Acute Myeloid Leukemia: Results from Cancer and Leukemia Group B (CALGB8461)", Blood, 100:4325-4336 (2002).
Calin et al., "A MicroRNA Signature Associated with Prognosis and Progression in Chronic Lymphocytic Leukemia," N. Engl. J. Med., 353:1793-1801 (2005).
Cannon,J.G., "Analog Design" in Burger's Medicinal Chemistry and Drug Discovery, Fith Edition, Manfred E. Wolf ed. (NY:Wiley Interscience), 19:783-802 (1995).
Carlson et al., "Flavopiridol Induces G1 Arrest with Inhibition of Cyclin-dependent Kinase (CDK) 2 and CDK4 in Human Breast Carcinoma Cells," Cancer Research 56:2973-2978 (1996).
Caron et al., "Engineered Humanized Dimeric Forms of IgG Are More Effective Antibiotics," J. Exp. Med., 176:1191-1195 (1992).
Cartron et al., "The first α Helix of Bax Play a Necessary Role in Its Ligand-Induced Activation by the BH3-Only Proteins Bid and PUMA," Mol. Cell., 16:807-818 (2004).
CAS Registry No. 146426-40-6—Flavopiridol (1993).
CAS Registry No. 951209-71-5, "IRX 2" Entered STN Oct. 23, 2007, 1 page.
Certo et al., "Mitochondria Primed by Death Signals Determine Cellular Addiction to Antiapoptotic BCL-2 Family Members," Cancer Cell 9:351-365 (2006).
Chan, D., et al., "Belinostat and Panobinostat (HDACI): in vitro and invivo sStudies in Thyroid Cancer", J. Cancer Res.Clin. Oncol., 139:1507-1514 (2013).
Chang et al., "Adenovirus-mediated over-expression of the cyclin/cyclin-dependent kinase inhibitor, p21 inhibits vascular smooth muscle cell proliferation and neointima formation in the rat carotid artery model of balloon angioplasty," J. Clin. Invest., 96:2260-2268 (1995).
Chao et al., "Flavopiridol Inactivates P-TEFb and Blocks Most RNA Polymerase II Transcription in Vivo," The Journal of Biological Chemistry, 276:31793-31799 (2001).
Chao et al., "Flavopiridol Inhibits P-TEFb and Blocks HIV-1 Replication," The Journal of Biological Chemistry, 275:28345-28348 (2000).
Chen, et al., "Androgen Receptor Serine 81 Phosphorylation Mediates Chromatin Binding and Transcriptional Activation", Journal of Biological Chemistry, 287(11):8571-8583 (2012).
Chen et al., "Caspase cleavage of BIMel triggers a positive feedback amplification of apoptotic signaling," Proc. Natl. Acad. Sci,. USA 101(5):1235-1240 (2004).
Chen et al., "Differential Targeting of Prosurvival Bcl-2 Proteins by Their BH3-Only Ligands Allows Complementary Apoptotic Function," Molecular Cel,l 17:393-403 (2005).
Chen, C., et al., "Lenalidomide in Multiple Myeloma—a Practice Guideline", Curr Oncol, 20(2):e136-e149 (2013).
Chen et al., "Transcription inhibition by flavopiridol: mechanism of chronic lymphocytic leukemia cell death," Blood, 106:2513-2519 (2005).
Chen et al., "Mcl-1 Down-regulation Potentiates ABT-737 Lethality by Cooperatively Inducing Bak Activation and Bax Translocation," Cancer Res 67(2):782-791 (2007).
Chen et al., "Mechanism of action of SNS-032, a novel cyclin-dependent kinase inhibitor in chronic lymphocytic leukemia," Blood, 113:4637-4645 (2009).
Chen D., "Downregulation of cyclin-dependent kinase 2 activity and cyclin A promoter activity in vascular smooth muscle cells by p27(KIP1), an inhibitor of neointima formation in the rat carotid artery", J. Clin. Invest., 99:2334-2341 (1997).
Cheng et al., "Bax-independent inhibition of apoptosis by Bcl-X1," Nature 379:554-556, 1996.
Cheng et al., "BCL-2, BCL-X1 Sequester BH3 Domain-Only Molecules Preventing BAX- and BAK-Mediated Mitochondrial Apoptosis," Mol. Cell, 8(3):705-711 (2001).
Cheronis, "Semimicro Experimental Organic Chemistry," deGratt, pp. 67-69 (1958).
Cheson et al., "National Cancer Institute-Sponsored Working Group Guidelines for Chronic Lymphocytic Leukemia: Revised Guidelines for Diagnosis and Treatment," Blood 87:4990-4997, 1996.
Chipuk et al., "Direct Activation of Bax by p53 Mediates Mitochondrial Membrane Permeabilization and Apoptosis," Science 303:1010-1014 (2004).

(56) References Cited

OTHER PUBLICATIONS

Chittenden et al., "A conserved domain in Bak, distinct from BH1 and BH2, mediates cell death and protein binding functions," *EMBO J* 14(22):5589-5596 (1995).
Chittenden et al., "Induction of apoptosis by the Bcl-2 homologue Bak," *Nature* 374(6524):733-736 (1995).
Chonghaile et al., "Mimicking the BH3 domain to kill cancer cells," *Oncogene* 27:S149-S157 (2009).
Chonghaile et al., "Mitochondrial Apoptotic Priming Measured by BH3 Profiling Regulates Clinical Response to Chemotherapy in Myeloma and Acute Lymphoblastic Leukemia and Explains Therapeutic Index," Abstract 1442, 53rd ASH Annual Meeting and Exposition, Dec. 10-13, 2011, American Society of Hematology.
Chonghaile et al., "Pretreatment mitochondrial priming correlates with clinical responsive to cytotoxic chemotherapy," *Science* 334(6059):1129-1133 (2011). (6 pages).
Chou, T.-C. and Talalay, P., "Quantitative Analysis of Dose-Effect Relationships: The Combined Effects of Multiple Drugs or Enzyme Inhibitors", Advances in Enzyme Regulation, 22:27-55 (1985).
Choudhary et al., "MCL-1 and BCL-xL-dependent resistance to the BCL-2 inhibitor ABT-199 can be overcome by preventing PI3K/AKT/mTOR activation in lymphoid malignancies," *Cell Death and Disease* 6:e1593 (2015). (12 pages).
Christian, B. A., et al., "Flavopiridol in Chronic Lymphocytic Leukemia: A Concise Review," Clinical Lymphoma & Myeloma, 9(Suppl 3):S179-S185 (2009).
Clinical Study, No Authors Available, "Alvocidib, Followed by Cytarabine + Mitoxantrone, Makes Impact in AML", Inpharma Weekley, 1606:8 (2007).
Clowes et al., "Significance of quiescent smooth muscle migration in the injured rat carotid artery," *Circ. Res.* 56(1):139-145 (1985).
Cole et al., "The EBV-Hybridoma technique and its application to human lung cancer," *Monoclonal Antibodies and Cancer Therapy*:77-96 (1985).
Common Terminology Criteria for Adverse Events (CTCAE) Version 5.0 Publichsed: Nov. 7, 2017 U.S. Department of Health and Human Services, National Institutes of Health, National Cancer Institute, URL=https://ctep.cancer.gov/protocoldevelopment/electronic_applications/docs/CTCAE_v5_Quick Reference Accessed: Dec. 31, 2020, 147 pages.
Conaway et al., "The Mediator Complex and Transcription Elongation," *Biochim Biophys Acta* 1829:69-75 (2013). (16 pages).
Corbett, et al., "Evaluation of Single Agents and Combinations of Chemotherapeutic Agents in Mouse Colon Carcinomas", Cancer 40:2660-2680 (1987).
Corbett, et al., "Response to Transplantable Tumors of Mice to Antracenedione Derivatives Alone and in Combination with Clinically Useful Agents", Cancer Treatment Reports 66:1187-1200 (1982).
Cory et al., "The Bcl2 Family: Regulators of the Cellular Life-Or-Death Switch," *Nat. Rev. Cancer* 2(9):647-656 (2002).
Cosulich et al., "Regulation of apoptosis by BH3 domains in a cell-free system," *Curr. Biol* 7(12):913-920 (1997).
Cote et al., "Generation of human monoclonal antibiotics reactive with cellular antigens," *Proc. Natl. Acad. Sci. USA* 80:2026-2030, 1983.
Czabotar et al., "Bax Activation by Bim?," *Cell Death and Differentiation* 16:1187-1191 (2009).
Czabotar et al., "Structural insights into the degradation of Mcl-1 induced by BH3 domains," *PNAS* 104:6217-6222 (2007).
Czech et al., "Antitumoral activity of flavone L 86-8275," *International Journal of Oncology* 6:31-36 (1995).
Daigle et al., "Potent Inhibition of DOT1L as Treatment of MLL-fusion Leukemia," *Blood* 122:1017-1025 (2013).
Danial et al., "Cell Death: Critical Control Points," *Cell* 116:205-219 (2004).
Davids et al., "BH3 profiling demonstrates that restoration of apoptotic priming contributes to increased sensitivity to PI3K inhibition in stroma-exposed chronic lymphocytic leukemia cells," *Blood* 118(21): Nov. 18, 2011, Abstract.

Davids et al., "Targeting the B-cell lymphoma/leukemia 2 family in cancer," *J Clin Oncol* 30(25):3127-3135 (2012).
Dawson, M.A., et al., "Inhibition of BET Recruitment to Chromatin as an Effective Treatment for MLL-Fusion Leukaemia", Nature, 478:328-333 (2011).
De Azevedo Jr. et al., "Structural basis for inhibition of cyclin-dependent kinase 9 by flavopiridol," *Biochemical and Biophysical Research Communications* 293:566-571 (2002).
De Azevedo, Jr., et al., "Structural Basis for Specificity and Potency of a Flavanoid Inhibitor of Human CDK2, a Cell Cycle Kinase", Proc. Natl. Acad. Sci., 93:2725-2740 (1996).
Debrincat et al., "BCL-2 is dispensable for thrombopoiesis and platelet survival," *Cell Death & Disease* 6:e1721 (2015). (8 pages).
Degrado, "Designs of peptides and proteins," *Adv. Protein Chem* 39:51-124 (1988).
De Haas et al., "Initial Diagnostic Work-Up of Acute Leukemia: ASCO Clinical Practice Guideline Endorsement of the College of American Pathologists and American Society of Hematology Guideline," J Clin Oncol 37(3):239-253 (2018).
Dehm, et al., "Alternatively Spliced Androgen Receptor Variants", Endocrine—Related Cancer, 18(5):R183-R196 (2011).
Deng et al., "BH3 Profiling Identifies Three Distinct Classes of Apoptotic Blocks to Predict Response to ABT-737 and Conventional Chemotherapeutic Agents," *Cancer Cell* 12:171-185 (2007).
Derenne et al., "Antisense strategy shows that Mcl-1 rather than Bcl-2 of Bcl-xl is an essential survival protein of human myeloma cells," *Blood* 100:194-199 (2002).
Desagher et al., "Bid-induced Conformational Change of Bax Is Responsible for Mitochondrial Cytochrome c Release during Apoptosis," *J. Cell Biol* 144(5): 891-901 (1999).
Dettman et al., "Abstract 3400: Mitochondrial profiling in AML patients treated with an Alvocidib containing regimen reveals MCL1 dependency in responder bone marrow," *Cancer Res* 75:3400 (2015). (2 pages).
De Young et al., "Gene therapy for restenosis, Are We Ready?" *Circ. Res.* 82:306-313 (1998).
Di Lisa et al., "Mitochondrial Function and Cell Injury in Single Cardiac Myocytes Exposed to Anoxia and Reoxygenation," *Transplant. Proc.* 27(5):2829-2830 (1995).
Di Lisa et al., "Mitochondrial membrane potential in single living adult rat cardiac myocytes exposed to anoxia or metabolic inhibition," *J. Physiol* 486(1):1-13 (1995).
Diamandis et al., *Immunoassays*, Academic Press, Inc., NY, 1996.
Dillman, R.O., et al., "A Comparative Study of Two Different Doses of Cytarabine for Acute Myeloid Leukemia: A Phase III Trial of Cancer and Leukemia Group B", Blood, 78(10):2520-2526 (1991).
Dimopoulos et al., "Multiple Myeloma: EAH-ESMO Clinical Practice Guidelines for Diagnosis, Treatment and Follow-Up," Annals of Oncology 32(3):309-322, 2021.
Dinardo, C.D., et al., "Venetoclax Combined with Decitabine or Azacitidine in Treatment-Naïve, Elderly Patients With Acute Myeloid Leukemia", Blood, 133:7-17 (2019).
Dinnen et al., "Redirecting Apoptosis to Aponecrosis Induces Selective Cytotoxicity to Pancreatic Cancer Cells through Increased ROS, Decline in ATP Levels, and VDAC," *Molecular Cancer Therapeutics* 12:2792-2803 (2013).
Dittmann et al., "The Commonly Used PI3-Kinase Probe LY294002 Is an Inhibitor of BET Bromodomains," ACS Chem. Biol. 9(2):495-502 (2014).
Döhner, et al., "Genomic Abberations and Survival in Chronic Lymphocytic Leukemia," NEJM, 343:1910-1916 (2000).
Döhner et al., "Diagnosis and Management of AML in Adults: 2017 ELN Recommendations From an International Expert Panel," Blood 129(4):424-447, 2017.
Döhner, H., et al., "Acute Myeloid Leukemia", The New England Journal of Medicine, 373(12), 1136-1152 (2015).
Drees et al., "Flavopiridol (L86-8275): Selective antitumor activity in vitro and activity in vivo for prostate carcinoma cells," *Clin. Cancer Res.* 3:273-279 (1997).
Egle et al., "Bim is a suppressor of Myc-induced mouse B cell leukemia," *Proc. Natl. Acad. Sci USA* 101(16):6164-6169 (2004).

(56) References Cited

OTHER PUBLICATIONS

Eichhorst et al., "Chronic Lymphocytic Leukaemia: ESMO Clinical Practice Guidelines for diagnosis, treatment and follow up," Annals of Oncology 32(1):23-33, 2020.
Ellerby et al., "Anti-cancer activity of targeted pro-apoptotic peptides," Nat. Med. 5(9):1032-1038 (1999).
Elliott et al., "Intracellular Trafficking and Protein Delivery by a Herpesvirus Structural Protein," Cell 88:223-233 (1997).
Elston et al., "Pathological prognostic factors in breast cancer. I. The value of histological grade in breast cancer: experience from a large study with long-term follow-up," Histopathology 19:403-410 (1991).
Ember et al., "Acetyl-lysine Binding Site of Bromodomain-Containing Protein 4 (BRD4) Interacts with Diverse Kinase Inhibitors," ACS Chemical Biology 9:1160-1171 (2014).
Eskes et al., "Bid Induces the Oligomerization and Insertion of Bax into the Outer Mitochondrial Membrane," Mol. Cell. Biol. 20(3):929-935 (2000).
Evans, "Clathrate Compouns" in an Introduction to Crystal Chemistry, (London:Cambridge University Press), pp. 393-397 (1964).
Falkenberg et al., "Histone deacetylases and their inhibitors in cancer, neurological diseases and immune disorders," Nature Reviews Drug Discovery 13:673-691 (2014).
Fanidi et al., "Cooperative interaction between c-myc and -2 proto-oncogenes," Nature 359:554-556 (1992).
Fenaux et al., "Myelodysplastic syndromes: ESMO Clinical Practice Guidelines for diagnosis, treatment and follow-up," Annals of Oncology 25(Supplement 3):iii57-iii69 (2014).
Fernandez, et al., "Anthracycline Dose Intesification in Acute Myeloid Leukemia", New England Journal of Medicine, 361(13):1249-1259 (2009).
Ferrara, et al., "Consensus-Based Definition of Unfitness to Intensive and Nonintensive Chemotherapy in Acute Myeloid Leukemia: a Project of SIE, SIES and GITMO Group on a New Tool for Therapy Decision Making", Leukemia, 27:997-999 (2013).
Férriz, J.M. and Vinová, J., "Prodrug Design of Phenolic Drugs", Current Pharmaceutial Design, 16:2033-2052 (2010).
Filippakopoulos et al., "Targeting bromodomains: epigenetic readers of lysine acetylation," Nature Reviews Drug Discovery 13:337-356 (2014).
Filippakopoulos, et al., "Selective Inhibition of BET Bromodomains," Nature, 468:1067-1073 (2010).
Fish, et al., "Identification of a Chemical Probe for Bromo and Extra C-Terminal Bromodomain Inhibition through Optimization of a Fragment-Derived Hit," J Med. Chem., 55:9831-9837 (2012).
Fiskum et al., "[21] Apoptosis-Related Activities Measured with Isolated Mitochondria and Digitonin-Permeabilized Cells," Methods in Enzymology 322:222-234 (2000).
Fiskus et al., "Highly Active Combination of BRD4 Antagonist and Histone Deacetylase Inhibitor against Human Acute Myelogenous Leukemia Cells," Molecular Cancer Therapeutics 13:1142-1154 (2014).
Flinn et al., "Flavopiridol Administered as a 24-Hour Continuous Infusion in Chronic Lymphocytic Leukemia lacks Clinical Activity," Leukemia Res 29:1253-1257 (2005).
Foight et al., "Designed BH3 Peptides with High Affinity and Specificity for Targeting Mcl-1 in Cells," ACS Chem. Biol. 9:1962-1968 (2014).
Frankel et al., "Activity of synthetic peptides from the Tat protein of human immunodeficiency virus type 1," Proc. Natl. Acad. Sci. USA 86:7397-7401 (1989).
Freeman et al., "Measurable Residual Disease at Induction Redefines Partial Response in Acute Myeloid Leukemia and Stratifies Outcomes in Patients at Standard Risk Without NPM1 Mutations," J Clin Oncol 36(15):1486-1497 (2018). (24 pages).
Freeman et al., "Prognostic Relevance of Treatment Response Measured by Flow Cytometric Residual Disease Detection in Older Patients with Acute Myeloid Leukemia," J Clin Oncol 31(32):4123-4131 (2013).
Freidman et al., "Precision medicine for cancer with next-generation functional diagnostics," Nat Rev Cancer 15(12):747-756 (2015).
Fuchs et al., "Pathway for Polyarginine Entry into Mammalian Cells," Biochemistry 43(9):2438-2444 (2004).
Fukui et al., "The Analysis of the Effect of JQ1 and Flavopiridol on Chondrocytes under Inflammatory Stimuli", ORS 2014 Annual Meeting, 4 pages.
Futaki et al., "Arginine-rich Peptides: An Abundant Source of Membrane-Permeable Peptides Having Potential as Carriers for Intracellular Protein Delivery," J. Biol. Chem 276(8):5836-5840 (2001).
Gambella et al., "Minimal Residual Disease by Flow Cytometry and Allelic-Specific Oligonucleotide Real-Time Quantitative Polymerase Chain Reaction in Patients With Myeloma Receiving Lenalidomide Maintenance: A Pooled Analysis," Cancer 125:750-760, 2019.
Gao et al., "Multiple Myeloma Cancer Stem Cells," Oncotarget 7(23):35466-35477 (2016).
George, B., et al., "A Phase I, First-in-Human, Open-Label, Dose-Escalation, Safety, Pharmacokinetic, and Pharmacodynamic Study of Oral TP-1287 Administered Daily to Patients with Advanced Solid Tumors", Journal of Clinical Oncology, 38(15) Abstract 3611-3 pages (2020).
Geng et al., "Apoptosis of vascular smooth muscle cells induced by in vitro stimulation with interferon-γ, tumor necrosis factor-α, and interleukin-1β," Arterioscler. Thromb. Biol 16:19-27, 1996.
Gerber et al., "Association of acute myeloid leukemia's most immature phenotype with risk groups and outcomes," Haematologica 101(5): 607-616 (2016).
Gerber, et al., A Clinically Relevant Population of Leukemic CD34+ CD38-Cells in Acute Myeloid Leukemia, Blood, 119(15):3571-3577 (2012).
Geserick et al., "The ratio of Mcl-1 and Noxa determines ABT737 resistance in squamous cell carcinoma of the skin," Cell Death and Disease 5:e1412 (2014). (14 pages).
Ghyczy et al., "Electrophilic Methyl Groups Present in the Diet Ameliorate Pathological States Induced by Reductive and Oxidative Stress: A Hypothesis," British Journal of Nutrition 85(4):409-414 (2001).
Giles et al., "A Phase I Study of Intravenous LBH589, a Novel Cinnamic Hydroxamic Acid Analogue Histone Deacetylase Inhibitor in Patients with Refractory Hematologic Malignancies," Clin Cancer Res 12:4628-4635, 2006.
Gojo et al., "The Cyclin-dependent Kinase Inhibitor Flavopiridol Induces Apoptosis in Multiple Myeloma Cells through Transcriptional Repression and Down-Regulation of Mcl-1," Clinical Cancer Research 8:3527-3538 (2002).
Goldsmith et al., "BH3 peptidomimetics potentially activate apoptosis and demonstrate single agent efficacy in neuroblastoma," Oncogene 25:4525-4533 (2006).
Gores, et al., "Selectively Targeting Mcl-1 for the Treatment of Acute Myelogeneous Leukemia and Solid Tumors", Genes & Development, 26:305-311 (2012).
Göttlicher, et al., "Valproic Acid Defines a Novel Class of HDAC Inhibitors Inducing Differentiation of Transformed Cells," The EMBO Journal, 20(24):6969-6978 (2001).
Green et al., "A matter of life and death," Cancer Cell 1:19-30 (2002).
Green et al., "The Pathophysiology of Mitochondrial Cell Death," Science 305:626-629 (2004).
Green, "Life, Death, BH3 Profiles, and the Salmon Mousse," Cancer Cell 12:97-99 (2007).
Griffiths et al., "Cell Damage-induced Conformational Changes of the Pro-Apoptotic Protein Back In Vivo Precede the Onset of Apoptosis," J. Cell. Biol. 144(5):903-914 (1999).
Gross et al., "Enforced dimerization of BAX results in its translocation, mitochondrial dysfunction and apoptosis," EMBO J 17(14):3878-3885 (1998).
Gruber et al., "Efficient Tumor Cell Lysis Mediated by a Bispecific Single Chain Antibody Expressed in Escherichia coli," J. Immunol 152:5368-5374 (1994).

(56) References Cited

OTHER PUBLICATIONS

Guha, "Cyclin-dependent kinase inhibitors move into Phase III," *Nature Reviews Drug Discovery* 11:892-894 (2012).
Gul et al., "Apoptotic blocks and chemotherapy resistance: strategies to identify Bcl-2 protein signatures," *Briefings in Functional Genomics and Proteomics* 7(1):27-34, 2008.
Hamid, et al., "Safety and Tumor Responses with Lambrolizumab (Anti-PD-1) in Melanoma", The New England Journal of Medicine, 369(2):134-144 (2013).
Hanahan et al., "Heritable formation of pancreatic β-cell tumors in transgenic mice expressing recombinant insulin/simian virus 40 oncogenes," *Nature* 315:115-122 (1985).
Hanahan et al., "The Hallmarks of Cancer," *Cell* 100:57-70 (2000).
Hans et al., "β-Carbolines induce apoptosis in cultured cerebellar granule neurons via the mitochondrial pathway," *Neuropharmacology* 48:105-117 (2005).
Harada et al., "Survival factor-induced extracellular signal-regulated kinase phosphorylates BIM, inhibiting its association with BAX and proapoptotic activity," *Proc. Natl. Acad. Sci. USA* 101(43):15313-15317 (2004).
Harada et al., "Discovery of potent and orally bioavailable 17β-hydroxysteroid dehydrogenase type 3 inhibitors," *Bioorganic & Medicinal Chemistry* 20:3242-3254 (2012).
Harkevich, D. A., In Pharmacology 3rd Ed., Moscow, Medicine, pp. 51-55, (1987) with English translation.
Haws et al., "E881: By an MCL-1 Dependent Mechanism, Alvocidib Potentiates the Activity of Cytarabine and Mitoxantrone when Administered in a Time Sequential Regimen in AML", Hematologica 102(Suppl. 2):362 (2017).
Haws et al., "E1204: Alvocidib Synergizes with Venetoclax in Preclinical Models of Multiple Myeloma", Hematologica 102(Suppl. 2):495 (2017).
"Hematologic Malignancies: Regulatory Considerations for Use of Minimal Residual Disease in Development of Drug and Biological Products for Treatment, Guidance for Industry," U.S. Department of Health and Human Services, Food and Drug Administration, Oncology Center of Excellence (OCE), Center for Drug Evaluation and Research (CDER), Center for Biologics Evaluation and Research (CBER), Jan. 2020, available from https://www.fda.gov/media/134605/download. 21 pages.
Hemann et al., "Evasion of the p53 tumour surveillance network by tumour-derived MYC mutants," *Nature* 436:807-811 (2005).
Hemann et al., "Suppression of tumorigenesis by the p53 target PUMA," *Proc. Natl. Acad. Sci. USA* 101(25):9333-9338 (2004).
Hengartner et al., "*C. elegans* Cell Survival ced-9 Encodes a functional Homolog of the Mammalian Proto-Oncogene bcl-2," *Cell* 76:665-676 (1994).
Heuser et al., "Acute Myeloid Leukaemia in Adult Patients: ESMO Clinical Practice Guidelines for diagnosis, treatment and follow-up," Annals of Oncology 31(6):697-712, 2020.
Hewings et al., "Optimization of 3,5-Dimethylisoxazole Derivatives as Potent Bromodomain Ligands" *J. Med. Chem.*, 56:3217-3227 (2013).
Higuchi, T. and Stella, V., "Pro-drugs as Novel Delivery Systems," A.C.S. Symposium Series 14; ACS meeting, Atlantic City, NJ 1975, 118 pages.
Hillengass et al., "Minimal Residual Disease in Multiple Myeloma: Use of Magnetic Resonance Imaging," Seminars in Hematology 55(1):19-21 (2018). (Abstract Only).
Hirst et al., "Application of Non-Parametric Regression to Quantitative Structure-Activity Relationships," *Bioorganic & Medicinal Chemistry* 10:1037-1041 (2002).
Hnisz et al., "Super-Enhancers in the Control of Cell Identity and Disease," *Cell* 155:934-947 (2013).
Hoelzer et al., "Acute Lymphoblastic Leukaemia in adult patients: ESMO Clinical Practice Guidelines for diagnosis, treatment, and follow-up" Annals of Oncology 27(Supplement 5):v69-v82 (2016).
Holinger et al., "Bak BH3 Peptides Antagonize Bcl-xl Function and Induce Apoptosis through Cytochrome c-independent Activation of Caspases," *J. Biol. Chem.* 274(19):13298-13304 (1999).

Hollenbach, et al., "A Comparison of Azacitidine and Decitabine Activities in Acute Myeloid Leukemia Cell Lines", PLoS One, 5(2):10 pages (2010).
Holliger et al., "Diabodies: Small bivalent and bispecific antibody fragments," *Proc. Natl. Acad. Sci. USA* 90:6444-6448 (1993).
Hoogenboom et al., "By-passing Immunisation, Human Antibodies from Synthetic Repertoires of Germlike VH Gene Segments rearranged in Vitro," *J. Mol. Biol.* 227:381-388 (1992).
Hopp et al., "Prediction of protein antigenic determinants from amino acid sequences," *Proc. Natl. Acad. Sci. USA* 78:3824-3828, 1981.
Hoppel et al., "The action of digitonin on rat liver mitochondria. The effects on enzyme content," *Biochem J.* 107(3):367-375, 1968.
Hourigan et al., "Development of therapeutic agents for elderly patients with acute myelogenous leukemia," *Curr Opin Investig Drugs*, 11(6): 669-677 (2010).
Hourigan, C.S. and Karp, J.E., "Minimal Residual Disease in Acute Myeloid Leukaemia", Nature, 10:460-471 (2013).
Hsu et al., "Nonionic Detergents Induce Dimerization among Members of the Bcl-2 Family," *J. Biol. Chem* 272(21):13829-13834 (1997).
Huang et al., "BH3-Only Proteins—Essential Initiators of Apoptotic Cell Death," *Cell* 103:839-842 (2000).
Huber et al., "Profile of venetoclax and its potential in the context of treatment of relapsed or refractory chronic lymphocytic leukemia," *Onco. Targets Ther.* 10:645-656, 2017.
Hunter, T., "Braking the cycle," *Cell* 75:839-841, 1993.
Hunter, T., "Protein kinases and phosphatases: The yin and yang of protein phosphorylation and signaling," *Cell* 80:225-236 (1995).
Huse et al., "Generation of a large Combinatorial Library of the Immunoglobulin Repertoire in Phage Lambda," *Science* 246:1275-1281 (1989).
Innocenti et al., "Flavopiridol Metabolism in Cancer Patients Is Associated with the Occurrence of Diarrhea," *Clinical Cancer Research* 6:3400-3405 (2000).
Inohara et al., "Harakiri, a novel regulator of cell death, encodes a protein that activates apoptosis and interacts selectively with survival-promoting proteins Bcl-2 and Bcl-X1," *EMBO J* 16(7):1686-1694 (1997).
Ishizawa et al., "Mitochondrial Profiling of Acute Myeloid Leukemia in the Assessment of Response to Apoptosis Modulating Drugs," *PLoS One* 10:e0138377 (2015).
Itzykson, R. and Fenaux, P., "Predicting the Outcome of Pateients with Higher-Risk Myelodysplastic Syndrome Treated with Hypomethylating Agents", Leukemia & Lymphoma, 53(5):760-762 (2012).
Ivey et al., "Assessment of Minimal Residual Disease in Standard-Risk AML," The New England Journal of Medicine, 374(5):422-433 (2016).
Jackson et al., "Heat shock induces the release of fibroblast growth factor 1 from NIH 3T3 cells," *Proc. Natl. Acad. Sci. USA* 89:10691-10695 (1992).
Jameson et al., "A rationally designed CD4 analogue inhibits experimental allergic encephalomyelitis," *Nature* 368:744-746 (1994).
Ji, et al., "A Pharmacokinetic/Pharmacodynamic Model of Tumor Lysis Syndrome in Chronic Lynphocytic Leukemia Patients Treated with Flaovpiridol", Clinical Cancer Research, 19(5):1269-1280 (2013).
Jones et al., "Replacing the complementarily-determining regions in a human antibody with those from a mouse," *Nature* 321:522-525, 1986.
Jongen-Lavrencic et al., "Molecular Minimal Residual Disease in Acute Myeloid Leukemia," The New England Journal of Medicine, 378(13):1189-1199 (2018).
Jonkers, et al., "Oncogene Addition: Sometimes a Temporary Slavery," Cancer Cell, 6:535-538 (2004).
Jornada, D.H., et al., "The Prodrug Approach: A Successful Tool for Improving Drug Solubility", Molecules, 21,42, 31 pages (2016).
Kantajian, et al., "Decitabine Improves Patient Outcomes in Myelodysplastic Syndromes", Cancer, 106(8):1794-1803 (2006).
Karp, et al., "Timed Sequential Therapy of Acute Leukemia with Flavopiridol: In Vitro Model for a Phase I Clinical Trial", Clinical Cancer Research, 9:307-315 (2003).

(56) References Cited

OTHER PUBLICATIONS

Karp et al., "Phase I and pharmacokinetic study of flavopiridol followed by 1-beta-D-arabinofuranosylcytosine and mitoxantrone in relapsed and refractory adult acute leukemias," Clin. Cancer Res. 11(23):8403-8412 (2005).
Karp, et al., Phase I and Pharmacokinetic Study of Bolus-Infusion Flavopiridol Followed by Cytosine arabinoside and mitoxantrone for Acute Leukemias:, Blood, 117(12):3302-3310 (2011).
Karp et al., "Sequential flavopiridol, cytosine arabinoside, and mitoxantrone: a phase II trial in adults with poor-risk acute myelogenous leukemia," *Clin. Cancer Res. 13*(15 Pt. 1):4467-4473 (2007).
Karp, et al., "Radomized Phase II Study of Two Schedules of Flavopiridol Given as Timed Sequential Therapy with Cytosine Arabinoside and Mitoxantrone for Adults with Newly Diagnosed, Poor-Risk Acute Myelogenous Leukemia", Hematologica, 97(11):1736-1742 (2012).
Kasper et al., "Targeting MCL-1 sensitizes FLT3-ITD-positive leukemias to cytotoxic therapies," *Blood Cancer J 2*: 10 pages (2012).
Kaur, et al., "Growth Inhibition with Reversible Cell Cycle Arrest of Carcinome Cells by Falvone L86-8275,", JNCI, 22(84):1736-1740 (1992).
Kearney et al., "Histopathology of in-stent restenosis in patients with peripheral artery disease," *Circulation 95*:1998-2002 (1997).
Keating et al., "Results of First Salvage Therapy for Patients Refractory to a Fludarabine Regimen in Chronic Lymphocytic Leukemia," *Leuk. Lymph. 43*:1755-1762 (2002).
Keating et al., "Therapeutic role of alemtuzumab (Campath-1H) in patients who have failed fludarabine: results of a large international study," *Blood 99*:3554-3561 (2002).
Kelekar et al., "Bad is a BH3 Domain-Containing Protein that Forms an Inactivating Dimer with Bcl-xl," *Mol. Cell. Biol. 17*(12):7040-7046 (1997).
Kelekar et al., "Bcl-2-family proteins: the role of the BH3 domain in apoptosis," *Trends in Cell Biol 8*:324-330 (1998).
Kelland, L.R., "Flavopiridol, The First Cyclin-Dependent Kinase Inhibitor to Enter the Clinic: Current Status", *Expert Opinion on Investigational Drugs 9*(12):2903-2911 (2000).
Kern et al., "Determination of Relapse Risk Based on Assessment of Minimal Residual Disease during Complete Remission by Multiparameter Flow Cytometry in Unselected Patients with Acute Myeloid Leukemia," Blood 104(10):3078-3085 (2004).
KG-1a, ATCCR® CCC-246.1™ ATCC Product Sheet, 3 pages, May 31, 2013.
Kim et al., "Alvocidib Potentiates the Activity of Cytarabine and Mitoxantrone through the Targeting of MCL-1 When Administered in a Time Sequential Regimen in AML," Blood 126(23), 3799 (2015). (Abstract Only).
Kim, W., et al., "Alvocidib Potentiates the Activity of Azacytidine in an MCL-1-Dependent Fashion", Blood, 126(23): Abstract 1343, 3 pages (2015).
Kim et al., "Abstract 3728: Targeting MCL-1 expression, through the inhibition of CDK9 and super enhancer driven transcription, offers multiple opportunities for rational drug combinations," *Cancer Research 76*(14 Suppl.):3728 (2016).
Kim et al., "Alvocidib Synergizes with Cytarabine and Daunorubicin (7+3) in Preclinical Models of Acute Myeloid Leukemia", *EHA Learning Center*, May 18, 2017, retrieved from https://learningcenter.ehaweb.org/eha/2017/22nd/180678 3 pages.
Kim, et al., "TP-1287, an oral prodrug of the cyclin-dependent kinase-9 inhibitor alvocidib", EHA Library Jun. 9, 2016. (Abstract) Retrieved on Jan. 24, 2020 URL:https://library.ehaweb.org/eha/2016/21st/132440/clifford.whatcott.tp-1287.prodrug.of.the.cyclin-dependent.kinase-9.htm; poster.
Kim, et al., "The CDK9 Inhibitor, Alvocidib, Potentiates the Non-Clinical Activity of Azacytidine or Decitabine in an MCL-1-Dependent Fashio, Supporting Clinical Exploration of a Decitabine and Alvocidib Combination", Blood, 132(suppl 1):4355—6 pages (2018).

Kimura, et al., "Antiproliferative and Antitumor Effects of Azacitidine Against the Human Myelodysplastic Syndrome Cell Line SKM-1", Anticancer Reasearch, 32:795-798 (2012).
Kitada et al., "Protein kinase inhibitors flavopiridol and 7-hydroxystaurosporine down-regulate antiapoptosis proteins in B-cell chronic lymphocytic leukemia," *Blood 96*:393-397 (2000).
Klaeger, et al., "The Target Landscape of Clinical Kinase Drugs", Science, 358:1148-1164 (2017).
Knutson, et al., "Synergistic Anti-Tumor Activity of EZH2 Inhibitors and Glucocorticoid Receptor Agonists in Models of Germinal Center Non-Hodgkin Lymphomas", PLoS One, 9(12):e111840 (2014).
Kohler et al., "Continuous cultures of fused cells secreting antibody of predefined specificity," *Nature 256*:495-497, 1975.
König et al., "The Novel Cyclin-Dependent Kinase Inhibitor Flavopiridol Downregulates Bcl-2 and Induces Growth Arrest and Apoptosis in Chronic B-Cell Leukemia Lines," *Blood 90*:4307-4312 (1997).
Konopleva et al., "BCL-2 Inhibition in AML: An Unexpected Bonus?" Blood 132(10):1007-1012 (2018).
Korsmeyer et al., "Pro-apoptotic cascade activates BID, which oligomeizes BAK or BAX into pores that result in the release of cytochrome c," *Cell Death Differ 7*(12):1166-1173 (2000).
Kozbor et al., "The production of monoclonal antibodies from human lymphocytes," *Immunol Today 4*:72-79, 1983.
Kryštof et al., "Cyclin-Dependent Kinase Inhibitors as Anticancer Drugs," *Current Drug Targets 11*:291-302 (2010).
Kumar et al., "International Myeloma Working Group Consensus Criteria for Response and Minimal Residual Disease Assessment in Multiple Myeloma," *Lancet Oncology 17*:e328-e346 (2016).
Kuwana et al., "Bid, Bax, and Lipids Cooperate to Form Supramolecular Openings in the Outer Mitochondrial Membrane," *Cell 111*:331-342 (2002).
Kuwana, et al., "BH3 Domains of BH3-Only Proteins Differentially Regulate Bax-Mediated Mitochondrial Membrane Permeabilization Both Directly and Indirectly," Molecular Cell, 17:525-535 (2005).
Kyte et al., "A Simple Method for displaying the Hydropathic Character of a protein," *J. Mol. Biol. 157*:105-132, 1982.
LA Vieira et al., "Cell permeable BH3-peptides overcome the cytoprotective effect of Bcl-2 and Bcl-$X_L$," *Oncogene 21*:1963-1977 (2002).
Labi et al., "Targeting the Bcl-2-regulated apoptosis pathway by BH3 mimetics: a breakthrough in anticancer therapy?," *Cell Death and Differentiation 15*:977-987, 2008.
Landgren, "MRD Testing in Multiple Myeloma: From a Surrogate Marker of Clinical Outcomes to an Every-Day Clinical Tool," Seminars in Hematology 55(1):1-3 (2018). (Abstract Only).
Landgren et al., "MRD Testing in Multiple Myeloma: The Main Future Driver for Modern Tailored Treatment," Seminars in Hematology 55(1):44-50 (2018). (Abstract Only).
Lazarus, et al., "High-Dose Cytosine Arabinoside and Daunorubicin as Primary Therapy in Elderly Patients with Acute Myelogenous Leukemia", Cancer, 63:1055-1059 (1989).
Lemke et al., "Immunobiology of the TAM Receptors," *Nature Reviews Immunology 8*:327-336, 2008.
Leo et al., "Characterization of the Antiapoptotic Bcl-2 Family Member Myeloid Cell Leukemia-1 (Mcl-1) and the Stimulation of Its Message by Gonadotropins in the Rat Ovary," *Endocrinol 140*:5469-5477 (1999).
Letai et al., "Distinct BH3 domains either sensitize or activate mitochondrial apoptosis, serving as prototype cancer therapeutics," *Cancer Cell 2*:183-192 (2002).
Letai, "BH3 domains as BCL-2 inhibitors: prototype cancer therapeutics," *Expert Opin. Biol. Ther. 3*:293-304 (2003).
Letai et al., "Antiapoptotic BcL-2 is required for maintenance of a model leukemia," *Cancer Cell 6*:241-249 (2004).
Letai, "The BCL-2 network: Mechanistic insights and therapeutic potential," *Drug Disc. Today: Disease Mechanisms 2*(2):145-151 (2005).
Letai, "Perturbing cancer cell mitochondria to learn how to kill cancer with BH3 profiling," Broad Institute, Seminar Series on Cell Circuits and Epigenomics, Jul. 28, 2014, Presentation.
Li et al., "tsg 101: A Novel tumor susceptibility gene isolated by controlled Homozygous functional knockout of Allelic Loci in Mammalian Cells," *Cell 85*:319-329, 1996.

(56) References Cited

OTHER PUBLICATIONS

Li et al., "Cleavage of BID by Caspase 8 Mediates the Mitochondrial Damage in the Fas Pathway of Apoptosis," *Cell* 94(4):491-501 (1998).
Li et al., "Endonuclease G is an apoptotic Dnase when released from mitochondria," *Nature* 412:95-99 (2001).
Lin, K.H., et al., "Targeting MCL-1/BCL-XL Forestalls the Acquisition of Resistance to ABT-1999 in Acute Myeloid Leukemia", Scientific Reports, 6(1): 9 Pages 2016.
Lin et al., "Flavopiridol given as a 30-min intravenous (IV) bolus followed by 4-hr continuous IV infusion (CIVI) results in clinical activity and tumor lysis in refractory chronic lymphocytic leukemia (CLL)," *Journal of Clinical Oncology, 2004 ASCO Annual Meeting Proceedings (Post-Meeting Edition)* 22(14S):8564 (2004). (1 page).
Lin, et al., "Seventy-Two Hour Continuous Infusion Flavopiridol in Relapsed and Refractory Mantle Cell Lymphoma," *Leukemia & Lymphoma* 43:793-797 (2002).
Lin, T.S., et al., "Phase II Study of Flavopiridol in Relapsed Chronic Lymphocytic Leukemia Demonstrating High Response Rates in Genetically High-Risk Disease", Journal of Clinical Oncology, 27(35):6012-6018 (2009).
Lindsley, R.C., et al., "Acute Myeloid Leukemia Ontogeny is Defined by Distinct Somatic Mutations", Blood, 125(9):1367-1376 (2015).
Linenberger, K.J. and Bretz, S.L., "Biochemistry Students' Ideas About Shape and Charge in Enzyme-Substrate Interactions", Biochemistry and Molecularbiology Education, 203-212 (2014).
Litzow, M.R., et al., "A randomized trial of three novel regimens for recurrent acute myeloid leukemia deomonstrates the continuing challenge of treating this difficult disease", Am. J. of Hematol, 94(1), 111-117, Jan. 2019.
Liu, et al., "Bax Conformation Change is a Crucial Step for PUMA-Mediated Apoptosis in Human Leukemia," Biochemical and Biophysical Research Communications, 310:956-962 (2003).
Liu, et al., "BH3-Based Fusion Artificial Peptide Induces Apoptosis and Targets Human Colon Cancer," Molecular Therapy, 17:1509-1516 (2009).
Liu, et al., "CDKI-17, a Novel CDK9 Inhibitor, is Preferentially Cytotoxic to Cancer Cells Compared to Flavopiridol," Int. J. Cancer, 130:1216-1226 (2012).
Lonberg et al., "Antigen-specific human antibodies from mice comprising four distinct genetic modifications," *Nature* 368:856-859 (1994).
Londoño, et al., "A Reliable Method for Quantification of Splice Variants Using RT-qPCR", BMC Mol. Biol., 17(8):1-12 (2016).
Long et al., "Optimization and validation of mitochondria-based functional assay as a useful tool to identify BH3-like molecules selectively targeting anti-apoptotic Bcl-2 proteins," *BMC Biotechnol* 13:45 (2013).
Lovén et al., "Selective Inhibition of Tumor Oncogenes by Disruption of Super-Enhancers," *Cell* 153:320-334 (2013). (27 pages).
Lozanski et al., "Alemtuzumab is an effective therapy for chronic lymphocytic leukemia with p53 mutations and deletions," *Blood* 103:3278-3281 (2004).
Lu, H., et al., "Compensatory Induction of MYC Expression by Sustained CDK9 Inhibition via a BRD4-dependent Mechanism", eLife, 26 pages Jun. 17, 2015.
Luo et al., "Bid, a Bcl2 interacting protein, mediates cytochrome c release from mitochondria in response to activation of cell surface dell receptors," *Cell* 94(4):481-490 (1998).
Lutter et al., "The pro-apoptotic Bcl-2 family member tBid localizes to mitochondrial contact sites," *BMC Cell Biology* 2:22 (2001).
Malcovati et al., "Diagnosis and Treatment of Primary Myelodysplastic Syndromes in Adults: Recommendations From the European LeukemiaNet," Blood 122(17):2943-2964 (2013).
Malumbres, "Cyclin-dependent kinases," *Genome Biol.* 15(122):1-10 (2014).
Mann et al., "Cell cycle inhibition preserves endothelial function in genetically engineered rabbit vein grafts," *J. Clin. Invest.* 99(6):1295-1301 (1997).

Marani et al., "Identification of Novel Isoforms of the BH3 Domain Protein Bim which Directly Activate Bax to Trigger Apoptosis," *Mol. Cell. Biol.* 22(11):3577-3589 (2002).
Marks et al., "By-passing Immunization human Antibodies from v-gene libraries displayed on phage," *J. Mol. Biol.* 222:581 (1991).
Marks et al., "By-passing Immunization: building high affinity human antibodies by chin shuffling," *Bio/Technology* 10:779-783 (1992).
Martin, "Opening the Cellular Poison Cabinet," *Science* 330:1330-1331 (2010).
Mason, et al., "The Hypogonadal Mouse: Reproductive Functions Restored by Gene Therapy," Science, 234:1372-1378 (1986).
Matasushita, et al., "A High-Efficiency Protein Transduction System Demonstrating the Role of PKA in Long-Lasting Long-Term Potentiation," The Journal of Neuroscience, 21(16):6000-6007 (2001).
Matsumura, Y., et al., "1959-CDK9 Inhibition Combined with Hypomethylating Agents Target MCL-1 Dependency in MDS and AML", AACR Annual Meeting 2021—Virtual-Poster to be presented during Session PO.MCB06.01-Cell Cycle on Apr. 10, 2021, downloaded from AACR website, URL: https://www.abstractsonline.com/pp8/#!/9325/presentation/3238 on Mar. 30, 2021, 2 pages.
Matsuzaki, "Why and how are peptide-lipid interactions utilized for self-defense?" *Biochem. Soc. Transactions* 29:598-601 (2001).
Mayer, "Induction of apoptosis by flavopiridol unrelated to cell cycle arrest in germ cell tumour derived cell lines," Invest New Drugs 23(3):205-211 (2005).
McDonnell et al., "bcl-2-Immunoglobulin Transgenic Mice Demonstrate Extended B Cell Survival and Follicular Lymphoproliferation," *Cell* 57:79-88 (1989).
Means et al., "Modifications to change properties," in *Chemical Modification of Protein*, Chapter 3, pp. 35-54, Holden-Day (1974).
Mian, S.A., et al., "Splicesome Mutations Exhibit Specific Associations with Epigenetic Modifiers and Proto-Oncogenes Mutated in Myelodysplastic Syndrome", Haematologica, 98(7):1058-1066 (2013).
Mikhael et al., "Treatment of Multiple Myeloma: ASCO and CCO Joint Clinical Practice Guideline," J Clin Oncol 37(14):1228-1264, 2019. (40 pages).
Miller et al., "Therapeutic Strategies to Enhance the Anticancer Efficacy of Histone Deacetylase Inhibitors," *J. Biomed. Biotechnol.* 2011:17 pages (2011).
Milstein et al., "Hybrid hybridomas and their use in immunohistochemistry," *Nature* 305:537-539, 1983.
Mintz G.S., "In-stent restenosis: the Washington Hospital Center experience", Am. J. Cardiol., 81:7E-13E (1998).
Mintz G.S., "Arterial remodeling after coronary angioplasty: a serial intravascular ultrasound study", Circulation,; 94:35-43 (1996).
Mirguet, O., et al., "Discovery of Epigenetic Regulator I-BET762: Lease Optimization to Afford a Clinical Candidate Inhibitor of the BET Bromodomains", Journal of Medicinal Chemistry, 56:7501-7515 (2013).
Molassiotis et al., "Use of complementary and alternative medicine in cancer patients: A European survey," *Annals of Oncology* 16:655-663 (2005).
Montero, et al., "Drug-Induced Death Signaling Strategy Rapidly Predicts Cancer Response to Chemotherapy," Cell, 160:977-989 (2015).
Montesinos et al., "Tumor lysis syndrome in patients with acute myeloid leukemia: identification of risk factors and development of a predictive model," *Haematologica* 93(1):67-74, 2008.
Moore et al., "Chronic lymphocytic leukemia requires BCL2 to sequester prodeath BIM, explaining sensitivity to BCL2 antagonist ABT-737," *J. Clin. Invest.* 117(1):112-121 (2007).
Moore et al., "BH3 profiling—measuring integrated function of the mitochondrial apoptotic pathway to predict cell fate decisions," *Cancer Lett* 332:202-205 (2013). (10 pages).
Morishita et al., "A gene therapy strategy using a transcription factor decoy of the E2F binding site inhibits smooth muscle proliferation in vivo," *Proc. Natl. Acad. Sci. USA* 92:5855-5859 (1995).
Moros, et al., "Synergistic Antitumor Activity of Lenalidomide with the BET Bromodomain Inhibitor CPI203 in Bortezomib-Resistant Mantle Cell Lymphoma", Leukemia, 28(10):2049-2059 (2015).
Morrison et al., "Success in specification," *Nature* 368:812-813 (1994).

(56) References Cited

OTHER PUBLICATIONS

Motwani, M., et al., "Sequential Dependent Enhancement of Caspase Activation and Apoptosis by Flavopiridol on Paclitaxel-Treated Human Gastric and Breast Cancer Cells", Clinical Cancer Research, The American Association for Cancer Research, 5(7):1876-1883 (1996).
Motwani, M., et al., "Docetaxel and Navelbine Induced Apoptosis is Enhanced by Flavopiridol (Flavo) in Breast Cancer Cells and is Sequence Dependent", Proceedings of the American Association for Cancer Research, 41, p. 143, Abstract #912 (2000).
Muchmore, et al., "X-ray and NMR Structure of Human Bcl-XL, an Inhibitor of Programmed Cell Death," Nature, 381:335-341 (1996).
Murthi et al., "Structure-Activity Relationship Studies of Flavopiridol Analogues," Bioorganic & Medicinal Chemistry Letters 10:1037-1041 (2000).
Munson, et al., "Ligand: A Versatile Computerized Approach for Characterization of Ligand Binding Systems," Analytical Biochemistry, 107:220-239 (1980).
Nagai et al., "Studies on Psychotropic Agents. VI.[1]) Synthesis of 1'-Methylspiro[6-fluoroindan-1, 3'-pyrrolidine]-3-one and Related Compounds," Chem. Pharm. Bull. 28(5):1387-1393, 1980.
Naik et al., "An Antiinflammatory Cum Immunomodulatory Piperidinylbenzopyranone From *Dysoxylum Binectariferum*: Isolation, Structure and Total Synthesis," Tetrahedron 44:2081-2086 (1988).
Nakano et al., "PUMA, a Novel Proapoptotic Gene, Is Induced by p53," Molecular Cell 7:683-694 (2001).
Narita et al., "bax interacts with the permeability transition pore to induce permeability transition and cytochrome c release in isolated mitochondria," Proc. Natl. Acad. Sci. USA 95:14681-14686 (1998).
NCCN Clinical Practice Guidelines in Oncology (NCCN Guidelines®) Acute Myeloid Leukemia, Version 2.2014, NCCN.org, 6 pages.
NICE guidelines, "Myeloma: Diagnosis and Management," National Institute for Health and Care Excellence: 1-27 (2016).
Neuberger et al., "Generating high-avidity human Mabs in mice," Nature Biotechnology 14:826, 1996.
Nguyen et al., "Azacitidine and decitabine have different mechanisms of action in non-small cell lung cancer cell lines," Lung Cancer: Targets and Therapy 1:119-140 (2010).
Noel et al., "Abstract C244: Development of the BET bromodomain inhibitor OTX015," Molecular Cancer Therapeutics 12(11): Supplement, 2013.
O'Brien et al., "Proliferation in primary and restenotic coronary atherectomy tissue: implications for antiproliferative therapy," Circ. Res. 73(2):223-231, 1993.
O'Brien et al., "Phase I and II Multicenter Study of Oblimersen Sodium, a Bcl-2 Antisense Oligonucleotide, in Patients With Advanced Chronic Lymphocytic Leukemia," J. Clin. Oncol. 23(30):7697-7702 (2005).
O'Connor et al., "Bim: a novel member of the Bcl-2 family that promotes apoptosis," EMBO J 17(2):384-395 (1998).
Oda et al., "Noxa, a BH3-Only Member of the Bcl-2 Family and Candidate Mediator of p53-Induced Apoptosis," Science 288:1053-1058 (2000).
Odore et al., "A phase I pharmacokinetic study of OTX015 for the treatment of patients with hematologic malignancies," Cancer Research 74(Supplement 19):LB-231 (2014). (4 pages) (Abstract Only).
Oh et al., "Conformational Changes in BID, a Pro-apoptotic BCL-2 Family Member, upon Membrane Binding," J. Biol. Chem. 280(1):753-767 (2005).
Okamoto et al., "Increased antitumor potential of the raloxifene prodrug, raloxifene diphosphate," Int. J. Cancer 122:2142-2147, 2008.
Oken, et al., "Toxicity and Response Criteria of the Eastern Cooperative Oncology Group", Am. J. Clin. Oncol., 5(6):649-655 (1982).
Oltersdorf et al., "An inhibitor of Bcl-2 family proteins induces regression of solid tumours," Nature 435:677-681 (2005).
Opferman et al., "Development and maintenance of B and T lymphocytes requires antiapoptotic MCL-1," Nature 426:671-676 (2003).
Opferman et al., "Obligate Role of Anti-Apoptotic MCL-1 in the Survival of Hematopoietic Stem Cells," Science 307:1101-1104 (2005).
Oppermann et al., "High-content screening identifies kinase inhibitors that overcome venetoclax resistance in activated CLL cells," Blood 128(7):934-947 (2016).
Oscier et al., "Multivariate analysis of prognostic factors in CLL: clinical stage, IGVH gene mutational status, and loss or mutation of the p53 gene are independent prognostic factors," Blood 100:1177-1184 (2002).
Otsuka et al., "Effect of Polymorphic Forms of Bulk Powders on Pharmaceutical Properties of Carbamazepine Granules," Chem. Pharm. Bull. 47(6):852-856 (1999).
Pandit-Taskar, "Functional Imaging Methods for Assessment of Minimal Residual Disease in Multiple Myeloma: Current Status and Novel ImmunoPET Based Methods," Seminars in Hematology, 55(1):22-32 (2018).
Paoluzzi et al., "The BH3-only mimetic ABT-737 synergizes the antineoplastic activity of proteasome inhibitors in lymphoid malignancies," Blood 112:2906-2916, 2008.
Papaemmanuil et al., "Genomic Classification and Prognosis in Acute Myeloid Leukemia," The New England Journal of Medicine 374(23):2209-2221 (2016).
Paquin et al., "Design and synthesis of 4-[(s-triazin-2-ylamino)methyl]-N-(2-aminophenyl)-benzamides and their analogues as a novel class of histone deacetylase inhibitors," Bioorganic & Medicinal Chemistry Letters 18:1067-1071, 2008.
Park et al., "Inhibitors of cyclin-dependent kinases promote survival of post-mitotic neuronally differentiated PC12 cells and sympathetic neurons," J. Biol. Chem. 271(14):8161-8169, 1996.
Parker et al., "Early Induction of Apoptosis in Hematopoietic Cell Lines After Exposure to Flavopiridol," Blood 91:458-465 (1998).
Parovichnikova, E., et al., "The MRD-Negativity Rate Measured by Flow Cytometry After the 1st and 2nd Induction Course Among CR AML Patients from Different Cytogenetic Subgroups Does Not Differ Though the Morphological CR Achievement Does", Blood, 132(Suppl1:1495, 6 pages (2018).
Parry et al., "Dinaciclib (SCH 727965), a Novel and Potent Cyclin-Dependent Kinase Inhibitor," Molecular Cell Therapy 9:2344-2353 (2010).
Paruch et al., "Discovery of Dinaciclib (SCH 727965): A Potent and Selective Inhibitor of Cyclin-Dependent Kinases," ACS Medicinal Chemistry Letters 1:204-208 (2010).
Payne, et al., "Identification of the Regulatory Phorphorylation Sites in pp42/mitogen-activated Protein Kinase (MAP Kinase)", The EMBO Journal, 10(4):885-892 (1991).
Pepper et al., "Flavopiridol circumvents Bcl-2 family mediated inhibition of apoptosis and drug resistance in B-cell chronic lymphocytic leukaemia," Br. J. Haematol 114(1):70-77 (2001).
Perkins et al., "Frequency and Type of Serious Infections in Fludarabine-Refractory B-Cell Chronic Lymphocytic Leukemia and Small Lymphocytic Lymphoma," Cancer 94:2033-2039 (2002).
Perrot et al., "Minimal Residual Disease Negativity Using Deep Sequencing is a Major Prognostic Factor in Multiple Myeloma," Blood 132(23):2456-2464 (2018).
Phelps, et al., "Clinical Response and Pharmacokinetics from a Phase I Study of an Active Dosing Schedule of Flavopiridol in Relapsed Chronic Lymphocytic Leukemia", Blood, 113(12):2637-2645 (2009).
Phillips et al., "Loss in MCL-1 function sensitizes non-Hodgkin's lymphoma cell lines to the BCL-2-selective inhibitor venetoclax (ABT-199)," Blood Cancer J. 5:e368 (2015). (8 pages).
Picaud et al., "PFI-1, a Highly Selective Protein Interaction Inhibitor, Targeting BET Bromodomains," Cancer Research 73:3336-33346 (2013).
Picaud, et al., "RVX-208, an Inhibitor of BET Transcriptional Regulators with Selectivity for the Second Bromodomain", PNAS, 110(49):19754-19759 (2013).

(56) References Cited

OTHER PUBLICATIONS

Piekarz et al., "Inhibitor of histone deacetylation, depsipeptide (FR901228), in the treatment of peripheral and cutaneous T-cell lymphoma: a case report," *Blood*, 98:2865-2868 (2001).

Pierceall et al., "BH3 Profiling Discriminates Response to Cytarabine-Based Treatment of Acute Myelogenous Leukemia," *Mol. Cancer. Ther.*, 12(12):2940-2949 (2013).

Pierceall et al., "Mcl-1 Dependence Predicts Response to Vorinostat and Gemtuzumab Ozogamicin in Acute Myeloid Leukemia," *Leuk Res*, 38:564-568 (2014). (13 pages).

Pierceall et al., "Mitochondrial Priming of Chronic Lymphocytic Leukemia Patients Associates Bcl-$_{XL}$ Dependence with Alvocidib Response," *Leukemia*, 28:2251-2254 (2014). (7 pages).

Pinkert et al., "An albumin enhancer located 10 kb upstream functions along with its promoter to direct efficient, liver-specific expression in transgenic mice," *Genes and Dev*, 1:268-276 (1987).

Plumb et al., "Pharmacodynamic Response and Inhibition of Growth of Human Tumor Xenografts by the Novel Histone Deacetylase Inhibitor PXD101," *Molecular Cancer Therapeutics*, 2:721-728 (2003).

Pode-Shakked et al., "Development tumourigenesis: NCAM as a purative marker for the malignant renal stem/progenitor cell population," *J. Cell. Mol. Med.* 13(8b):1792-1808 (2009).

Polster et al., "BH3 Death Domain Peptide Induces Cell Type-selective Mitochondrial Outer Membrane Permeability," *The Journal of Biological Chemistry*, 276:37887-37894 (2001).

Presta, "Antibody engineering," *Curr. Op. Struct. Biol.*, 2:593-596 (1992).

Pritzker, "Cancer Biomarkers: Easier Said Than Done," *Clinical Chemistry*, 48:1147-1150 (2002).

Pugh, "Circulating Tumour DNA for Detecting Minimal Residual Disease in Multiple Myeloma," *Seminars in Hematology*, 55:38-40 (2018).

Putcha et al., "Induction of BIM, a Proapoptotic BH3-Only BCL-2 Family Member, Is Critical for Neuronal Aopotosis," *Neuron*, 29:615-628 (2001).

Puthalakath et al., "The Proapoptotic Activity of the Bcl-2 Family Member Bim is Regulated by Interaction with the Dynein Motor Complex," *Mol. Cell.*, 3:287-296 (1999).

Puthalakath et al., "Bmf: A Proapoptotic BH3-Only Protein Regulated by Interaction with the Myosin V Actin Motor Complex, Activated by Anoikis," *Science* 293:1829-1832 (2001).

Puthalakath et al., "Keeping killers on a tight leash: transcriptional and post-translational control of the pro-apoptotic activity of BH3-only proteins," *Cell Death Differ.*, 9:505-512 (2002).

Qi, et al., "A Subset of Small Cell Lunng Cancer (SCLC) Cell Lines is MCL-1-Dependent and Responds to Cyclin-Dependent Kinase (CDK)9 Inhibition in vitro and in vivo", *Cancer Research*, 72(8): Suppl. 1, Abstract 2016, 4 pages, (2012).

Quinsay, et al. "Pro-Apoptotic Bnip3 Mediates Permeabilization of Mitochondria and Release of Cytochrome c Via a Novel Mechanism," *Circulation*, 118:Abstract 1783 (S388)—5 pages (2008).

Raff, "Social controls on cell survival and cell death," *Nature*, 356:397-400 (1992).

Ramsey, H.E., et al., "A Novel MCL1 Inhibitor Combined with Venetoclax Rescues Venetoclax-Resistant Acute Myelogenous Leukemia", *Cancer Discov*, 8(12):1566-1581 (2018).

Rassenti et al., "ZAP-70 Compared with Immunoglobulin Heavy-Chain Gene Mutation Status as a predictor of Disease Progression in Chronic Lymphocytic Leukemia," *N. Engl. J. Med.*, 351:893-901 (2004).

Ravandi, et al., "Evaluating Measurable Residual Disease in Acute Myeloid Leukemia", *Blood Adv.*, 2(11):1356-1366 (2018).

Ray et al., "BNIP3 Heterodimerizes with Bcl-2/Bcl-xl and Induces Cell Death Independent of a Bcl-2 Homology 3 (BH3) Domain at Both Mitochondrial and Nonmitochondrial Sites," *J. Biol. Chem.*, 275(2):1439-1448 (2000).

Raychaudhuri, "Low probability Bid-Bax reaction generates heterogeneity in apoptosis resistance of cancer and cancer stem cells," arXiv:1108.2091 [q-bio.MN] (2011).

Ren et al., "BID, BIM, and PUMA Are Essential for Activation of the BAX- and BAK-Dependent Cell Death Program," *Science*, 330:1390-1393 (2010).

Rezaei et al., "Leukemia markers expression of peripheral blood vs. bone marrow blasts using flow cytometry," *Med Sci. Monit*, 9:CR359-CR362 (2003).

Richard, D.., et al,"Hydroxyquinoline-derived compounds and analoguing of selective Mcl-1 inhibitors using a functional biomarker" Bioorg Med Chem., 21(21):6642-9 (2013).

Richon et al., "A class of hybrid polar inducers of transformed cell differentiation inhibits histone deacetylases," *Proc. Natl. Acad. Sci. USA*, 95:3003-3007 (1998).

Riechmann et al., "Reshaping human antibodies for therapy," *Nature*, 332:323-327 (1988).

Rollins-Raval et al., "The value of immunohistochemistry for CD14, CD123, CD33, myeloperoxidase and CD68R in the diagnosis of acute and chronic myelomonocytic leukaemias," *Histopathology*, 60:933-942 (2012).

Rosenblatt, et al., "PD-1 Blockade by CT-011, Anti PD-1 Antibody, Enhances Ex-Vivo T Cell Responses to Autologous Dendritic/ Myeloma Fusion Vaccine", J. Immunother, 34(5):409-418 (2011).

Roshal, "Minimal Residual Disease Detection by Flow Cytometry in Multiple Myeloma: Why and How?" *Seminars in Hematology* 55(1):4-12 (2018).

Rothbard et al., "Conjugation of arinine oligomers to cyclosporine A facilitates topical delivery and inhibition of inflammation," *Nat. Med.*, 6(11):1253-1257 (2000).

Rudek et al., "Clinical Pharmacology of Flavopiridol Following a 72-Hour Continuous Infusion," *Ann Pharmacother*, 37:1369-1374 (2003).

Ruef et al., "Induction of vascular endothelial growth factor in balloon-injured baboon arteries," *Circ. Res.*, 81:24-33 (1997).

Ruef, J., "Induction of rat aortic smooth muscle cell growth by the lipid peroxidation product 4-hydroxy-2-nonenal," Circulation, 97:1071-1078 (1998).

Ruef et al., "Flavopiridol Inhibits Smooth Muscle Cell Proliferation In Vitro and Neointimal Formation In Vivo After Carotid Injury in the Rat," *Circulation*, 100(6):659-665 (1999).

Ryan et al., "Heightened mitochondrial priming is the basis for apoptotic hypersensitivity of CD4+ CD8+ thymocytes," *Proc. Natl. Acad. Sci USA*, 107(29):12895-12900 (2010).

Ryan et al., "BH3 Profiling in Whole Cells by Fluorimeter or FACS," *Methods*, 61:156-164 (2013). (22 pages).

Saito et al., "A synthetic inhibitor of histone deacetylase, MS-27-275, with marked in vivo antitumor activity against human tumors," *Proc. Natl. Acad. Sci. USA*, 96:4592-4597 (1999).

Salomon, C.J., et al., "Recent Developments in Chemical Deprotection of Ester Functional Groups", Tetrahedron, 49(18):3691-3748 (1993).

Samson et al., "A 35 amino acid fragment of leptin inhibits feeding in the rat," *Endocrinology*, 137:5182-5185 (1996).

San Miguel et al., "Early Immunophenotypical Evaluation of Minimal Residual Disease in Acute Myeloid Leukemia Identifies Different Patient Risk Groups and May Contribute to Postinduction Treatment Stratification," *Blood*, 98(6):1746-1751 (2001).

Sata et al., "Fas ligand gene transfer to the vessel wall inhibits neointima formation and overrides the adenovirus-mediated T cell response," *Proc. Natl. Acad. Sci. USA* 95:1213-1217 (1998).

Sattler et al., "Structure of Bxl-xl-Bak Peptide Complex: Recognition Between Regulators of Apoptosis," *Science* 275:983-986 (1997).

Sausville et al., "Inhibition of CDKs as a Therapeutic Modality," *Ann NY Acad of Sci* 910:207-222 (2000).

Schimmer et al., "The BH3 domain of BAD fused to the Antennapedia peptide induces apoptosis via its alpha helical structure and independent of Bcl-2," *Cell Death and Differentiation* 8:725-733 (2001).

Schuurhuis, et al., "Minimal/Measurable Residual Disease in Aml: A Consensus Document from the Duropean LeukemiaNet MRD Working Party", Blood, 131(12):1275-1291 (2018).

Schwartz et al., "The intima: soil for atherosclerosis and restenosis," *Circ. Res.*, 77:445-465 (1995).

Schwartz, G.K., et al., "Phase I Trial of Sequential Paclitaxel and Cisplatin in Combination with the Cyclin Dependent Kinase Inhibi-

(56) References Cited

OTHER PUBLICATIONS tor Flavopiridol (Flavo) in Patients with Advances Solid Tumors", Clinical Cancer Research, 5:3754s, Abstract #122 (1999).
Schwartz, et al, "Phase II Study of the Cyclin-Dependent Kinase Inhibitor Falvopiridol Administered to Patients with Advanced Gastric Carcinoma," J Clin Oncol, 19:1985-1992 (2001).
Score Search Results Details for U.S. Appl. No. 11/789,557 and Search Result Nov. 6, 2009_104627 . . . , downloaded from URL: http://es/ScoreAccessWeb/GetItem.action?AppID=11789557swqId=09323b6780cf451a&ItemN . . . , on Nov. 24, 2009—4 pages.
Seal et al., "Identification of a novel series of BET family bromodomain inhibitors: binding mode and profile of I-BET151 (GSK1210151A)," Bioorg. Med. Chem. Lett, 22:2968-2972 (2012).
Sedlacek et al., "Flavopiridol (L86 8275; NSC 649890), a new kinase inhibitor for tumor therapy," International Journal of Oncology, 9:1143-1168, 1996.
Sen et al., "Artemisinin triggers induction of cell-cycle arrest and apoptosis in Leishmania donovani promastigotes," J Med Microbiol, 56(Pt. 9):1213-1218 (2007).
Senderowicz et al., "Phase I Trial of Continuous Infusion Flavopiridol, a Novel Cyclin-Dependent Kinase Inhibitor, in Patients with Refractory Neoplasms," J. Clin Onc, 16:2986-2999 (1998).
Senderowicz, "Flavopiridol: the first cyclin-dependent kinase inhibitor in human clinical trials," Investigational New Drugs, 17:313-320 (1999).
Senderowicz et al., "Preclinical and Clinical Development of Cyclin-Dependent Kinase Modulators," J Natl Cancer Inst, 92:376-387 (2000).
Shalaby et al., "Development of humanized bispecific antibodies reactive with cytotoxic lymphocytes and tumor cells overexpressing the HER2 protooncogene," Exp. Med., 175:217-225 (1992).
Shangary et al., "Peptides derived from BH3 domains of Bcl-2 family members: a comparative analysis of inhibition of Bcl-2, Bcl-x(L) and Bax oligomerization, induction of cytochrome c release, and activation of cell death," Biochemistry, 41:9485-9495 (2002).
Shapiro et al., "A Phase II Trial of the Cyclin-dependent Kinase Inhibitor Flavopiridol in Patients with Previously Untreated Stage IV Non-Small Cell Lung Cancer," Clinical Cancer Research 7:1590-1599 (2001).
Shibue et al., "Differential contribution of Puma and Noxa in dual regulation of p53-mediated apoptotic pathways," The EMBO Journal, 25:4952-4962 (2006).
Shimizu et al., "Proapoptotic BH3-only Bcl-2 family members induce cytochrome c release, but not mitochondrial membrane potential loss, and do not directly modulate voltage-dependent anion channel activity," PNAS, 97:577-582 (2000).
Shopes, "A genetically engineered human IgG mutant with enhanced cytolytic activity," J. Immunol, 148:2918-2922 (1992).
Sinicrope et al., "Proapoptotic Bad and Bid Protein Expression Predict Survival in Stages II and III Colon Cancers," Clin. Canc. Res., 14(13):4128-4133, 2008.
Sinicrope et al., "Prognostic Impact of Bim, Puma, and Noxa Expression in Human Colon Carcinomas," Clin. Canc. Res., 14(18):5810-5818, 2008.
Sirois et al., "Antisense oligonucleotide inhibition of PDGFR-beta receptor subunit expression directs suppression of intimal thickening," Circulation 95:669-676 (1997).
Smith, D. B., et al., "An Alvocidib-Containing Regimen is Highly Effective in AML Patients Through a Mechanism Dependent on MCL1 Expression and Function," J. Clin. Oncol, 33: abstract 7062, 3 pages (2015).
Smith, et al, "Enhancer Biology and Enhanceropathies," Nature Stuctural & Molecular Biology, 21(3):210-219 (2014).
Smith, et al., "Real-World Outcomes Among AML Patients Treated with Decitabine or Azacitidine", Hematologica, 98(s1): 19 (2013 (From the 18th Congress of the European Hematology Association, Stockholm, Sweden, Jun. 13-16, 2013, Abstract No. p. 047).
Soltow et al., "Overexpression of CuZnSOD or MnSOD protects satellite cells from doxorubicin-induced apoptosis," FASEB J 21:A449 (2007)—Abstract.
Song, et al., "Application of Flavopiridol, Novel Small Molecule Cyclin-Dependent Kinase Inhibitor in Tumor Therapy", National Medical Journal of China, 85(12):862-864 (2005)—With English Translation of 10 pages.
Song, et al., "Carbon Monoxide Promotes Fas/CD9-Induced Apoptosis in Jurkat Cells," The Journal of Biological Chemisry, 279(43):44327-44334 (2004).
Song et al., "Additions and Correction, Carbon Monoxide Promotes Fas/CD95-induced Apoptosis in Jurkat Cells," The Journal of Biological Chemistry 280(23):22555-22556 (2005). (3 pages).
Stephens, D.M., et al., "Cyclophosphamide, Alvocidib (Flavorpiridol), and Rituximab, a Novel Feasible Chemoimmunotherapy Regimen for Patients with High-Risk Chronic Lymphocytic Leukemia", Leukemia Research, 37:1195-1199 (2013).
Stevenson et al., "A chimeric antibody with dual Fc regions (bisFabFc) prepared by manipulations at IgG hinge," Anti-Cancer Drug Design 3:219-230 (1989).
Stewart et al., "The MCL-1 BH3 Helix is an Exclusive MCL-1 inhibitor and Apoptosis Sensitizer," Nat. Chem. Biol. 6(8):595-601 (2010).
Sturm et al., "Mutation of p53 and consecutive selective drug resistance in B-CLL occurs as a consequence of prior DNA-damaging chemotherapy," Cell Death and Differentiation 10:477-484 (2003).
Sugiyama et al., "Activation of mitochondrial voltage-dependent anion channel by a pro-apoptotic BH3-only protein Bim," Oncogene 21(32):4944-4956 (2002).
Suzuki et al., "Possible Existence of Common Internalization Mechanisms among Arginine-rich Peptides," J. Biol Chem 277:2437-2443 (2002).
Szabo, C., "Understanding What Causes Relapse in Patients with Acute Myeloid Leukemia", Sep. 8, 2015, 3 pages. URL:https://www.pharmacytimes.com/ajax/understanding-what-cause-relpase-in-ptients-with-acute-myeloid-leukemia.
Tahir et al., "Potential mechanisms of resistance to venetoclax and strategies to circumvent it," BMC Cancer 17:399, 2017. (10 pages).
Tan et al., "Phase I Clinical and Parmacokinetic Study of Flavopiridol Administered as a Daily 1-Hour Infusion in Patients with Advanced Neoplasms," J Clin Oncol 20:4074-4082 (2002).
Tan, et al., "The DNA Methyltransferase Inhibitor Zebularine Induces Mitochondria-Mediated Apoptosis in Gastric Cells in Vitro and in Vivo", Biochemical and Biophysical Research Communications, 430:250-255 (2013).
Tanaka, et al., "Design and Characterization of Bivalent BET Inhibitors", Nat. Chem. Biol., 12(12):1089-1096 (2016).
Taussig et al., "Anti-CD38 antibody-mediated clearance of human repopulating cells masks the heterogeneity of leukemia-initiating cells," Blood 112(3):568-575, 2008.
Terradillos et al., "Direct addition of BimL to mitochondria does not lead to cytochrome c release," FEBS Lett, 522(1-3):29-34 (2002).
Terwijn et al., "High Prognostic Impact of Flow Cytometric Minimal Residual Disease Detection in Acute Myeloid Leukemia: Data From the HOVON/SAKK AML 42A Study," J Clin Oncol, 31(31):3889-3897 (2013).
Theisen et al., "Reversible inhibition of lysine specific demethylase 1 is a novel anti-tumor strategy for poorly differentiated endometrial carcinoma," BMC Cancer, 14:752 (2014).
Thomas, et al., "Phase I Clinical and Pharmacokinetic Trial Flavopiridol," Abstract #1496—Proceeding of the Annual Meeting of the American Association of Cancer Research, 38(14):222 (Mar. 1997).
Thomas et al., "Phase I clinical pharmacokinetic trial of the cyclin-dependent kinase inhibitor flavopiridol," Cancer Chemother Pharmacol, 50:465-472 (2002).
Thomenius et al., "Using BH3 Profiling as a Predictive Indicator for Myeloma Patient Response to Bortezomib," Blood 118(21): Abstract No. 3952 (2011).
Thoren, "Mass Spectrometry Methods for Detecting Monoclonal Immunoglobulins in Multiple Myeloma Minimal Residual Disease," Seminars in Hematology, 55(1):41-43 (2018).

(56) References Cited

OTHER PUBLICATIONS

Thornton et al., "High dose methyl prednisolone can induce remissions in CLL patients with p53 abnormalities," *Ann Hematol*, 82:759-765 (2003).
Thornton et al., "Characterisation of TP53 abnormalities in chronic lymphocytic leukaemia," *The Hematology Journa,l* 5:47-54 (2004).
Tolero Pharmaceuticals, "Making Meaningful Medicines," presented at the Jeffereies 2016 Healthcare Conference, New York, NY Jun. 7-10, 2016, 31 pages.
Toogood et al., "Discovery of a Potent and Selective Inhibitor of Cyclin-Dependent Kinase 4/6," *J. Med. Chem.* 48:2388-2406 (2005).
Touzeau et al., "BH3 profiling identifies heterogeneous dependency on Bcl-2 family members in multiple myeloma and predicts sensitivity to BH3 mimetics," *Leukemia* 30:761-764 (2016).
Traunecker et al., "Bispecific single chain molecules (Janusins) target cytotoxic lymphocytes on HIV infected cells," *EMBO J* 10:3655-3659 (1991).
Tsao et al., "Concomitant inhibition of DNA methyltransferase and BCL-2 protein function synergistically induce mitochondrial apoptosis in acute myelogenous leukemia cells," *Ann Hematol* 91(12):1861-1870 (2012).
Tutt et al., "Trispecific F(ab')3 derivatives that use cooperative signaling via the TCR/CD3 complex and CD2 to activate and redirect resting cytotoxic T cells," *J. Immunol* 147:60 (1991).
U.S. National Library of Medicine, "A Phase 1 Study Evaluating CPI-0610 in Patients with Progressive Lymphoma", ClinicalTrials.gov, Identifier, NCT01949883 First Posted Sep. 24, 2013, Last Update Posted Sep. 26, 2013, retrieved from https://clinicaltrials.gov/ct2/history/NCT0194883?a=2&b=2&c=merged#StudyPageTop, 7 pages.
U.S. National Library of Medicine, "Flavopiridol in Treating Patients With Previously Treated Chronic Lymphocytic Leukemia or Lymphocytic Lymphoma," Apr. 9, 2003, URL=https://www.clinicaltrials.gov/ct2/show/NCT00058240?term=alvocidib&rank=16, retrieved Dec. 11, 2018, 10 pages.
U.S. National Library of Medicine, "Flavopiridol in Treating Patients With Relapsed or Refractory Lymphoma or Multiple Myeloma," Jun. 3, 2005, URL=https://www.clinicaltrials.gov/ct2/show/study/NCT00112723?term-alvocidib&rank=8, retrieved Dec. 11, 2018, 14 pages.
U.S. National Library of Medicine, "Ph I Study of Alvocidib and Cytarabine/Daunorubicin (7+3) in Patients with Newly Diagnosed Acute Myeloid Leukemia (AML)", ClinicalTrials.gov, Identifier, NCT03298984, First Posted Oct. 2, 2017, Last Update Posted Mar. 14, 2019, retrieved from https://clinicaltrials.gov/ct2/show/study/NCT03298984, 8 pages.
U.S. National Library of Medicine, "Alvocidib, Cytarabine, and Mitoxantrone in Treating Patients with Newly Diagnosed Acute Myeloid Leukemia", ClinicalTrials. gov Identifier: NCT00795002 First Posted Nov. 21, 2008, Last Update Posted Aug. 7, 2018, retrieved from https://clinicaltrials.gov/ct2/show/NCT00795002, 11 pages.
Valencia et al., "A new reliable fluorescence in situ hybridization method for identifying multiple specific cytogenetic abnormalities in acute myeloid leukemia," *Leukemia & Lymphoma* 51(4):680-685 (2010).
Venkatesh, S. and Lipper, R.A., "Role of the Development Scientist in Compound Lead Selection and Optimization", Journal of Pharmaceutical Sciences, 89(2):145-154 (2000).
Vaquero et al., "Extracellular matrix proteins protect pancreatic cancer cells from death via mitochondrial and nonmitochondrial pathways," *Gastroenterology* 125(4):1188-1202 (2003).
Vaux et al., "Bcl-2 gene promotes haemopoietic cell survival and cooperates with c-myc to immortalize pre-B cells," *Nature* 335(6189):440-442 (1988).
Venkat, "Flavopiridol: A Drug that May Save Lives," 2004, retrieved from https://web.archive.org/web/20060615112217/http://clltopics.org/Chemo/flavopiridol.htm, 7 pages.
Venugopal et al., "A Phase I Study of Quisinostat (JMJ-26481585), an Oral Hydroxamate Histone Deacetylase Inhibitor with Evidence of Target Modulation and Antitumor Activity, in Patients with Advanced Solid Tumors," *Clinical Cancer Research* 19:4262-4272 (2013).
Verhoeyen et al., "Reshaping Human Antibodies: Grafting an Antilysozyme Activity," *Science* 239:1534-1536 (1988).
Ververis et al., "Histone deacetylase inhibitors (HDACIs): multitargeted anticancer agents," *Biologics: Targets and Therapy* 7:47-60 (2013).
Villela et al., "Acute Myeloid Leukaemia: Optimal Management and Recent Developments," *Drugs* 71(12):1537-1550 (2011).
Vitetta et al., "Redesigning Nature's Poisons to Create Anti-Tumor Reagents," *Science* 238:1098-1104 (1987).
Vives et al., "A Truncated HIV-1 Tat Protein Basic Domain Rapidly Translocates through the Plasma Membrane and Accumulates in the Cell Nucleus," *J. Biol. Chem.* 272(25):16010-16017 (1997).
Vo, "Mitochondrial Priming Determines Chemotherapeutic Response in Acute Myeloid Leukemia," Dissertation, Harvard University, 119 pages, Apr. 5, 2012.
Vo et al., "Relative Mitochondrial Priming of Myeloblasts and Normal HSCs Determines Chemotherapeutic Success in AML," *Cell* 151:344-355 (2012).
Waldschmidt et al., "Comprehensive Characterization of Circulating and Bone Marrow-Derived Multiple Myeloma Cells at Minimal Residual Disease," *Seminars in Hematology* 55(1):33-37 (2018).
Wang et al., "Bid: A Novel BH3 Domain-Only Death Agonist," *Genes & Development* 10(22):2859-2869, 1996.
Wang et al., "Cell Permeable Bcl-2 binding peptides: A Chemical Approach to Apoptosis Induction in Tumor Cells," *Cancer Res.* 60:1498-1502 (2000).
Wang et al., "Structure based discovery of an organic compound that binds Bcl-2 protein and induces apoptosis of tumor cells," *PNAS* 97:7124-7129 (2000).
Wang, "The Expanding Role of Mitochondria in Apoptosis," *Genes Dev* 15:2922-2933 (2001).
Wang et al., "Synthesis of pochoxime prodrugs as potent HSP90 inhibitors," *Bioorganic & Medicinal Chemistry Letters* 19:3836-3840 (2009).
Wei G. L., et al., "Temporally and spatially coordinated expression of cell cycle regulatory factors after angioplasty", Circ. Res., 80:418-426 (1997).
Wei et al., "tBID, a membrane-targeted death ligand, oligomerizes BAK to release cytochrome c," *Genes & Development* 14:2060-2071 (2000).
Wei et al., "Proapoptotic BAX and BAK: A Requisite Gateway to Mitochondrial Dysfunction and Death," *Science* 292(5517):727-730 (2001).
Weinstein et al., "Addiction to Oncogenes—the Achilles Heal to Cancer," *Science* 297:63-64 (2002).
Weniger et al., "Treatment-Induced Oxidative Stress and Cellular Antioxidant Capacity Determine Response to Bortezomib in Mantle Cell Lymphoma," *Clin. Cancer Res.* 17(15):5101-5112 (2011).
Werner et al., "Bcl-2 Family Member Bfl-1/A1 Sequesters Truncated Bid to Inhibit its Collaboration With Pro-Apoptotic Bak or Bax," *J. Biol. Chem* 277(25):22781-22788 (2002).
Westerhoff et al., "Magainins and the disruption of membrane-linked free-energy transduction," *Proc. Natl. Acad. Sci USA* 86(17):6597-6601 (1989).
Whatcott et al., "Alvocidib Potentiates the Activity of Venetoclax in Preclinical Models of Acute Myeloid Leukemia," *Blood* 128(22):1652 (2016).
Wilkinson, "Immunochemical techniques inspire development of new antibody purification methods," *The Scientist* 14(8):25-28 (2000).
Willis et al., "Proapoptotic Bak is sequestered by Mcl-1 and Bcl-XL, but not Bcl-2, until displaced by BH3-only proteins," *Genes Dev.* 19:1294-1305 (2005).
Willis et al., "Apoptosis Initiated When BH3 Ligands Engage Multiple Bcl-2 Homologs, not Bax or Bak," *Science* 315:856-859 (2007).
Wolff, M.E., "9 Some Considerations for Prodrug Design" in Burger's Medicinal Chemistry and Drug Discovery, Fifth Edition, vol. 1: Principles and Practice, Wolff, Manfred ed. (NY:Wiley & Sons) pp. 975-977 (1997).

(56) References Cited

OTHER PUBLICATIONS

Wolff et al., "Monoclonal antibody homodimers: Enhanced antitumor activity in Nude Mice," *Cancer Research* 53:2560-2565, 1993.
Wolter, et al. "Movement of Bax from the Cytosol to Mitochondria During Apoptosis," The Journal of Cell Biology, 139(5):1281-1292 (1997).
Worland et al., "Alteration of the Phosphorylation State of p34cdc2 Kinase by the Flavone L86-8275 in Breast Carcinoma Cells: Correlation with Decreased H1 Kinase Activity," *Biochem. Pharmacol* 46:1831-1840, 1993.
Woyach et al., "Targeted therapies in CLL: mechanisms of resistance and strategies for management," *Blood* 126:471-477 (2015).
Wyatt et al., "Identification of N-(4-Piperidinyl)-4-(2,6-dichlorobenzoylamino)-1H-pyrazole-3-carboxamide (AT7519), a Novel Cyclin Dependent Kinase Inhibitor Using Fragment-Based X-Ray Crysallography and Structure Based Drug Design," *J. Med. Chem.* 51:4986-4999, 2008.
Xiang et al., "Mcl1 haploinsufficiency protects mice from Myc-induced Acute Myeloid Leukemia," *J Clin Invest.*, 120(6):2109-2118 (2010).
Yamaguchi et al., "Bcl-XL Protects BimEL-induced Bax Conformational Change and Cytochrome c Release Independent of Interacting with Bax or BimEL," *J. Biol. Chem* 277(44):41604-41612 (2002).
Yamauchi, "Incorporation of novel agents into the treatment for acute myeloid leukemia," *Rinsho Ketsueki* 59(10):1988-1996 (2018). (English Abstract Only).
Yanagisawa, et al., "Translating Leukemia Stem Cells into the Clinical Setting: Harmonizing the Heterogeneity", Experimental Hematology, 44(12):1130-1137 (2016).
Yancey, D., et al., "BAD Dephosphorylation and Decreased Expression of MCL-1 Induce Rapid Apoptosis in Prostate Cancer Cells", PLOS One, 8(9):e74561, 11 pages (2013).
Yang et al., "Calculation of Protein Conformation from Circular Dichroism," *Methods Enzymol* 130:208-269, 1986.
Yang et al., "Bone marrow stroma-mediated resistance to FLT3 inhibitors in FLT3-ITD AML is mediated by persistent activation of extracellular regulated kinase," *British Journal of Haematology* 164:61-72 (2014).
Yang, et al. "Bad, a Heterodimeric Partner for Bcl-$_{XL}$ and Bcl-2, Displaces Bax and Promotes Cell Death," Cell, 80:285-291 (1995).
Yang, et al. "A Novel Liposomal Formulation of Flavopiridol," International Journal of Phamaceutics, 365:170-174 (2009).
Yasuda et al., "BNIP3α: A Human Homolog of Mitochondrial Proapoptotic protein BNIP3," *Cancer Res.* 59:533-537 (1999).
Yeh et al., "Up-regulation of CDK9 kinase activity and Mcl-1 stability contributes to the acquired resistance to cyclin-dependent kinase inhibitors in leukemia," *Oncotarget* 6(5):2667-2679 (2014).
Yi et al., "Inhibition of Bid-induced apoptosis by Bcl-2. tBid insertion, Bax translocation, and Bax/Bak oligomerization suppressed," *J. Biol. Chem.* 278(19):16992-16999 (2003).
Yoshimoto, et al., "FLT3-ITD Up-Regulates MCL-1 to Promote Survival of Stem Cells in Acute Myeloid Leukemia Via FLT3-ITD-Specific STAT5 Activation", Blood, 114(24):5034-5043 (2009).
Yu et al., "Catalytic Site Remodeling of the DOT1L Methyltransferase by Selective Inhibitors," *Nat Commun* 3:1288 (2012).
Zeidner et al., "Randomized multicenter phase II study of flavopiridol (alvocidib), cytarabine, and mitoxantrone (FLAM) versus cytarabine/daunorubicin (7+3) in newly diagnosed acute myeloid leukemia," Haematologica 100(9):1172-1179 (2015).
Zeidner, et al., "Randomized Phase II Trial of Timed-Sequential Therapy (TST) with Flavopirodol (Alvocidib), Ara-C and Mitoxantrone (FLAM) Versus "7+3" for Adults Ages 70 Year and Under with Newly Diagnosed Acute Myeloid Leukemia (AML)", Blood, 120(21): Abstract 47; 5 pages (2012).
Zeidener, J.F. and Karp, J.E., "Clinical Activity of Alvocidib (Flavopiridol) in Acute Myeloid Leukemia", Leukemia Research, 39:1312-1318 (2015).
Zeidner, J.F., et al., "Phase II Study Incorporating a Novel BH3-Profiling Biomarker Approach of Alvocidib Followed by Cytarabine and Mitoxantrone in Relapsed/Refractory Acute Myeloid Leukemia (AML)", Abstract PF243, 23rd European Hematology Association Congress, Stockholm Sweden Jun. 14-17, 2018.
Zeidner, J.F., et al., "Zella201: A Biomarker-Guided Phase II Study of Alvocidib Followed by Cytarabine and Mitoxantrone in MCL-1 Dependent Relapsed/Refractory Acute Myeloid Leukemia (AML)", Blood, 132(Suppl 1):6 pages (2018) (Abstract only).
Zeidner, J.F., et al., "Final Results of a Randomized Multicenter Phase II Study of Alvocidib, Cytarabine, and Mitoxantrone Versus Cytarabine and Daunorubicin (7+3) in Newly Diagnosed High-Risk Acute Myeloid Leukemia (AML)", Leukemia Research, 72:92-95 (2018).
Zeidner, J.F., et al., "Phase I Study of Alvocidib Followed by 7+3 (Cytarabine + Daunorubicin) in Newly Diagnosed Acute Myeloid Leukemia", Clin Cancer Res, 27:60-69 (2021).
Zeng et al., "Targeting the leukemia microenvironment by CXCR4 inhibition overcomes resistance to kinase inhibitors and chemotherapy in AML," *Blood* 113:6215-6224 (2009).
Zha, et al. "BH3 Domain of BAD is Required for Heterodimerization with BCL-XL and Proapoptotic Activity," The Journal of Biological Chemistry, 272(39):24101-24104 (1997).
Zha et al., "Serine Phosphorylation of Death Agonist BAD in Response to Survival Factor Results in Binding to 14-3-3 Not BCL-XL," *Cell* 87:619-628, 1996.
Zha, et al. "Posttranslational N-Myristoylation of BID as a Molecular Switch for Targeting Mitochondria and Apoptosis," Science, 290:1761-1765 (2000).
Zhai et al., "Clinical pharmacology and pharmacogenetics of flavopiridol 1-h i.v. infusion in patients with refractory neoplasms," *Anti-Cancer Drugs* 14:125-135 (2003).
Zhang et al., "Bcl-2 family proteins are essential for platelet survival," *Cell Death Differ.* 14(5):943-951 (2007).
Zhao et al., "The Making of I-BET762, a BET Bromodomain Inhibitor Now in Clinical Development," *Journal of Medicinal Chemistry* 56:7498-7500 (2013).
Zhao, et al., "BCL2 Amplicon Loss and Transcriptional Remodeling Drives ABT-199 Resistance in B Cell Lymphoma Models", Cancer Cell, 35:752-766 (2019).
Zhou, et al., "Novel Mutant-Selective EGFR Kinase Inhibitors Against EGFR T790M," Nature, 462(7276):1070-1074 (2009).
Zhou et al., "Flavopiridol enhances ABT-199 sensitivity in unfavourable-risk multiple myeloma cells in vitro and in vivo," *Br. J. Cancer* 118(3):388-397 (2018).
Zhu, et al., "Development of Venetoclax for Therapy of Lymphoid Malignancies", Drug Des. Devel. Ther., 11:685-694 (2017).
Zong et al., "BH3-only proteins that bind pro-survival Bcl-2 family members fail to induce apoptosis in the absence of Bax and Bak," *Genes & Development* 15:1481-1486 (2001).
Beesley, A.H. et al., "Comparative drug screening in NUT midline carcinoma," British Journal of Cancer, vol. 110; 1189-1198 (2014).
Byrn, S. et al., "Pharmaceutical Solids: A Strategic Approach to Regulatory Considerations," Pharmaceutical Research, vol. 12; No. 7; 10 pages (1995).
Caira, M.R., "Crystalline Polymorphism of Organic Compounds," Topics in Current Chemistry, vol. 198; Springer Verlag; 46 pages (1998).
Decker, R.H. et al., "The cyclin-dependent kinase inhibitor flavopiridol induces apoptosis in human leukemia cells (U937) through the mitochondrial rather than the receptor-mediated pathway," Cell Death and Differentiation, vol. 8; 715-724 (2001).
DiNardo, C.D. and Cortes, J.E., "New Treatment for Acute Myelogenous Leukemai", Expert Opin. Pharmacother, 16(1):95-106 (2015).
Forostyan, T.V., et al., "Abstract C081: Targeting CDK9 and MCL1 in Castration—Sensitive and Resistant Prostate Cancer Models", as present at AACR-NCI-EORTC International Conference on Molecular Targets and Cancer Therapeutiics, Oct. 26-30, 2019, Boston, MA, Molecular Cancer Therapeutic, 18(12):Supplement, 4 pages (2019).
George B, et al., "A Phase I, First-in-human, Open-label, Dose escalation, Safety, Pharmacokinetic, and Pharmacodynamic Study of Oral TP-1287 Administered Daily to Patients with Advanced Solid Tumors," American Society of Clinical Oncology—56th Annual Meeting. 2020, poster, 1 page.

(56) References Cited

OTHER PUBLICATIONS

Glossary of medical education terms, Institute of International Medical Education, URL: http://www.iime.org/glossart.htm, accessed Mar. 2013.
Gomez, L. et al., "Sequential combination of flavopiridol and docetaxel reduces the levels of X-linked inhibitor of apoptosis and AKT proteins and stimulates apoptosis in human LNCaP prostate cancer cells," Molecular Cancer, vol. 5; No. 5; 1216-1226 (2006).
Gordon, V. et al., "CDK9 Regulated AR Promoter Selectivity and Cell Growth through Serine 81 Phosphorylation," Molecular Endocrinology, vol. 24; 2267-2280 (2010).
Hilfiker, R. et al., "Relevance of Solid-State Properties for Pharmaceutical Products," Polymorphism: In the Pharmaceutical Industry, Wiley-VCH; Chapter 1; 19 pages (2006).
Karpinski, P.H., "Polymorphism of Active Pharmaceutical Ingredients," Chem. Eng. Technol., vol. 29; No. 2; 233-237 (2006).
Kim, W. et al., "Abstract 5133: TP-1287, an oral prodrug of the cyclin-dependent kinase-9 inhibitor alvocidib," Cancer Res, vol. 77; 13 Suppl; 2 pages; 5133 (2017).
Lee, D., et al., "Abstract PF285: Zella 101:Phase I Study of Alvocidib Followed by 7+3 Induction in Newly Diagnosed AML Patients" European Hematology Association 24th Annual Congress, Poster (2019).
Lee, D., et al., "Abstract PF285: Zella 101: Phase I Study of Alvocidib Followed by 7+3 Induction in Newly Diagnosed AML Patients" as present during the 24th Annual Congress of the European Hematology Association 2019, HemaSphere, 3:S1: 94 (2019).
Leverson et al., "Potent and selective small-molecule MCL-1 inhibitors demonstrate on-target cancer cell killing activity as single agents and in combination with ABT-263 (navitoclax)", Cell Death and Disease, vol. 6, No. 1, Jan. 15, 2015, p. e1590.
Lin, C.Y., et al., "Transcriptional Amplification in Turmor Cells with Elevated c-Myc", Cell, 151:56-67 (2012).
Matsumura Y et al., "CDK9 Inhibition Combined with Hypomethylating Agents Target MCL-1 Dependency in MDS and AML," American Association for Cancer Research—112th Annual Meeting, Poster, 2021.
Matsumura, Y., et al., "Pharmacodynamic Biomarker Strategies for CDK9 Inhibition" Poster as presented at Annual Meeting of the American Associateion for Cancer Research 2020; Apr. 27-28 and Jun. 22-24, 2020 in Philadelphia, PA, 1 page.
Matsumura, Y., et al., "Abstract 5813: Pharmacodynamic Biomarker Strategies for CDK9 Inhibition" as presented Annual Meeting of the American Association for Cancer Research 2020; Apr. 27-28 and Jun. 22-24, 2020 in Philadelphia, PA, Cancer Res., 80(Supplement 16):4 pages.
Morita, Y., et al., "Phase 1 Study of Alvocidib (DSP-2033) in Combination with Cytarabine/Mitoxantrone (ACM) or Cytarabine/Daunorubicin (A=7+3) in Japanese Patients (pts) with Acute Myeloid Leukemia (AML)", Blood, 136(Supplement 1):4 pages (2020).
Morita, Y. et al., "Phase 1 Study of Alvocidib (DSP-2033) in Combination with Cytarabine/Mitoxantrone (ACM) or Cytarabine/Daunorubicin (A+7+3) in Japanese Patients (Pts) with Acute Myeloid Leukemia (AML)," American Society of Hematology—62nd Annual Meeting. 2020.
Nathwani, S. et al., "Novel microtubule-targeting agents, pyrrolo-1,5-benzoxazepines, induce cell cycle arrest and apoptosis in prostate cancer cells," Oncology Reports, vol. 24; 1499-1507 (2010).
Quinsay, et al., "Bnip3 Mediates Permeabilization of Mitochondria and Release of Cytochrome c Via a Novel Mechanism," J Mol Cell Cardiol, 48(6):1146-1156 (2010).
Ranganathan, P. et al., "Preclinical activity of a novel CRM1 inhibitor in acute myeloid leukemia," Blood, vol. 120; No. 9; 1765-1773 (2012).
Riabov, V., et al., "Preclinical Assessment of Alvocidib in Combination with 5-Azacytidine in High-Risk Myelodysplastic Syndromes", Blood, 138(Supplement 1):4649 (2021).

Schwartz, G.K., et al., "Phase I Study of the Cyclin-Dependent Kinase Inhibitor flavopiridol in combination with Paclitaxel in Patients with Advanced Solid Tumors", Journal of Clinical Oncology, 20(8) Apr. 15, 2002: pp. 2157-2170.
Sommakia, S., et al., "Alvocidib Synergizes with BRD4 Inhibitors to Improve Cytotoxity in an AML Cell Line" Poster p. 255 presented at AACR-NCI-EORTC Virtual International Conference on Molecular Targets and Cancer Therapeutics, Oct. 7-10, 2021.
Tefferi, A. and Vardiman, J.W., "Mechanics of Disease: Myelodysplastic Syndromes," The New England Journal of Medicine, vol. 361; 1872-1885 (2009).
Tibes, R. and Bogenberger, J.M., "Transcriptional Silencing of MCL-1 Through Cyclin-Dependent Kinase Inhibition in Acute Myeloid Leukemia", Frontiers in Oncoogy, 9:Article 1205, 13 pages (2019).
Use of a novel small molecule cyclin inhibitor flavopiridol in tumor therapy, Natl Med J China, vol. 85, No. 12, pp. 862-864 (2005).
Vogelzang, N.J., et al., "Phase I, first-in-human, dose-expansion study of oral TP-1287, a cyclin-dependent kinase 9 (CDK9) inhibitor, in patients with advanced solid tumors (ASTs)", Poster presented at the annual meeting of the American Association for Cancer Research, New Orleans, Louisiana, Apr. 8-13, 2022.
Wagner, A.J., et al., "Phase 1, first-in-human, dose-expansion study of oral TP-1287, a cyclin-dependent kinase 9 (CDK9) inhibitor, in patients with sarcoma", Poster presented at the American Association for Cancer Research (AACR): Special Conference on Sarcomas | May 9-12, 2022; Montreal, Quebec, Canada.
Zalazar, F. et al., "Abstract 2340: CPS49 and Flavopiridol: A new selective drug combination for advanced prostate cancer," Cancer Res, vol. 72; Supplement 8; 2 pages (2012).
Zeidner, J.F., et al., "Zella-101: Phase 1 Study of Alvocidib Followed by 7+3 Induction in Newly Diagnosed AML Patients," Poster as presented at European Hematology Association, 25th Congress held virtually Jun. 11-21, 2020, 1 page.
Zeidner, J.F., et al., "Zella 201: A Biomarker-Guided Phase II Study of Alvocidib Followed by Cytarabine and Mitoxantrone in MCL-1 Dependent Acute Myeloid Leukemia (AML): Results of Newly Diagnosed High-Risk Exploratory Arm", Blood, 136(Supplement 1):48-50 (2020).
Zeidner J. et al., Zella 201: A Biomarker-Guided Phase II Study of Alvocidib Followed by Cytarabine and Mitoxantrone in MCL-1 Dependent Acute Myeloid Leukemia (AML): Results of Newly Diagnosed High-Risk Exploratory Arm . American Society of Hematology—62nd Annual Meeting. 2020.
Zeidner, J.F., et al., "A Prospective Biomarker Analysis of Alvocidib Followed by Cytarabine and Mitoxantrone in MCL-1-dependent Relapsed/Refractory Acute Myeloid Leukemia", Blood Cancer Journal, 11(175):5 pages (2021).
Hirayama, N., yukikagobutsukessho sakusei handobukku (handbook for preparation of organic compound crystals)—genri to nouhau—(principle and know-how), Maruzen Inc., Jul. 25, 2008, p. 57-84.
Kawaguchi, Y. et al., "Drug and Crystal Polymorphism," Journal of Human Environmental Engineering, 310-317 (2002).
"Shiniyakuhin no kikaku oyobi shakenhoho no settei nitsuite" (setting of the standard and test method for new pharmaceuticals), iyakushinpatsu No. 568, May 1, 2001.
Takata, N., API form screening and selection in drug discovery stage, Pharm Stage, vol. 6, No. 10, Jan. 15, 2007, p. 20-25.
Tenuta, A. et al., "Clinical trial risk in castration-resistant prostate cancer: immunotherapies show promise," BJU Int, vol. 113; E82-E89 (2014).
Tosi, P. et al., "Concensus conference on the management of tumor lysis syndrome," Haematologica, vol. 93; No. 12; 1877-1885 (2008).
Yamano, M., Approach to Crystal Polymorph in Process Research of New Drug, Journal of Synthetic Organic Chemistry, 2007.

* cited by examiner

ALVOCIDIB PRODRUGS HAVING INCREASED BIOAVAILABILITY

RELATED APPLICATIONS

This application is a continuation of U.S. application Ser. No. 16/727,693, filed Dec. 26, 2019, which is a continuation of U.S. application Ser. No. 16/279,958, filed Feb. 19, 2019, now U.S. Pat. No. 10,562,925, issued Feb. 18, 2020, which is a divisional of U.S. application Ser. No. 15/673,213, filed Aug. 9, 2017, now U.S. Pat. No. 10,259,835, issued Apr. 16, 2019, which is a divisional of U.S. application Ser. No. 15/158,206, filed May 18, 2016, now U.S. Pat. No. 9,758,539, issued Sep. 12, 2017, which claims the benefit of U.S. Provisional Application No. 62/163,188, filed May 18, 2015. The entire teachings of the above applications are incorporated herein by reference.

BACKGROUND

Technical Field

The present invention is generally directed to phosphate prodrugs of alvocidib and use of the same for treatment of cancer.

Description of the Related Art

Cyclin-dependent kinases (CDKs) are important regulators that control the timing and coordination of the cell cycle. CDKs form reversible complexes with their obligate cyclin partners to control transition through key junctures in the cell cycle. For example, the activated CDK4-cyclin D1 complex controls progression through the G1 phase of the cell cycle, while the CDK1-cyclin B1 complex controls entry into the mitotic phase of the cell cycle. Endogenous cyclin dependent kinase inhibitory proteins (CDKIs) are known to bind either the CDK or cyclin component and inhibit the kinase activity of the complex. In many tumors such as melanomas, pancreatic and esophageal cancers, these natural CDKIs are either absent or mutated. Thus, selective CDK inhibitors may prove to be effective chemotherapeutic agents.

Alvocidib (also known as Flavopiridol) is a synthetic flavone having the following structure:

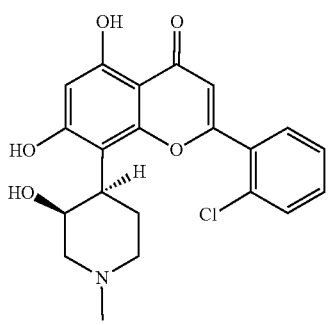

Alvocidib is a potent and selective inhibitor of the CDKs and has antitumor activity against various tumor cells lines, such as human lung carcinoma and breast carcinoma and also inhibits tumor growth in xenograft models. Alvocidib has been shown to induce arrest in both the G1 and G2 phases of the cell cycle and also inhibit polymerase II driven transcription by inhibiting CDK9. By inhibiting CDK9, which forms part of the complex known as the positive transcription elongation factor or P-TEFb, alvocidib treatment reduces the expression of key oncogenes such MYC and key anti-apoptotic proteins such as MCL1. Accordingly, alvocidib is an attractive therapeutic agent for cancer and is currently undergoing clinical trials in relapsed/refractory AML patients.

Oral administration of alvocidib has been limited by gastrointestinal toxicity and limited oral bioavailability. Further, preclinical studies suggest that prolonged exposure may be important for maximizing alvocidib's activity. Accordingly, continuous intravenous infusion schedules have been extensively explored in human trials. Alternative hybrid dosing, including an intravenous bolus dose followed by a slow infusion have also been explored, but to date there have been no reports of orally delivering a therapeutically effective amount of alvocidib.

While progress has been made, there remains a need in the art for increasing the oral bioavailability of alvocidib. The present invention fulfills this need and provides related advantages.

BRIEF SUMMARY

In brief, embodiments of the present invention provide phosphate prodrugs of alvocidib having increased bioavailability relative to the alvocidib parent compound. Accordingly, in one embodiment is provided a compound having the following structure (I):

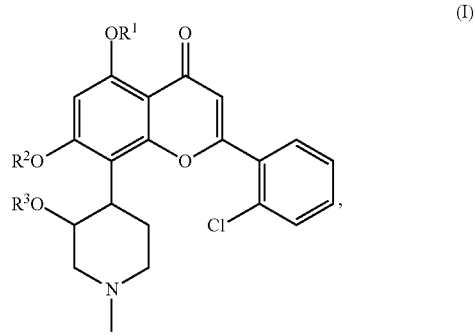

or a stereoisomer, tautomer or pharmaceutically acceptable salt thereof, wherein:
one of $R^1$, $R^2$ or $R^3$ is —P(=O)(OH)$_2$, and the other two of $R^1$, $R^2$ and $R^3$ are each H.

Other embodiments are directed to a pharmaceutical composition comprising a pharmaceutically acceptable carrier or excipient and a compound of structure (I). Methods for use of the compound of structure (I), and pharmaceutical compositions comprising the same, for treatment of a disease associated with overexpression of a cyclin-dependent kinase (CDK) in a mammal in need thereof are also provided.

These and other aspects of the invention will be apparent upon reference to the following detailed description. To this end, various references are set forth herein which describe in more detail certain background information, procedures, compounds and/or compositions, and are each hereby incorporated by reference in their entirety.

DETAILED DESCRIPTION

Figure 1:
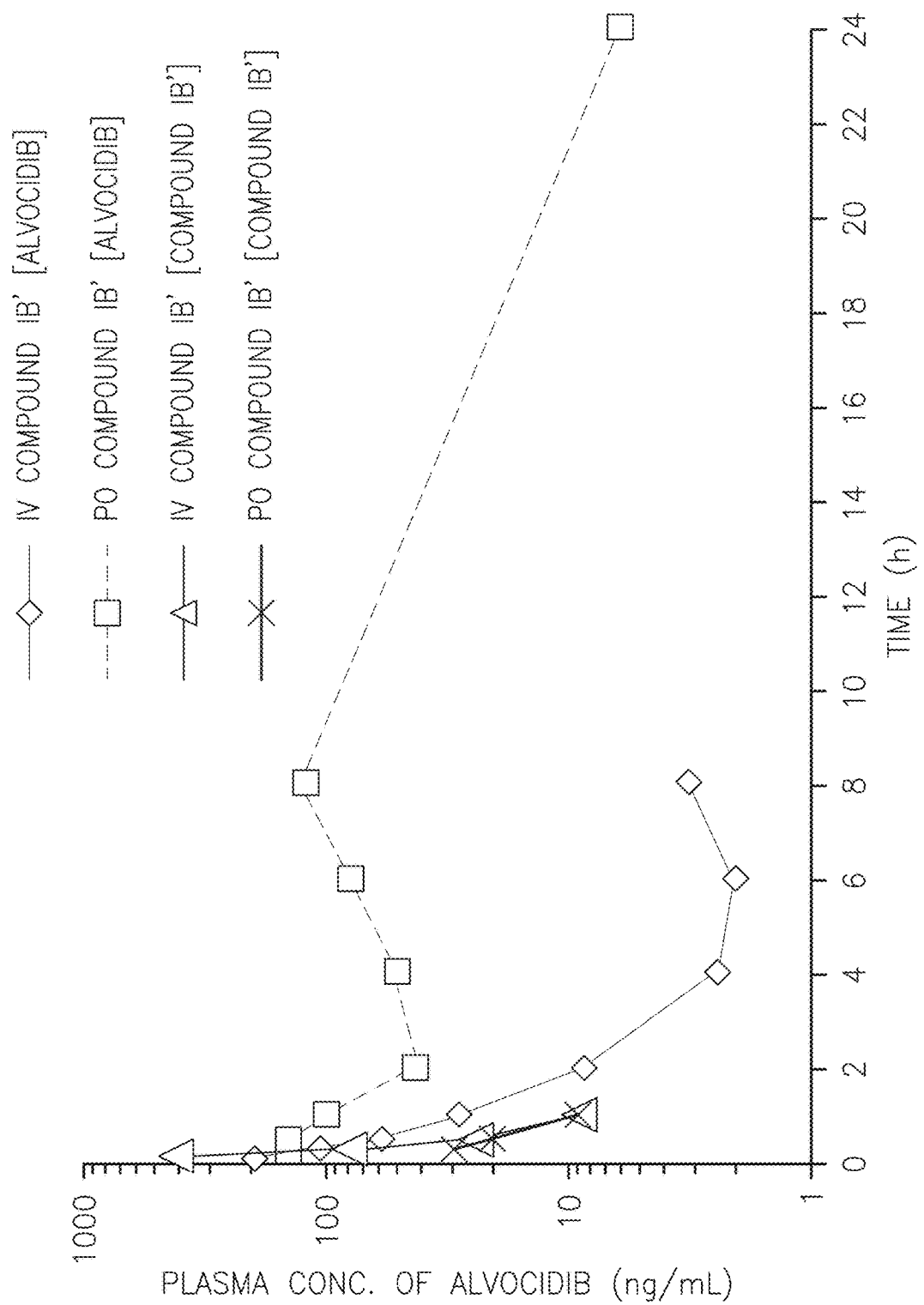
FIG. 1 shows the pharmacokinetic profile of alvocidib and compound IB following the administration of compound IB to Sprague Dawley rats.

In the following description, certain specific details are set forth in order to provide a thorough understanding of various embodiments of the invention. However, one skilled in the art will understand that the invention may be practiced without these details.

Unless the context requires otherwise, throughout the present specification and claims, the word "comprise" and variations thereof, such as, "comprises" and "comprising" are to be construed in an open, inclusive sense, that is, as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features or characteristics may be combined in any suitable manner in one or more embodiments.

Embodiments of the present invention include phosphate prodrugs of alvocidib. "Phosphate" refers to the —OP(=O)(OH)$_2$ moiety. For ease of illustration the phosphate moieties herein are often depicted in the di-protonated form, but also exist in the mono-protonated (—OP(=O)(OH)(O$^-$)) and unprotonated forms (—OP(=O)(O$^-$)$_2$), depending on pH. The mono- and unprotonated forms will typically be associated with a counterion, such that the compounds are in the form of a pharmaceutically acceptable salt. Such mono- and unprotonated forms, and their pharmaceutically acceptable salts, are encompassed within the scope of the inventions, even if not specifically illustrated in the chemical structures.

"Prodrug" is meant to indicate a compound that may be converted under physiological conditions or by solvolysis to a biologically active compound described herein (e.g., compound of structure (I)). Thus, the term "prodrug" refers to a precursor of a biologically active compound that is pharmaceutically acceptable. In some aspects, a prodrug is inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

A "compound of the invention" refers to a compound of structure (I), and its substructures, as defined herein.

Embodiments of the invention disclosed herein are also meant to encompass all pharmaceutically acceptable compounds of structure (I) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. These radiolabelled compounds could be useful to help determine or measure the effectiveness of the compounds, by characterizing, for example, the site or mode of action, or binding affinity to pharmacologically important site of action. Certain isotopically-labelled compounds of structure (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. 2H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of structure (I) can generally be prepared by conventional techniques known to those skilled in the art or by processes analogous to those described in the Preparations and Examples as set out below using an appropriate isotopically-labeled reagent in place of the non-labeled reagent previously employed.

Embodiments of the invention disclosed herein are also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, embodiments of the invention include compounds produced by a process comprising administering a compound of this invention to a mammal for a period of time sufficient to yield a metabolic product thereof. Such products are typically identified by administering a radiolabelled compound of the invention in a detectable dose to an animal, such as rat, mouse, guinea pig, monkey, or to human, allowing sufficient time for metabolism to occur, and isolating its conversion products from the urine, blood or other biological samples.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, embodiments of the compounds of the present invention may exist as a hydrate, including a monohydrate, dihydrate, hemihydrate, sesquihydrate, trihydrate, tetrahydrate and the like, as well as the corresponding solvated forms. Embodiments of the compound of the invention may be true solvates, while in other cases, the compound of the invention may merely retain adventitious water or be a mixture of water plus some adventitious solvent.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Mammal" includes humans and both domestic animals such as laboratory animals and household pets (e.g., cats, dogs, swine, cattle, sheep, goats, horses, rabbits), and non-domestic animals such as wildlife and the like.

"Effective amount" or "therapeutically effective amount" refers to that amount of a compound of the invention which, when administered to a mammal, preferably a human, is sufficient to effect treatment, as defined below, of a disease associated with overexpression of a cyclin-dependent kinase (CDK) in the mammal, preferably a human. The amount of a compound of the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) relieving the symptoms resulting from the disease or condition, i.e., relieving pain without addressing the underlying disease or condition. As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable.

Embodiments of the present invention contemplate various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. Embodiments of the present invention include tautomers of any said compounds.

I. Compounds

As noted above, embodiments of the present disclosure are directed to prodrugs of alvocidib having increased bioavailability relative to the parent compound. Surprisingly, experiments performed in support of the present invention demonstrate that a monophosphate analogue of alvocidib has a bioavailability of approximately 1.3 times the parent alvocidib compound when delivered orally to CD-1 mice and more than 8 times that of the related diphosphate prodrugs. The presently disclosed monophosphate compounds are metabolized to alvocidib in vivo and, while not wishing to be bound by theory, it is believed that the increase in bioavailability of alvocidib released from the monophosphate prodrug compared to the alvocidib parent compound is related to a slower rate of metabolism of the prodrug compared to alvocidib. Other expected advantages of the present compounds include increased solubility in typical pharmaceutical formulations, in water and in bodily fluids, and decreased toxicity relative to the alvocidib parent compound when administered orally.

Accordingly, in one embodiment a compound is provided having the following structure (I):

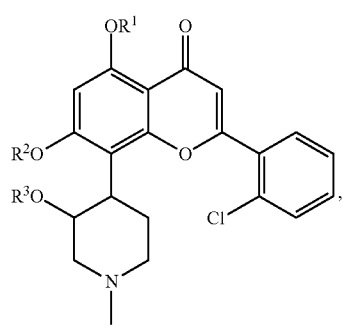

(I)

or a stereoisomer, tautomer or pharmaceutically acceptable salt thereof, wherein:

one of $R^1$, $R^2$ or $R^3$ is —P(=O)(OH)$_2$, and the other two of $R^1$, $R^2$ and $R^3$ are each H.

In certain embodiments, the compound has the following structure (I'):

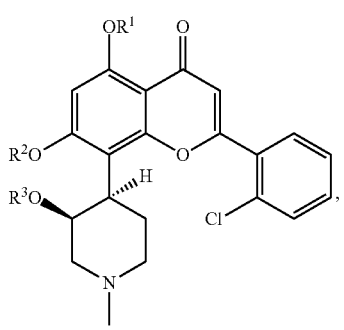

(I')

In some other embodiments, the compound has the following structure (IA):

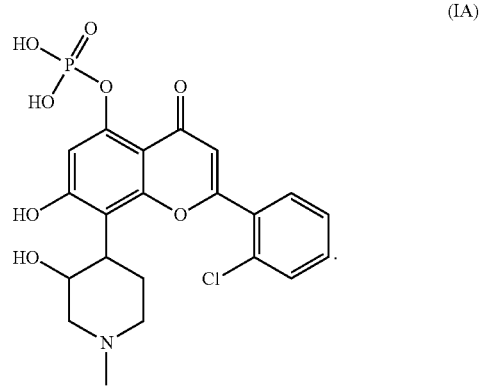 [SMILES: CN1CCC(c2c(O)cc(OP(=O)(O)O)c3c(=O)cc(-c4ccccc4Cl)oc23)C(O)C1]

(IA)

In some more embodiments, the compound has the following structure (IA'):

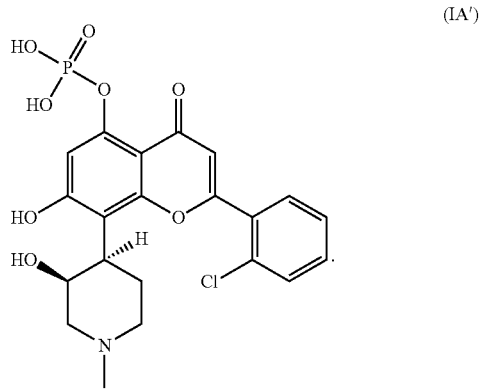 [SMILES: CN1CC[C@H](c2c(O)cc(OP(=O)(O)O)c3c(=O)cc(-c4ccccc4Cl)oc23)[C@H](O)C1]

(IA')

In yet other embodiments, the compound has the following structure (IB):

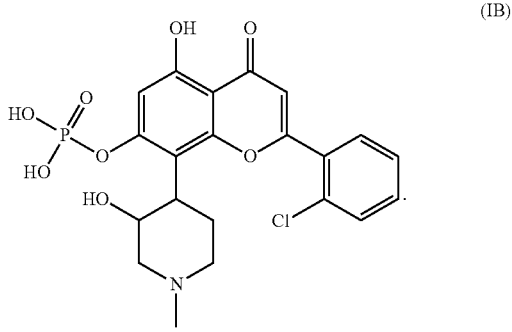 [SMILES: CN1CCC(c2c(OP(=O)(O)O)cc(O)c3c(=O)cc(-c4ccccc4Cl)oc23)C(O)C1]

(IB)

In other different embodiments, the compound has the following structure (IB'):

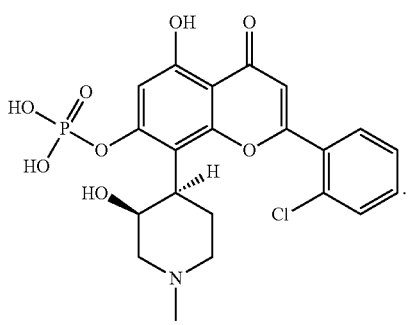

In still more embodiments, the compound has the following structure (IC):

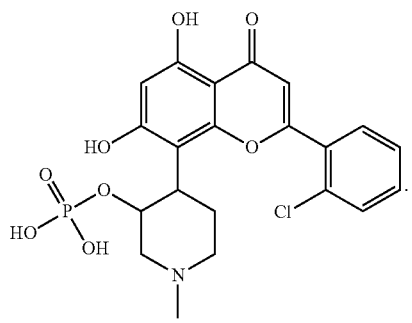

In some other different embodiments, the compound has the following structure (IC'):

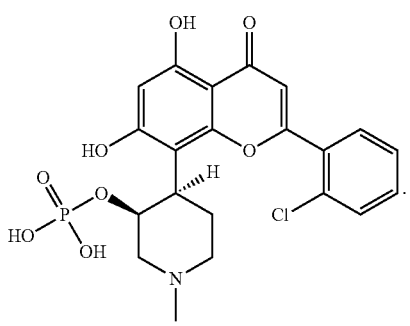

In some embodiments, any of the foregoing compounds are in the form of a pharmaceutically acceptable salt. The salt may be an acid addition salt or a base addition salt. For example, the salt may be an amine salt formed by protonation of the N-methyl piperazine moiety (e.g., HCl salt and the like). In other embodiments, the salt is formed at the phosphate, and the compounds are in the form of mono- or di-salts of the phosphate group (e.g., mono- or disodium phosphate salt and the like). All pharmaceutically acceptable salts of the foregoing compounds are included in the scope of the invention.

Also provided are pharmaceutical compositions comprising a pharmaceutically acceptable carrier or excipient and any of the foregoing compounds (i.e., a compound of structure (I), (I'), (IA), (IA'), (IB), (IB'), (IC) or (IC')). Advantageously, the presently disclosed compounds have increased bioavailability relative to the alvocidib parent compound, and thus certain embodiments are directed to the foregoing pharmaceutical compositions formulated for oral delivery. Any of the carriers and/or excipients known in the art for oral formulation may be used in these embodiments, in addition to other carriers and/or excipients derivable by one of ordinary skill in the art.

For the purposes of administration, the compounds of the present invention may be administered as a raw chemical or may be formulated as pharmaceutical compositions. Embodiments of the pharmaceutical compositions of the present invention comprise a compound of structure (I) and a pharmaceutically acceptable carrier, diluent or excipient. The compound of structure (I) is present in the composition in an amount which is effective to treat a particular disease or condition of interest—that is, typically in an amount sufficient to treat a disease associated with overexpression of a cyclin-dependent kinase (CDK), and preferably with acceptable toxicity to the patient. Bioavailability of compounds of structure (I) can be determined by one skilled in the art, for example, as described in the Examples below. Appropriate concentrations and dosages can be readily determined by one skilled in the art.

Administration of the compounds of the invention, or their pharmaceutically acceptable salts, in pure form or in an appropriate pharmaceutical composition, can be carried out via any of the accepted modes of administration of agents for serving similar utilities. The pharmaceutical compositions of embodiments of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see *Remington: The Science and Practice of Pharmacy*, 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings of this invention.

A pharmaceutical composition of some embodiments of the invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of some embodiments of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of certain embodiments of the invention intended for either parenteral or oral administration should contain an amount of a compound of the invention such that a suitable dosage will be obtained.

In some embodiments, the pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

The pharmaceutical composition of various embodiments of the invention may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

Embodiments of the pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of some embodiments of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of other embodiments of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

In some embodiments, the pharmaceutical compositions of the invention may be prepared by methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

Compounds of the invention, or pharmaceutically acceptable derivatives thereof, may also be administered simultaneously with, prior to, or after administration of one or more other therapeutic agents. Such combination therapy includes administration of a single pharmaceutical dosage formulation which contains a compound of the invention and one or more additional active agents, as well as administration of the compound of the invention and each active agent in its own separate pharmaceutical dosage formulation. For example, a compound of the invention and the other active agent can be administered to the patient together in a single oral dosage composition such as a tablet or capsule, or each agent administered in separate oral dosage formulations. Where separate dosage formulations are used, the compounds of the invention and one or more additional active agents can be administered at essentially the same time, i.e., concurrently, or at separately staggered times, i.e., sequentially; combination therapy is understood to include all these regimens.

In some embodiments, the concentration of the compound of structure (I) provided in the pharmaceutical compositions of the present invention is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, the concentration of the compound of structure (I) provided in the pharmaceutical compositions of the present invention is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some embodiments, the concentration of the compound of structure (I) provided in the pharmaceutical compositions of the present invention is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some embodiments, the concentration of the compound of structure (I) provided in the pharmaceutical compositions of the present invention is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount the compound of structure (I) provided in the pharmaceutical compositions of the present invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of the compound of structure (I) provided in the pharmaceutical compositions of the present invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

In some embodiments, the amount of the compound of structure (I) provided in the pharmaceutical compositions of the present invention is in the range of 0.0001-10 g, 0.0005-9 g, 0.001-8 g, 0.005-7 g, 0.01-6 g, 0.05-5 g, 0.1-4 g, 0.5-4 g, or 1-3 g.

It will also be appreciated by those skilled in the art that, in the processes for preparing compounds of structure (I) described herein, the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

Furthermore, all compounds of the invention which exist in free base or acid form can be converted to their pharmaceutically acceptable salts by treatment with the appropriate inorganic or organic base or acid by methods known to one skilled in the art. Salts of the compounds of the invention can be converted to their free base or acid form by standard techniques.

Compounds of structure (I) can be prepared by addition of a phosphate group to one of the three free hydroxyls of alvocidib. The alvocidib parent compound (and salts and solvates thereof) can be purchased from commercial sources or prepared according to methods known in the art, for example as described in U.S. Pat. Nos. 6,136,981; 6,225,473; 6,406,912; 6,576,647; and 6,821,990; the full disclosures of which are herein incorporated by reference in their entireties.

The following General Reaction Scheme illustrates a method of making compounds of this invention, i.e., compound of structure (I):

or a stereoisomer, tautomer or pharmaceutically acceptable salt thereof, wherein $R^1$, $R^2$ and $R^3$ are as defined above. It is understood that one skilled in the art may be able to make these compounds by similar methods or by combining other methods known to one skilled in the art. It is also understood that one skilled in the art would be able to make, in a similar manner as described below, other compounds of structure (I) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described in this invention.

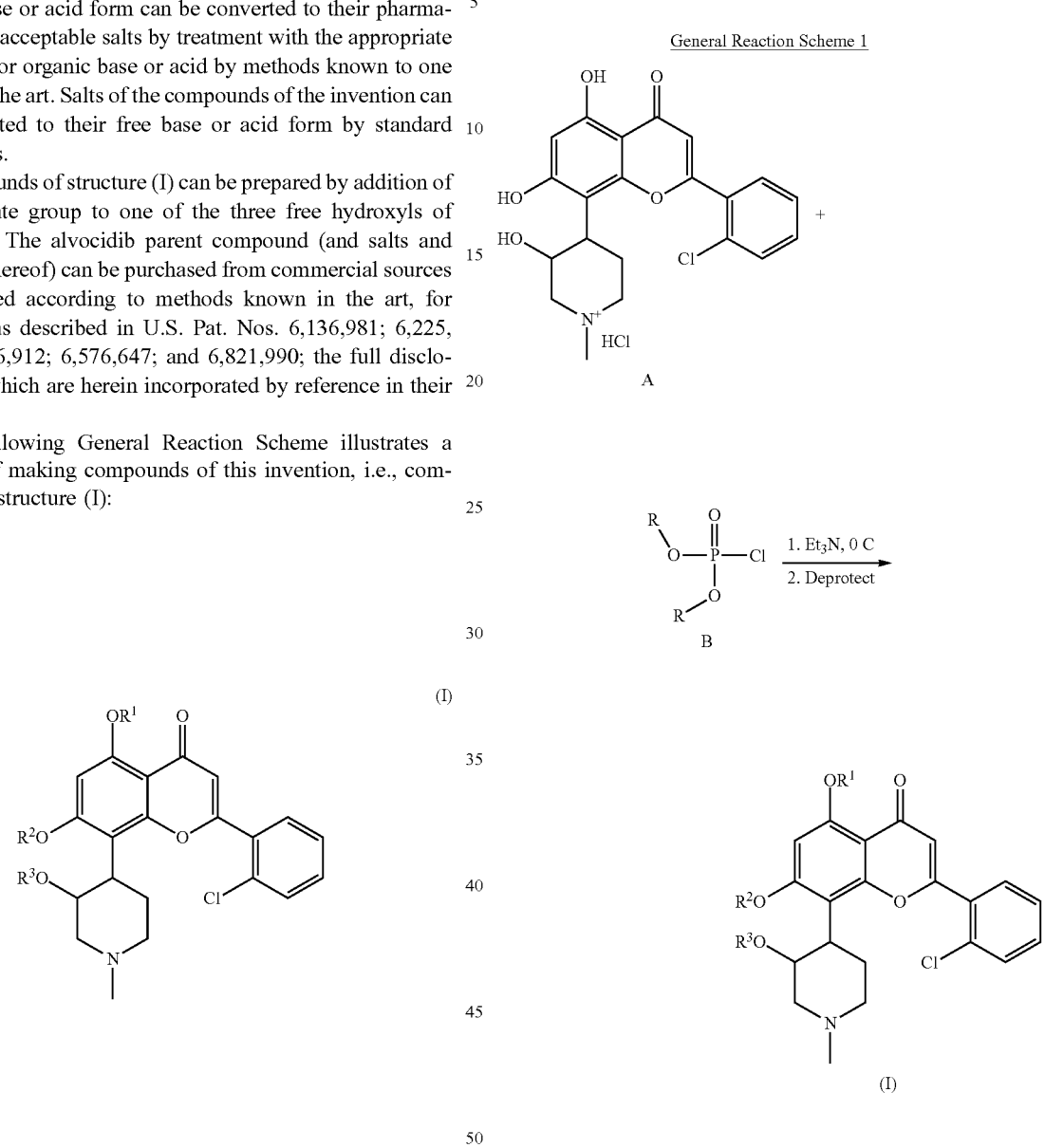

As shown in General Reaction Scheme 1, alvocidib HCl salt A is first reacted with an appropriately protected chlorophosphate (i.e., B, wherein R is a protecting group, such as ethyl). Deprotection then provides the desired compound of structure (I). It will be apparent to one of ordinary skill in the art that compounds of structure (I) having a single phosphate at any one of the three hydroxyl groups of alvocidib can be prepared according to the above scheme, and the desired regioisomer separated by usual techniques, such as chromatography. Protecting group strategies for optimizing the yield of the desired regioisomer will also be apparent to one of ordinary skill in the art.

Methods

In various embodiments, the invention provides a method for treating a disease in a mammal in need thereof by administration of a compound of structure (I), or a pharmaceutical composition comprising the same, to the mammal. In some specific embodiments, the method is for treating a disease associated with overexpression of a cyclin-dependent kinase (CDK) in a mammal in need thereof, the method comprising administering a therapeutically effective amount of any of the foregoing compounds of structure (I), or a pharmaceutical composition comprising the same, to the mammal.

In some more embodiments, the disease is cancer, for example a hematologic cancer. In some of these embodiments, the hematologic cancer is selected from acute myelogenous leukemia (AML), multiple myeloma, follicular lymphoma, acute lymphoblastic leukemia (ALL), chronic lymphocytic leukemia (CLL) and non-Hodgkin's lymphoma. In other embodiments, the hematological cancer is acute myelogenous leukemia (AML). In other different embodiments, the hematologic cancer is chronic lymphocytic leukemia (CLL). In still more different embodiments, the hematologic cancer is myelodysplasic syndrome (MDS).

In some other specific embodiments of the foregoing methods, the method comprises orally administering the compound of structure (I), or the pharmaceutical composition comprising the same, to the mammal.

In addition to the above exemplary diseases, a wide variety of cancers, including solid tumors and leukemias (e.g., acute myeloid leukemia) are amenable to the methods disclosed herein. Types of cancer that may be treated in various embodiments include, but are not limited to: adenocarcinoma of the breast, prostate, and colon; all forms of bronchogenic carcinoma of the lung; myeloid; melanoma; hepatoma; neuroblastoma; papilloma; apudoma; choristoma; branchioma; malignant carcinoid syndrome; carcinoid heart disease; and carcinoma (e.g., Walker, basal cell, basosquamous, Brown-Pearce, ductal, Ehrlich tumor, Krebs 2, merkel cell, mucinous, non-small cell lung, oat cell, papillary, scirrhous, bronchiolar, bronchogenic, squamous cell, and transitional cell). Additional types of cancers that may be treated include: histiocytic disorders; leukemia; histiocytosis malignant; Hodgkin's disease; immunoproliferative small; non-Hodgkin's lymphoma; plasmacytoma; reticuloendotheliosis; melanoma; chondroblastoma; chondroma; chondrosarcoma; fibroma; fibrosarcoma; giant cell tumors; histiocytoma; lipoma; liposarcoma; mesothelioma; myxoma; myxosarcoma; osteoma; osteosarcoma; chordoma; craniopharyngioma; dysgerminoma; hamartoma; mesenchymoma; mesonephroma; myosarcoma; ameloblastoma; cementoma; odontoma; teratoma; thymoma; trophoblastic tumor. Further, the following types of cancers are also contemplated as amenable to treatment: adenoma; cholangioma; cholesteatoma; cyclindroma; cystadenocarcinoma; cystadenoma; granulosa cell tumor; gynandroblastoma; hepatoma; hidradenoma; islet cell tumor; Leydig cell tumor; papilloma; sertoli cell tumor; theca cell tumor; leimyoma; leiomyosarcoma; myoblastoma; myomma; myosarcoma; rhabdomyoma; rhabdomyosarcoma; ependymoma; ganglioneuroma; glioma; medulloblastoma; meningioma; neurilemmoma; neuroblastoma; neuroepithelioma; neurofibroma; neuroma; paraganglioma; paraganglioma nonchromaffin. The types of cancers that may be treated also include, but are not limited to, angiokeratoma; angiolymphoid hyperplasia with eosinophilia; angioma sclerosing; angiomatosis; glomangioma; hemangioendothelioma; hemangioma; hemangiopericytoma; hemangiosarcoma; lymphangioma; lymphangiomyoma; lymphangiosarcoma; pinealoma; carcinosarcoma; chondrosarcoma; cystosarcoma phyllodes; fibrosarcoma; hemangiosarcoma; leiomyosarcoma; leukosarcoma; liposarcoma; lymphangiosarcoma; myosarcoma; myxosarcoma; ovarian carcinoma; rhabdomyosarcoma; sarcoma; neoplasms; nerofibromatosis; and cervical dysplasia.

The compounds of the invention are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that are used in some embodiments. An exemplary dosage is 10 to 30 mg per day. The exact dosage will depend upon the route of administration, the form in which the compound is administered, the subject to be treated, the body weight of the subject to be treated, and the preference and experience of the attending physician.

In some embodiments, a compound of the invention is administered in a single dose. A single dose of a compound of the invention may also be used for treatment of an acute condition.

In some embodiments, a compound of the invention is administered in multiple doses. In some embodiments, dosing is about once, twice, three times, four times, five times, six times, or more than six times per day. In other embodiments, dosing is about once a month, once every two weeks, once a week, or once every other day. In another embodiment a compound of the invention and another agent are administered together about once per day to about 6 times per day. In another embodiment the administration of a compound of the invention and an agent continues for less than about 7 days. In yet another embodiment the administration continues for more than about 6, 10, 14, 28 days, two months, six months, or one year. In some cases, continuous dosing is achieved and maintained as long as necessary.

Administration of the compounds of the invention may continue as long as necessary. In some embodiments, a compound of the invention is administered for more than 1, 2, 3, 4, 5, 6, 7, 14, or 28 days. In some embodiments, a compound of the invention is administered for less than 28, 14, 7, 6, 5, 4, 3, 2, or 1 day. In some embodiments, a compound of the invention is administered chronically on an ongoing basis, e.g., for the treatment of chronic effects.

In some embodiments, the compounds of the invention are administered in dosages. Due to intersubject variability in compound pharmacokinetics, individualization of dosing regimen is provided in certain embodiments. Dosing for a compound of the invention may be found by routine experimentation in light of the instant disclosure and/or can be derived by one of ordinary skill in the art.

EXAMPLES

EXAMPLE 1
PREPARATION OF REPRESENTATIVE PHOSPHATE PRODRUG (IB')

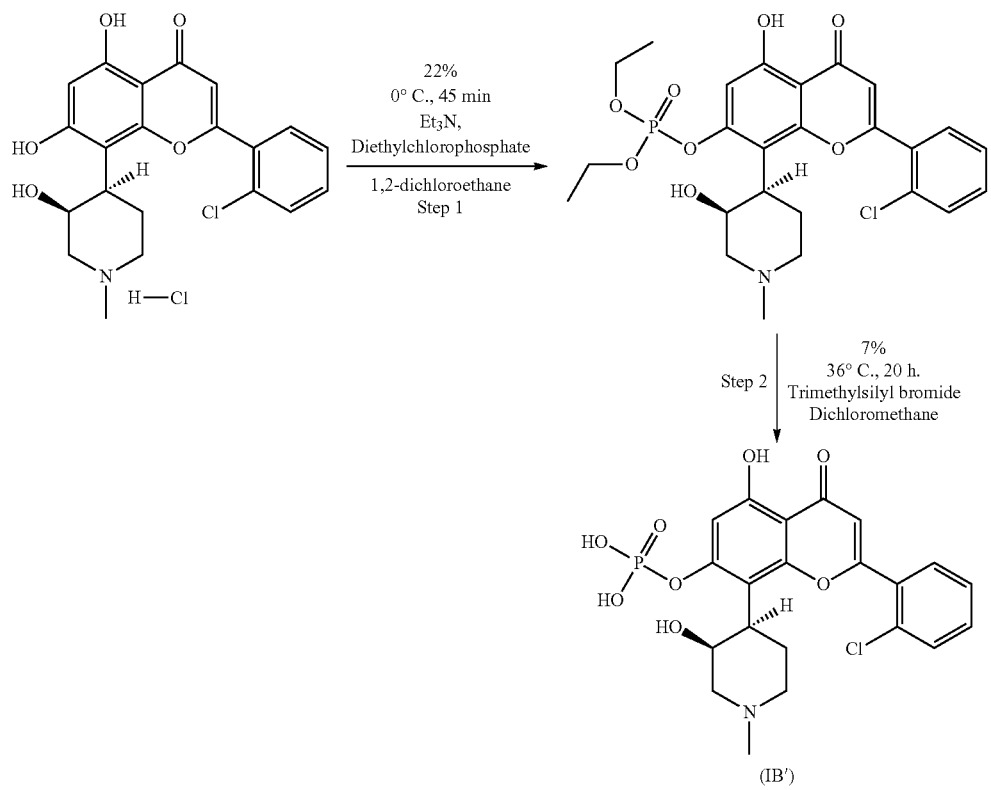

2-(2-chlorophenyl)-5-hydroxy-8-(3-hydroxy-1-methylpiperidin-4-yl)-4-oxo-4H-chromen-7-yl diethyl phosphate A suspension of alvocidib HCl (2 g, 4.56 mmol, 1 eq.) in 1,2-dichloroethane (40 mL) was cooled to 0° C. To this solution, triethylamine (1.9 mL, 13.7 mmol, 3 eq.) followed by diethylchlorophosphate (0.78 g, 4.56 mmol, 1 eq.) were added. The reaction mixture was stirred at 0° C. for 30-45 min. The reaction mixture was then poured onto ice and extracted with dichloromethane (3×25 mL). The combined organic layers were dried over anhydrous $Na_2SO_4$ and concentrated to get a crude residue. The crude residue was purified by flash column chromatography using 10-15% methanol in dichloromethane to afford 2-(2-chlorophenyl)-5-hydroxy-8-(3-hydroxy-1-methylpiperidin-4-yl)-4-oxo-4H-chromen-7-yl diethyl phosphate (550 mg, 1.02 mmol; 22%).

LCMS: Column: XBridge C8 (50×4.6 mm×3.5 μm); Mobile phase: A: 10 mM $NH_4CO_3$ in $H_2O$; B: ACN; RT: 5.97; Purity: (Max: 67.63); M+H: 538.0.

2-(2-chlorophenyl)-5-hydroxy-8-(3-hydroxy-1-methylpiperidin-4-yl)-4-oxo-4H-chromen-7-yl dihydrogen phosphate (IB')

To a solution of 2-(2-chlorophenyl)-5-hydroxy-8-(3-hydroxy-1-methylpiperidin-4-yl)-4-oxo-4H-chromen-7-yl diethyl phosphate (0.55 g, 1.02 mmol, 1 eq.) in dichloromethane (4 mL) at 0° C., trimethylsilylbromide (2.0 mL, 15.1 mmol, 15 eq.) was added. The reaction mixture was then heated at 36° C. under sealed condition for 20 h. The reaction mixture was evaporated. The crude residue obtained was purified by preparative HPLC to afford 2-(2-chlorophenyl)-5-hydroxy-8-(3-hydroxy-1-methylpiperidin-4-yl)-4-oxo-4H-chromen-7-yl dihydrogen phosphate (35 mg; 0.073 mmol; 7%).

LCMS: Column: XBridge C8 (50×4.6 mm×3.5 μm); Mobile phase: A: 10 mM $NH_4CO_3$ in $H_2O$; B: ACN; RT: 3.11; Purity: (Max: 93.56); M+H: 482.0.

HPLC: Column: XBridge C8 (50×4.6 mm×3.5 μm); Mobile phase: A: 0.1% TFA in $H_2O$; B: ACN; RT: 2.55; Purity: (Max: 96.39; 254 nm: 96.57).

1HNMR (DMSO-$d_6$-$D_2O$ exchange): δ 7.84 (d, J=7.20 Hz, 1H), 7.71-7.70 (m, 1H), 7.65-7.62 (m, 1H), 7.59-7.55 (m, 1H), 7.07 (s, 1H), 6.62 (s, 1H), 4.12 (s, 1H), 3.60-3.54 (m, 1H), 3.30-3.26 (m, 3H), 3.13-3.11 (m, 2H), 2.71 (s, 3H), 1.83-1.80 (m, 1H).

Example 2

Pharmacokinetic Profile of Alvocidib Prodrugs

The following compounds were prepared and their pharmacokinetic profile determined and compared to the pharmacokinetic profile of compound (IB') as described below.

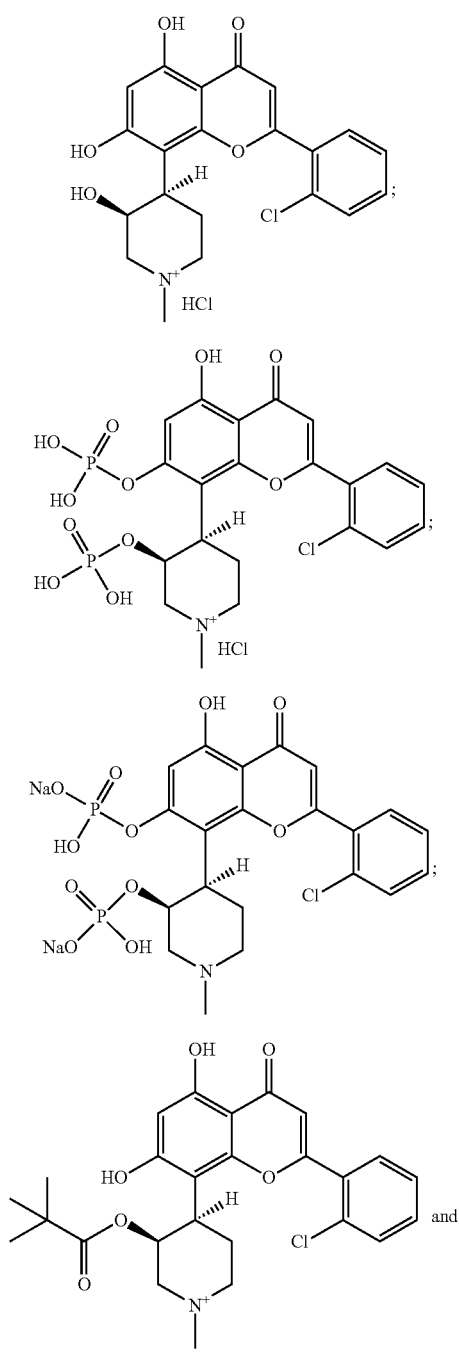

Compounds were prepared and administered to CD-1 mice intravenously (IV) or orally (PO) as summarized in Table 1. The plasma concentration of the alvocidib parent compound was determined at various time intervals (Table 2) and the pharmacokinetic parameters calculated (Table 3). Compounds E and F did not convert to alvocidib in vivo (i.e., no alvocidib was detected in plasma samples of mice treated with these compounds), and their pharmacokinetic parameters were not further investigated. As can be seen in Table 3, the bioavailability of compound (IB') is superior that of the parent alvocidib compound (A) and the two diphosphate compounds (C and D).

TABLE 1

Design of Pharmacokinetic Profiling Experiments

|  | IV | PO |
|---|---|---|
| Dose (mg/kg) | 1 | 10 |
| Dosing volume (ml/kg) | 2 | 10 |
| Formulation Conc (mg/ml) | 0.5 | 1 |
| Formulation Details |  |  |
| IV Formulation | N-methyl pyrollidone:Ethanol:PEG200:NS (2:10:30:58) | |
| PO Formulation | Tween80:Ethanol:PEG400:water (2:10:30:58) | |
| Type of PK Planed |  |  |
| Species | Mouse | |
| Strain | ICR-CD1 | |
| Sex | Male | |
| Age/Body weight: | ~7-8 weeks/25-30 g | |
| Groups | IV: 1 gr; PO: 1 gr | |
| No of animals/group | 3/3 | |
| IV Dosing | Tail vein | |
| PO Dosing | oral gavage | |
| Sample Type | Plasma | |
| Blood collection | Saphenous vein | |
| Anticoagulant used | 0.2% K2 EDTA | |

TABLE 2

Plasma Concentration of Alvocidib
Alvocidib Plasma Concentrations (ng/ml)

| Time (hr) | A IV | A PO | C IV | C PO | D IV | D PO | (IB') IV | (IB') PO |
|---|---|---|---|---|---|---|---|---|
| 0.083 | 427.9 ± 26.5 | — | 30.1 ± 6.5 | — | 9.9 ± 8.0 | — | 366.8 ± 9.9 | — |
| 0.25 | 335.7 ± 64.1 | 1491 ± 211.0 | 53.4 ± 11.0 | 7.5 ± 4.2 | 31.4 ± 17.0 | 5.2 ± 4.7 | 265.1 ± 36.4 | 1868.7 ± 51.1 |
| 0.5 | 263.9 ± 48.2 | 1167.2 ± 186.0 | 62.1 ± 2.3 | 17.9 ± 1.0 | 43.8 ± 11.0 | 14.4 ± 1.8 | 183.6 ± 12.5 | 1880.5 ± 119.1 |
| 1.0 | 136.4 ± 41.9 | 675.5 ± 139.7 | 33.2 ± 15.1 | 28.5 ± 2.3 | 45.3 ± 7.2 | 39.3 ± 1.9 | 105.0 ± 17.8 | 1338.5 ± 188.8 |
| 2.0 | 52.5 ± 8.1 | 333.7 ± 94.5 | 19.8 ± 5.34 | 46.0 ± 3.8 | 17.0 ± 5.4 | 59.5 ± 5.9 | 40.2 ± 1.9 | 740.5 ± 147.4 |

TABLE 2-continued

Plasma Concentration of Alvocidib
Alvocidib Plasma Concentrations (ng/ml)

| Time (hr) | A IV | A PO | C IV | C PO | D IV | D PO | (IB') IV | (IB') PO |
|---|---|---|---|---|---|---|---|---|
| 4.0 | 28.9 ± 6.3 | 304.8 ± 29.5 | 13.5 ± 2.0 | 36.8 ± 1.7 | 9.4 ± 0.7 | 55.5 ± 3.6 | 16.8 ± 1.1 | 388.3 ± 35.7 |
| 6.0 | 13.5 ± 3.3 | 341.3 ± 53.3 | 5.9 ± 0.4 | 100 ± 4.5 | 4.4 ± 0.2 | 108.3 ± 1.4 | 7.22 ± 0.3 | 470.7 ± 18.4 |
| 8.0 | 6.7 ± 0.4 | 241.9 ± 24.9 | 3.6 ± 0.6 | 76.8 ± 3.3 | 2.2 ± 1.6 | 93.1 ± 3.7 | 2.9 ± 0.4 | 252.5 ± 31.0 |
| 24.0 | n.e. | 36.7 ± 11.1 | n.e. | 2.0 ± 0.3 | n.e. | n.e. | n.e. | 21.7 ± 17.5 |

Note:
Results are expressed in Mean ± SD,
n = 3 animals/group
n.e. = not evaluated

TABLE 3

Pharmacokinetic Profiles
Mice PK summary Table (Dose: IV-1 mg/kg & PO-10 mg/kg)

| PK Parameters | A IV | A PO | C IV | C PO | D IV | D PO | (IB') IV | (IB') PO |
|---|---|---|---|---|---|---|---|---|
| $C_{max}$ (ng/mL) | — | 1492.0 ± 211.0 | — | 100.1 ± 4.5 | — | 108.3 ± 1.4 | — | 1922.7 ± 72.1 |
| $T_{max}$ (h) | — | 0.25 ± 0.0 | — | 6.0 ± 0.1 | — | 6.0 ± 0.1 | — | 0.33 ± 0.14 |
| $AUC_{Last}$ (ng * h/mL) | 498.0 ± 46.0 | 5034.1 ± 145.6 | 132.8 ± 14.8 | 776.6 ± 32.8 | 109.0 ± 12.0 | 545.8 ± 11.9 | 363.6 ± 18.0 | 6619.6 ± 631.7 |
| $AUC_{0-\infty}$ (ng * h/mL) | 517.0 ± 47.0 | 5341.1 ± 274.2 | 144.6 ± 13.4 | 785.6 ± 33.5 | 114.3 ± 7.0 | — | 370.2 ± 19.0 | — |
| Clearance (L/h/Kg) | 1.9 ± 0.2 | — | 7.0 ± 0.7 | — | 8.8 ± 0.5 | — | 2.7 ± 0.14 | — |
| Vd (L/Kg) | 5.5 ± 1.2 | — | 22.0 ± 5.1 | — | 22.0 ± 13.1 | — | 6.1 ± 0.0 | — |
| $Vd_{SS}$ (L/Kg) | 3.8 ± 0.6 | — | 21.6 ± 4.4 | — | 23.5 ± 7.4 | — | 4.2 ± 0.1 | — |
| Half life (h) | 2.0 ± 0.4 | 5.7 ± 0.7 | 2.2 ± 0.5 | 3.1 ± 0.1 | 1.72 ± 0.9 | — | 1.57 ± 0.08 | 4.4 ± 1.3 |
| Bioavail. (% F) | | 102 ± 11.7 | | 59.0 ± 8.0 | | 50.5 ± 4.7 | — | 182.3 ± 20.0 |

Note:
Results are expressed in Mean ± SD,
n = 3 animals/group

Example 3

Kinetic Solubility Profiles

The aqueous kinetic solubility of compound IB' was determined across a broad pH range (i.e. pH 2.2-pH 8.7) and compared to the aqueous kinetic solubility of alvocidib for the same pH range. The solubility of compound IB' was found to be in excess of 1 mg/mL at the lowest pH tested (pH 2.2), rising to above 5 mg/mL at pH 6.8 and pH 8.7. By comparison, the solubility of alvocidib is above 1 mg/mL at pH 2.2 and pH 4.5 but drops to 0.02 mg/mL at pH 6.8 and pH 8.7.

TABLE 4

Kinetic Solubility Profiles

| Compound | Concentration tested (mg/mL) | Solubility (mg/mL) pH 2.2 | pH 4.5 | pH 6.8 | pH 8.7 |
|---|---|---|---|---|---|
| Alvocidib | 1 | 1.05 | 0.95 | 0.02 | 0.00 |
| | 5 | 4.82 | 1.99 | 0.02 | 0.02 |
| | 10 | 4.38 | 1.25 | 0.02 | 0.02 |
| Compound IB' | 1 | 1.07 | 1.10 | 1.09 | 1.09 |
| | 5 | 1.90 | 2.33 | 5.56 | 5.65 |
| | 10 | 1.52 | 1.81 | 9.48 | 9.31 |

Example 4

Plasma Stability Profiles

The plasma stability of compound IB' was determined using plasma from four species. Results for mouse, rat, dog and human are shown in Tables 5, 6, 7 and 8 respectively. Alvocidib and flumazenil were used as controls. In mouse, rat and human plasma, compound IB' maintained 100% stability after 5 hour incubation. In dog plasma, approximately 90% of compound IB' remained after 5 hours. By comparison, alvocidib maintained 100% stability across all four species after 5 hours, and flumazenil was unstable in mouse and rat plasma.

TABLE 5

Mouse Plasma Stability Profiles

| | % Remaining | | | | | | |
|---|---|---|---|---|---|---|---|
| Compound | 0 hours | 0.5 hours | 1 hour | 2 hours | 3 hours | 4 hours | 5 hours |
| Flumazenil | 100.00 | 29.96 | 10.21 | 1.56 | 0.39 | 0.20 | 0.07 |
| Alvocidib | 100.00 | 93.58 | 103.12 | 97.19 | 117.38 | 115.72 | 111.28 |
| Compound IB' | 100.00 | 88.48 | 89.83 | 97.71 | 99.61 | 100.46 | 100.20 |

TABLE 6

Rat Plasma Stability Profiles

| | % Remaining | | | | | | |
|---|---|---|---|---|---|---|---|
| Compound | 0 hours | 0.5 hours | 1 hour | 2 hours | 3 hours | 4 hours | 5 hours |
| Flumazenil | 100.00 | 42.23 | 16.13 | 1.69 | 0.23 | 0.00 | 0.00 |
| Alvocidib | 100.00 | 93.12 | 90.20 | 99.31 | 98.69 | 92.57 | 117.71 |
| Compound IB' | 100.00 | 97.39 | 94.60 | 100.04 | 107.48 | 100.20 | 99.78 |

TABLE 7

Dog Plasma Stability Profiles

| | % Remaining | | | | | | |
|---|---|---|---|---|---|---|---|
| Compound | 0 hours | 0.5 hours | 1 hour | 2 hours | 3 hours | 4 hours | 5 hours |
| Flumazenil | 100.00 | 91.80 | 92.00 | 100.99 | 115.10 | 99.44 | 100.53 |
| Alvocidib | 100.00 | 96.41 | 89.16 | 105.76 | 105.84 | 97.65 | 100.40 |
| Compound IB' | 100.00 | 83.66 | 94.53 | 112.61 | 99.16 | 93.91 | 90.24 |

TABLE 8

Human Plasma Stability Profiles

| | % Remaining | | | | | | |
|---|---|---|---|---|---|---|---|
| Compound | 0 hours | 0.5 hours | 1 hour | 2 hours | 3 hours | 4 hours | 5 hours |
| Flumazenil | 100.00 | 96.56 | 90.83 | 92.41 | 117.98 | 95.32 | 94.63 |
| Alvocidib | 100.00 | 92.61 | 93.54 | 93.29 | 111.62 | 100.25 | 104.65 |
| Compound IB' | 100.00 | 96.32 | 88.01 | 104.22 | 102.59 | 94.36 | 100.26 |

Example 5

Pharmacokinetics in Sprague Dawley Rats

The plasma concentrations of alvocidib produced by oral and intravenous (IV) administration of compound IB' and of absorbed compound IB' itself, were determined in male Sprague Dawley (SD) rats (see FIG. 1). Plasma samples were taken at 8 time-points (IV) or 7 time points (oral) over a 24 hour period following a single dose of compound IB' (3 animals per group). The calculated pharmacokinetic parameters are shown in Table 9 and Table 10. Both IV and oral administration of compound IB' led to significant exposure of alvocidib. Administered intravenously, compound IB' (1 mg/kg) was metabolized to alvocidib with a Co of 270.3 ng/mL which was eliminated with a half-life of 1.6 hours. Administered orally, compound IB' (10 mg/kg) was metabolized to alvocidib with a $C_{max}$ of 178.6 ng/ml and a $T_{max}$ of 2.92 hours, which was eliminated with a half-life of 4.4 hours. The bioavailability of alvocidib (99.03%) was calculated from the ratio of the area under the curve (AUC) for alvocidib produced from oral and IV administration of compound IB'. The plasma samples were also analyzed for the presence of compound IB'. The plasma concentrations of compound IB' in SD rats are also shown in FIG. 1 and Table 11. For both IV and oral administration in SD rats, plasma levels of compound IB' dropped below quantitative levels at 2 hours post dosing.

TABLE 9

Pharmacokinetic Parameters for Alvocidib Following Intravenous Administration of Compound IB' in Sprague Dawley Rats

| Parameter | Value | SD |
|---|---|---|
| $C_0$ (ng/mL) | 270.3 | 48.6 |
| $AUC_{in}$ (hr · ng/mL) | 135.6 | 21.1 |
| $AUC_{0-t}$ (hr · ng/mL) | 129.9 | 22.8 |
| $AUC_{in}/AUC_{0-t}$ (%) | 104.6 | 2.3 |
| $V_d$ (L/kg) | 17.50 | 1.93 |
| $CL_p$ (L/hr/kg) | 7.5 | 1.1 |
| $V_{d,ss}$ (L/kg) | 17.71 | 10.08 |
| $MRT_{in}$ (hr) | 2.5 | 1.8 |
| $t_{1/2}$ (hr) | 1.6 | 0.4 |

TABLE 10

Pharmacokinetic Parameters for Alvocidib Following Oral Administration of Compound IB' in Sprague Dawley Rats

| Parameter | Value | SD |
|---|---|---|
| $C_{max}$ (ng/mL) | 178.6 | 47 |
| $T_{max}$ (hr) | 2.92 | 4.4 |
| $AUC_{in}$ (hr · ng/mL) | 1280.5 | 194 |
| $AUC_{0-t}$ (hr · ng/mL) | 1241.2 | 185 |
| $AUC_{in}/AUC_{0-t}$ (%) | 103.2 | 0.8 |
| Bioavailability (%) | 99.03 | 30.2 |
| $t_{1/2}$ (hr) | 4.40 | 0.5 |

TABLE 11

Plasma Concentrations of Compound IB following Intravenous or Oral Administration of Compound IB' in Sprague Dawley Rats

| Time (hr) | IV (ng/mL) | SD | PO (ng/mL) | SD |
|---|---|---|---|---|
| 0.083 | 429.6 | 144.0 | # | # |
| 0.25 | 82.0 | 6.6 | 30.0 | 9.7 |
| 0.50 | 24.6 | 4.2 | 20.4 | 6.6 |
| 1.00 | 9.3 | 2.8 | 9.3 | 0.4 |
| 2.00 | BQL | — | BQL | — |
| 4.00 | BQL | — | BQL | — |
| 6.00 | BQL | — | BQL | — |
| 8.00 | BQL | — | BQL | — |
| 24.00 | BQL | — | BQL | — | not measured
BQL = below quantitation limit

Example 6

Maximum Tolerated Acute Dose in Mice

Figure 2A:
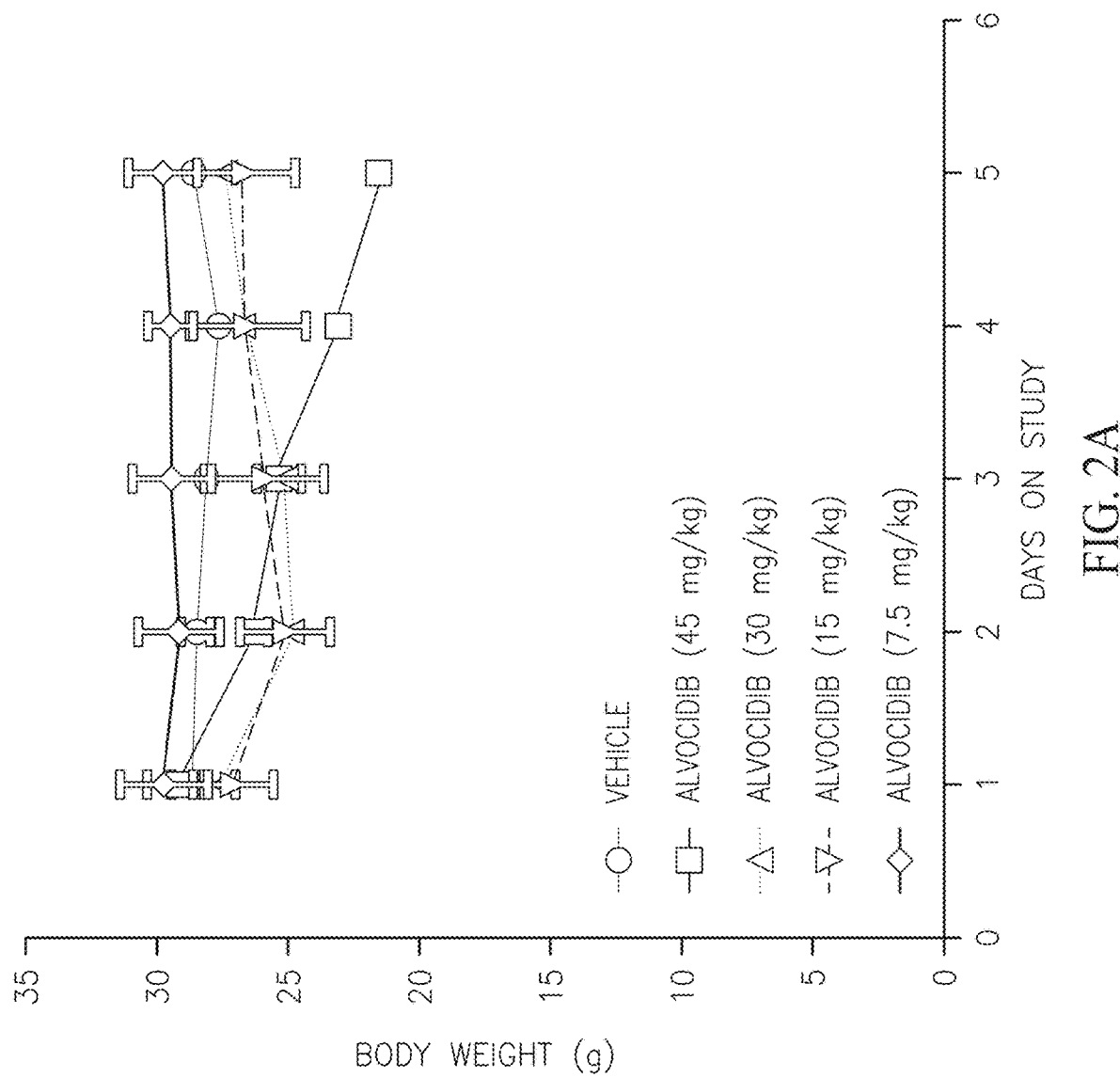
FIG. 2A-D depict the body weights of mice treated with a single dose (FIG. 2A-B orally, FIG. 2C-D intravenously) of alvocidib or compound IB.
Figure 2B:
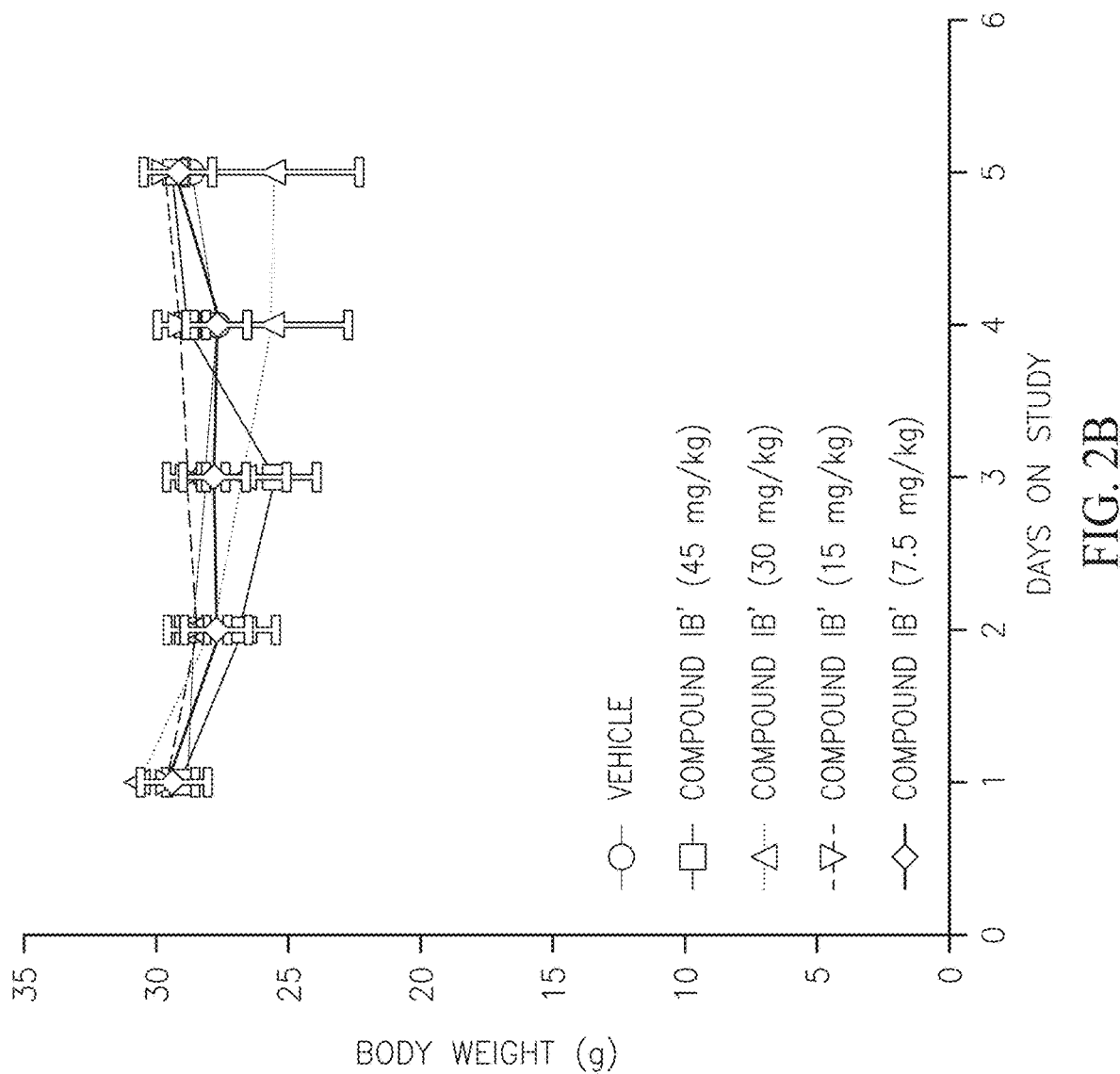
Figure 2C:
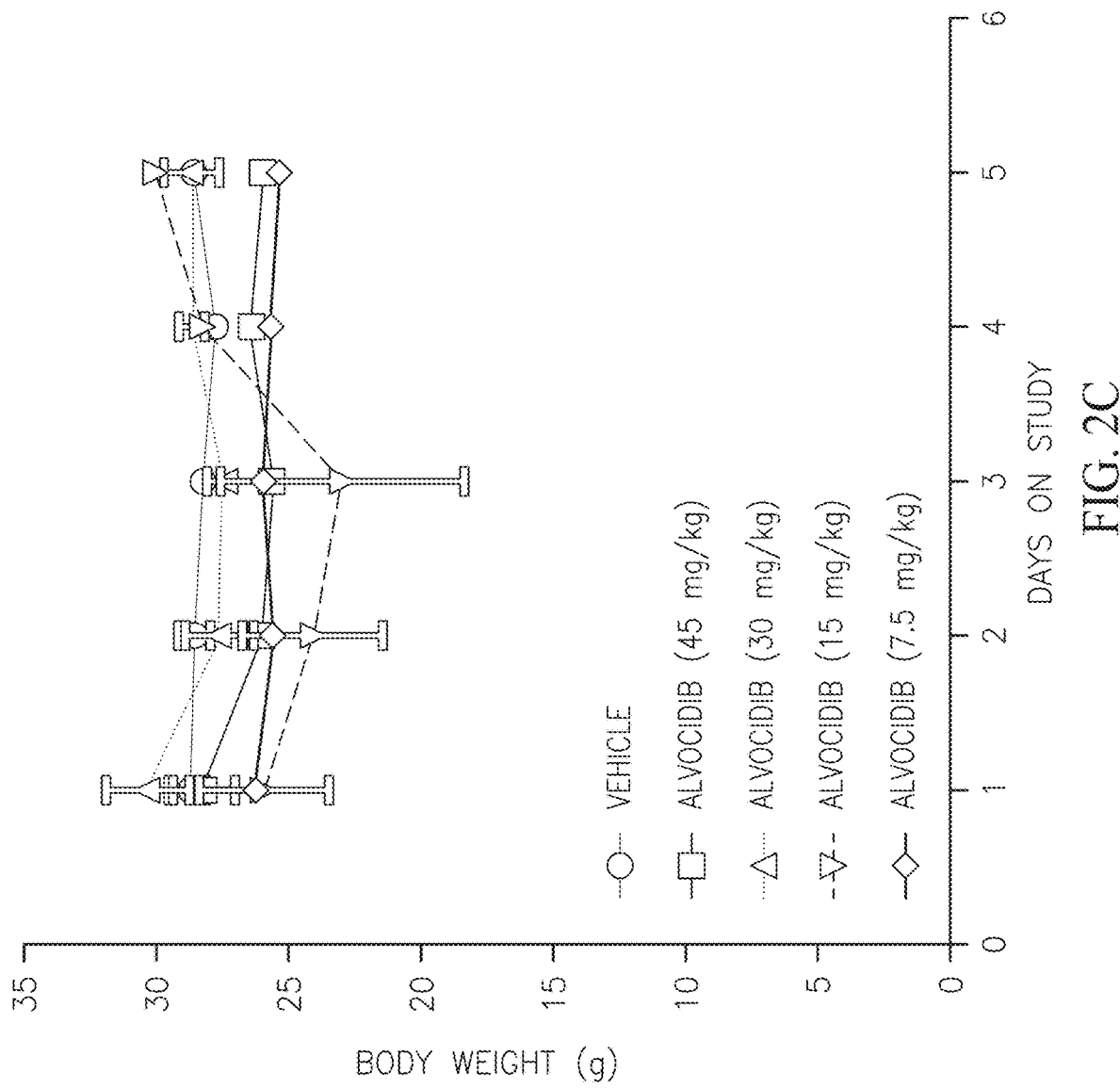
Figure 2D:
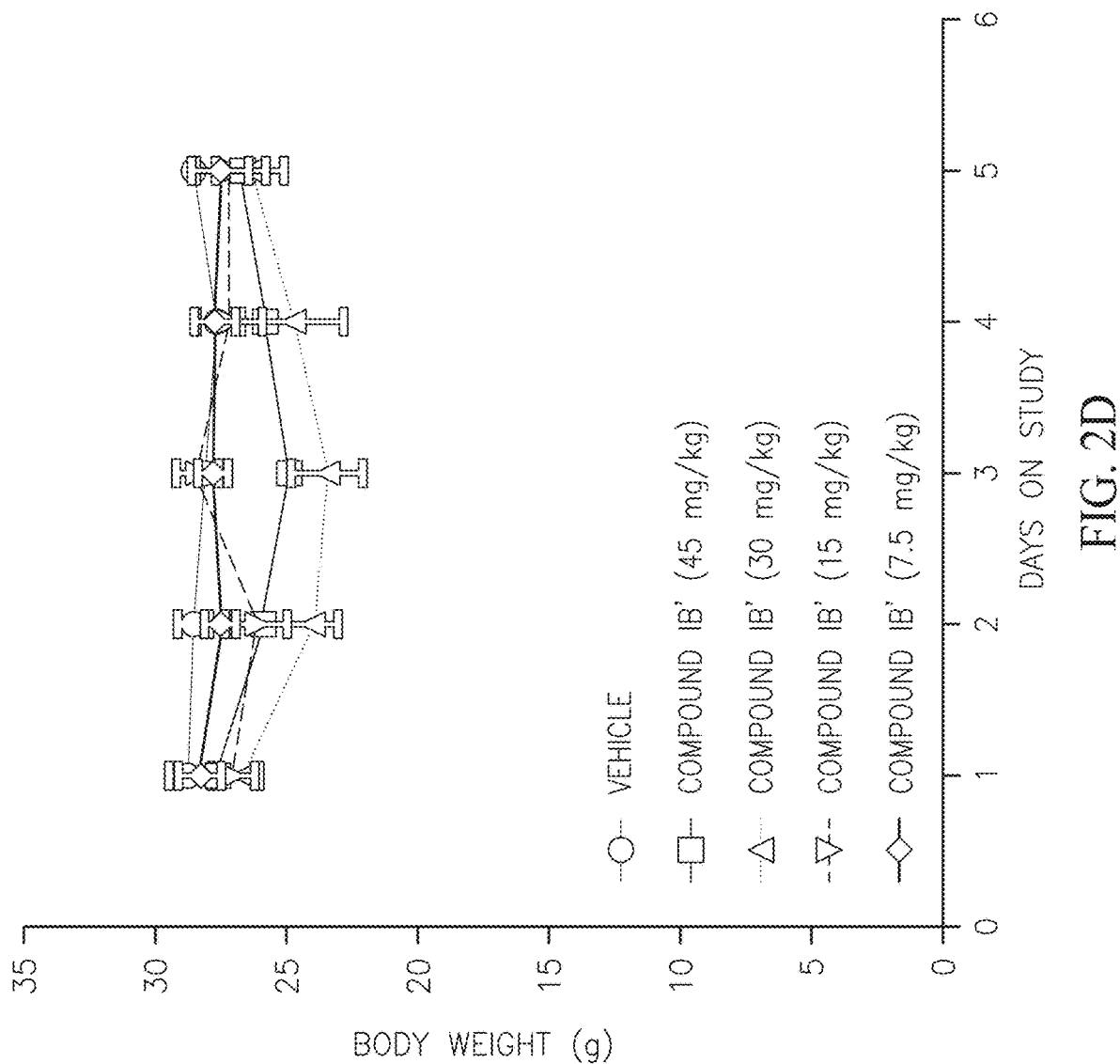

Acute (i.e. single dose) toxicology studies were performed in mice. Acute studies were performed in female SHO SCID mice using three animals per treatment group. Animals were treated with a single dose of compound IB' at 45, 30, 15, or 7.5 mg/kg. For comparison, additional animals were treated with alvocidib at the same dose levels. Body weight measurements following oral dosing (FIGS. 2A-B) and intravenous (IV) dosing (FIG. 2C-D) were used, along with mortality and clinical observations to determine the maximum tolerated acute dose ($MTD_{acute}$).

The results from the acute study determined that the $MTD_{acute}$ of compound IB', dosed orally, is 15 mg/kg. The $MTD_{acute}$ of compound IB', dosed intravenously, is 15 mg/kg. Body weight loss and increased lethargy were observed in animals dosed at 30 mg/kg and 45 mg/kg. In animals dosed orally at 45 mg/kg, one animal died on day two and one animal died on day three. In animals dosed orally at 30 mg/kg, one animal died on day four. In animals dosed intravenously at 45 mg/kg, two animals died on day two. In animals dosed intravenously at 30 mg/kg, one animal died on day three.

The acute $MTD_{acute}$ of alvocidib, when dosed orally, is 15 mg/kg. The $MTD_{acute}$ of alvocidib, dosed intravenously, is 7.5 mg/kg. Some body weight loss, increased lethargy, and animal deaths were observed in animals dosed with alvocidib at both the 30 and 45 mg/kg dose levels.

Body weight loss was observed in surviving animals at 45 mg/kg and 30 mg/kg oral dosing levels of compound IB', peaking at 17% in the 30 mg/kg group. Body weight loss in surviving animals dosed intravenously peaked at 12%.

No overt toxicity was observed in mice dosed orally or intravenously at 15 mg/kg or 7.5 mg/kg. Minor body weight loss peaking at 3.3% in the 15 mg/kg intravenous dosing group was attributed to normal body weight fluctuation in test animals.

Compound IB' is better tolerated ($MTD_{acute}$=15 mg/kg) in mice when dosed intravenously compared to alvocidib ($MTD_{acute}$=7.5 mg/kg).

Example 7

Maximum Tolerated Repeated Dose Schedule in Mice

Figure 3A:
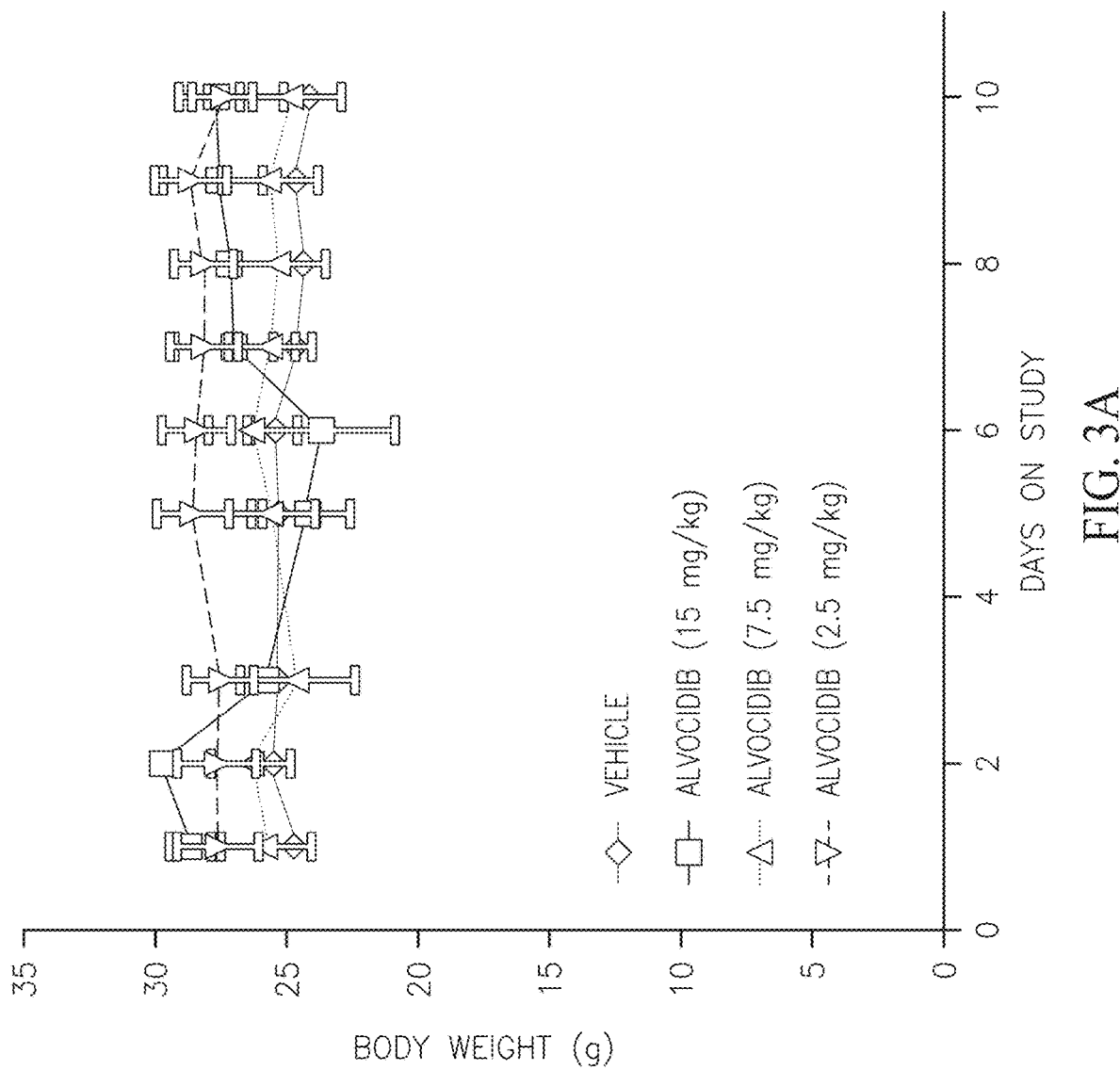
FIG. 3A-D show the body weights of mice treated with daily doses (FIG. 3A-B orally, FIG. 3C-D intravenously) of alvocidib or compound IB.
Figure 3B:
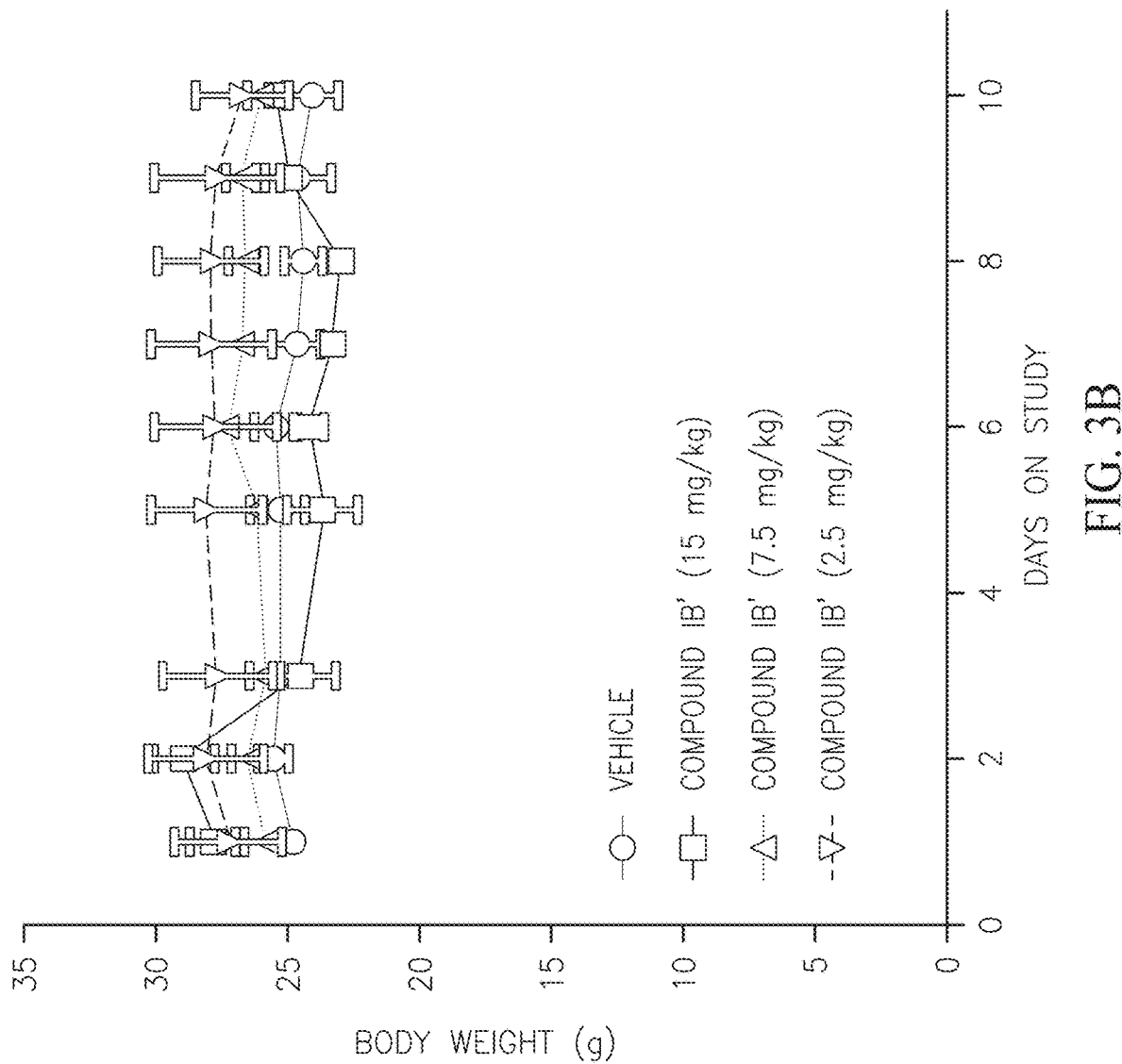
Figure 3C:
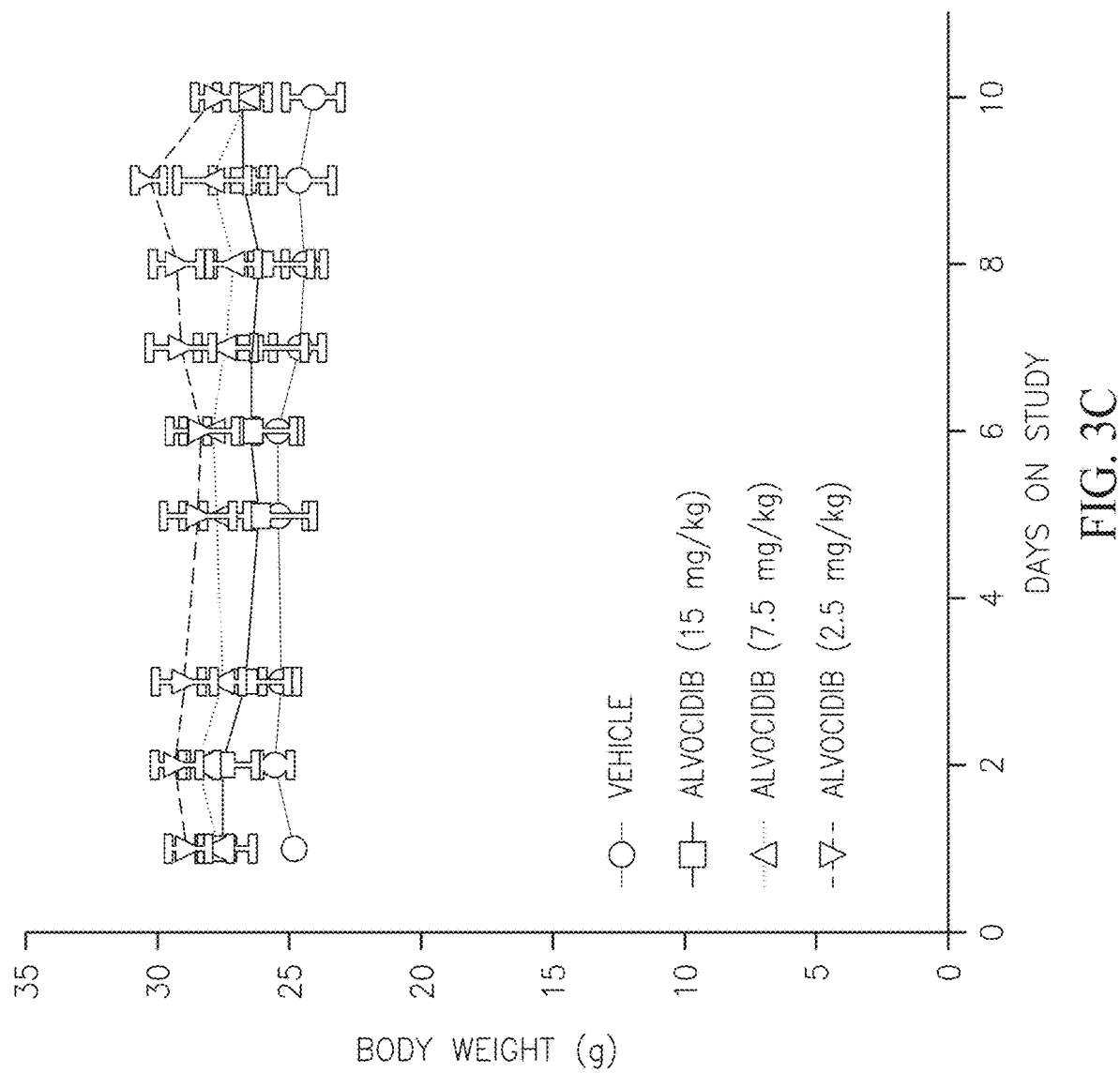
Figure 3D:
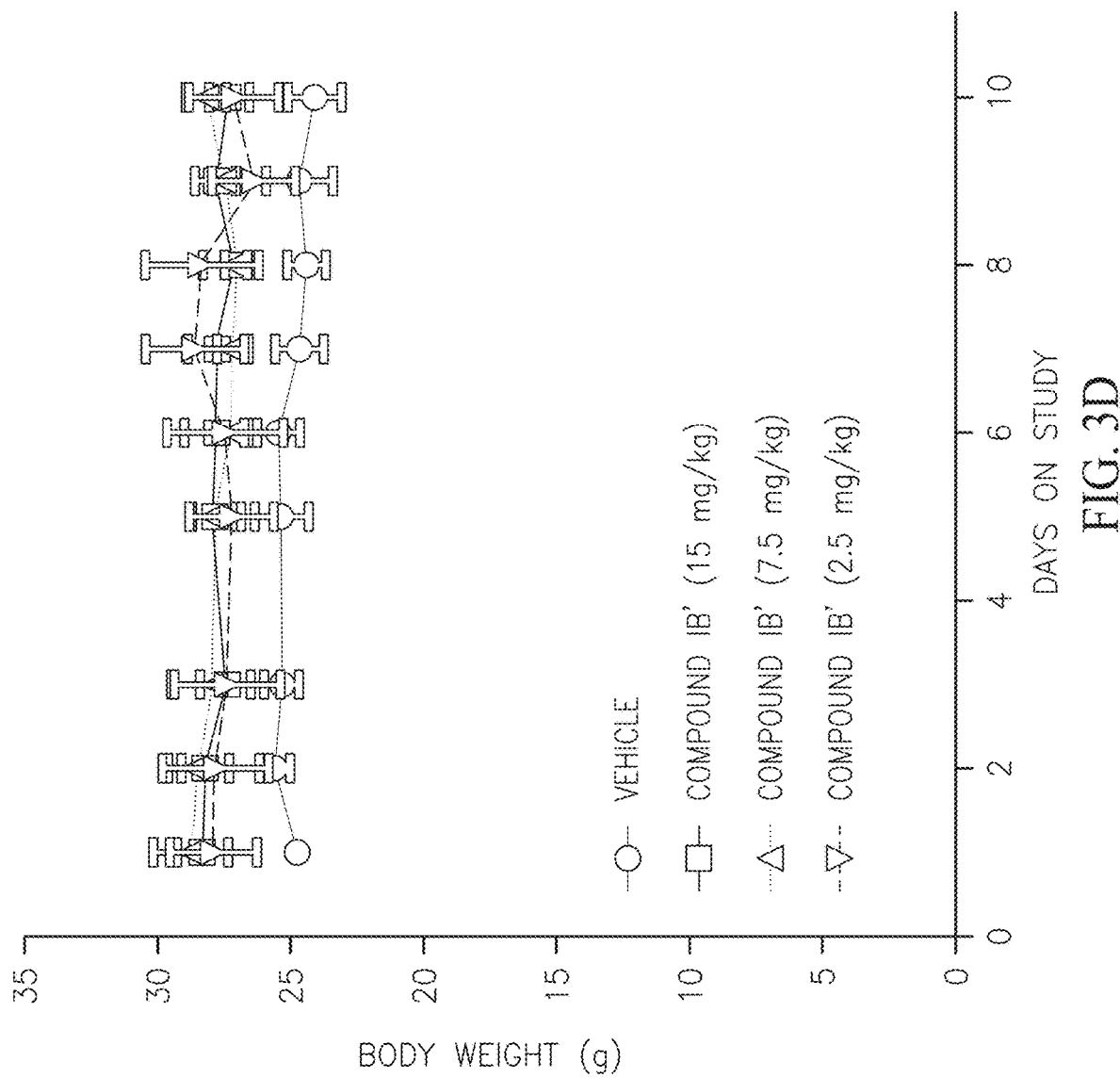

Repeat dose toxicology studies were performed in female SHO SCID mice using 3 animals per treatment group. Animals were treated with five daily doses of compound IB' at 15, 7.5, or 2.5 mg/kg, and were observed for five additional days following the dosing regimen. For comparison, additional animals were treated with alvocidib at the same dose levels and the same dosing/observation schedule. Body weight measurements of animals treated by oral (see FIGS. 3A-B) and intravenous (see FIG. 3C-D) dosing over the course of the 5-day repeat dosing period and subsequent 5-day observation period, along with mortality and clinical observations, were used to determine the maximum tolerated dosing schedule ($MTD_{repeat}$).

The results from the 5-day repeat-dose study determined that the $MTD_{repeat}$ of compound IB, dosed orally, is 7.5 mg/kg. The $MTD_{repeat}$ of compound IB', dosed intravenously, is 15 mg/kg. Body weight loss was observed in animals dosed orally at 15 mg/kg. In animals dosed orally at 15 mg/kg, one animal died on day 5, and one animal died on day 7.

For comparison, the $MTD_{repeat}$ determined for alvocidib, when dosed orally, was 7.5 mg/kg. The $MTD_{repeat}$ determined for alvocidib, when dosed intravenously, was 7.5 mg/kg. Lethargy, body weight loss, and deaths were observed at the 15 mg/kg dosing levels for both oral and intravenous dosing with alvocidib.

Body weight loss was observed in surviving animals at the 15 mg/kg oral dosing level with compound IB', which peaked at 12%. No overt toxicity was observed in animals dosed orally at 7.5 mg/kg or 2.5 mg/kg, or in animals dosed at any dose level attempted when administered intravenously.

Compound IB' is better tolerated ($MTD_{repeat}$=15 mg/kg) in mice when dosed intravenously compared to alvocidib ($MTD_{repeat}$=7.5 mg/kg).

Example 8

Maximum Tolerated Acute Dose in Rats

Acute (i.e. single dose) toxicology studies were performed in rats. Acute studies were performed in female Sprague Dawley rats using three animals per treatment group. Animals were treated with a single dose of compound IB' at 36, 18, 9, or 4.5 mg/kg. For comparison, additional animals were dosed with 18, 9, or 4.5 mg/kg alvocidib. Body weight measurements following oral dosing (see FIG. 4A), along with mortality, clinical observations, food consumption (see FIG. 4B), and complete blood counts (CBCs; see Table 12) were used to determine the maximum tolerated acute dose ($MTD_{acute}$).

The results from the acute study determined that the $MTD_{acute}$ of compound IB' in rats is 18 mg/kg. Diarrhea, body weight loss and increased lethargy were observed in animals dosed with compound IB at 36 mg/kg. At this dose level, one animal died on day three, one animal died on day four, and one animal died on day 5. Deaths were not observed in any other treatment group.

Figure 4A:
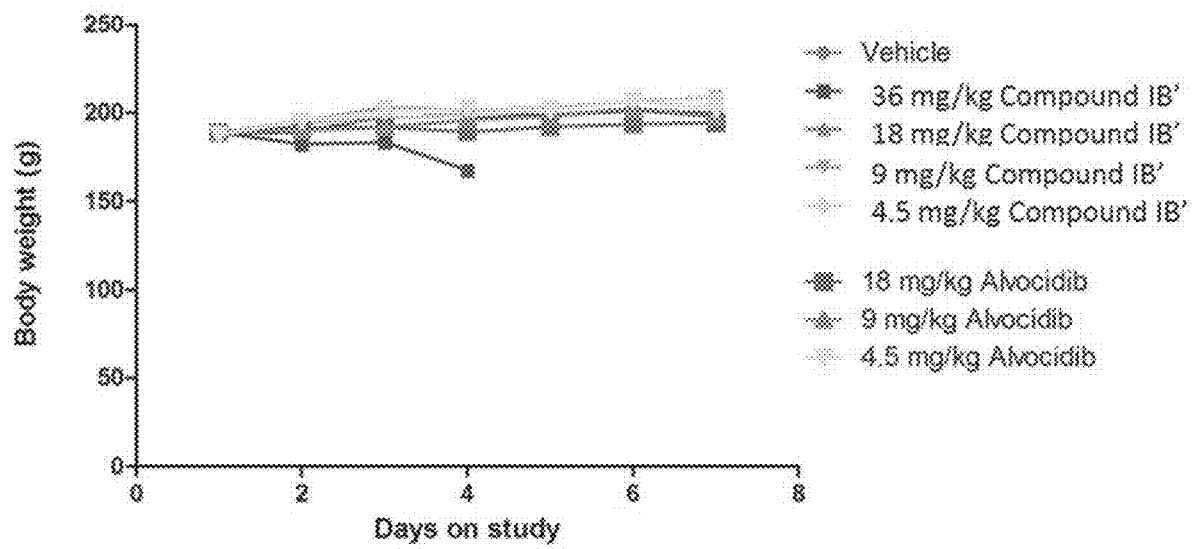
FIG. 4A-B show body weights and food consumption of rats treated with a single dose (orally) of alvocidib or compound IB.
Figure 4B:
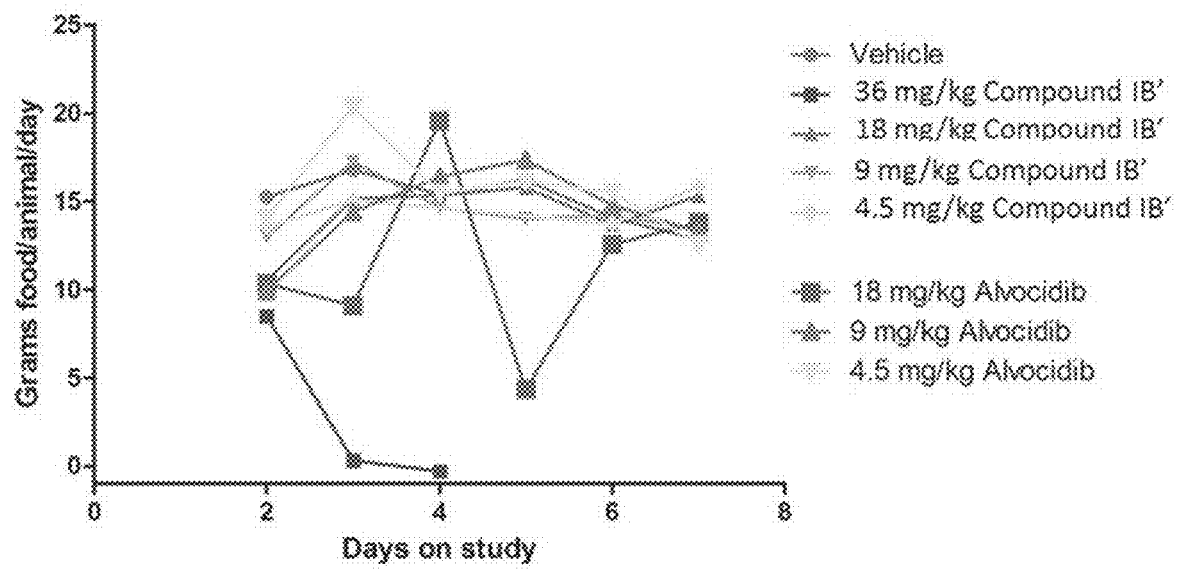

Body weight loss was observed in treated animals, preceding death, reaching 13.1% in animals treated at the 36 mg/kg dose level with compound IB' (see FIG. 4A). This body weight loss was accompanied by significant diarrhea, and increased lethargy in these animals. No overt toxicity, including body weight change or diarrhea, was observed in rats dosed at 18, 9, or 4.5 mg/kg with compound IB'. In comparison, animals dosed with 18 mg/kg alvocidib did show signs of diarrhea. In addition, abnormal food consumption patterns were observed with 18 mg/kg dosing of alvocidib that were not observed with the compound IB' treated animals at the same dosage level.

Abnormal CBCs were observed in some animals (Table 12). Specifically, platelet counts were outside the normal range for the vehicle and 9 mg/kg dosage of compound IB', and 4.5 mg/kg alvocidib dose. No consistent dose-dependent trend was observed in the surviving, treated animals. Slightly reduced red and white blood cell counts were observed at the 18 mg/kg dose level for compound IB'. However, slightly elevated counts were also observed in some untreated animals as well. The high variability of these results was attributed to inter-animal variation, and not drug-dependent mechanisms. As animals treated with 36 mg/kg of compound IB' expired overnight, CBCs were not available.

Based on the data above, the rat oral $MTD_{acute}$ of compound IB' was found to distinguish its tolerability profile versus that of alvocidib as the no observable adverse effect level (NOAEL) was found to be 18 mg/kg for compound IB' and 9 mg/kg for alvocidib.

TABLE 12

Blood Counts of Rats Treated With a Single Dose of Compound IB

| | RBC ($10^6/\mu L$) | MCV (fL) | HCT (%) | MCH (pg) | MCHC (g/dL) | RDWA (fL) | PLT ($10^3/\mu L$) | HGB (g/dL) | WBC ($10^3/\mu L$) |
|---|---|---|---|---|---|---|---|---|---|
| Vehicle | 7.8 | 53.1 | 41.5 | 19.5 | 36.8 | 15.7 | 34.3 | 174.3 | 15.2 |
| 36 mg/kg compound IB' | — | — | — | — | — | — | — | — | — |
| 18 mg/kg compound IB' | 5.9 | 53.5 | 31.2 | 19.6 | 36.6 | 15.7 | 33.9 | 201.3 | 11.4 |
| 9 mg/kg compound IB' | 8.0 | 53.3 | 42.7 | 19.5 | 36.6 | 15.9 | 35.0 | 112.7 | 15.6 |
| 4.5 mg/kg compound IB' | 9.1 | 54.8 | 49.9 | 19.7 | 35.9 | 16.2 | 37.1 | 319.3 | 17.9 |
| 18 mg/kg alvocidib | 8.8 | 53.8 | 47.3 | 19.3 | 35.9 | 16.1 | 36.1 | 376.0 | 16.9 |
| 9 mg/kg alvocidib | 8.7 | 54.0 | 47.1 | 19.3 | 35.7 | 16.2 | 36.3 | 334.7 | 16.8 |
| 4.5 mg/kg alvocidib | 8.3 | 52.7 | 43.6 | 18.7 | 35.4 | 16.0 | 34.7 | 147.0 | 15.4 |

Example 9

Mouse Xenograft Efficacy Study

Figure 5A:
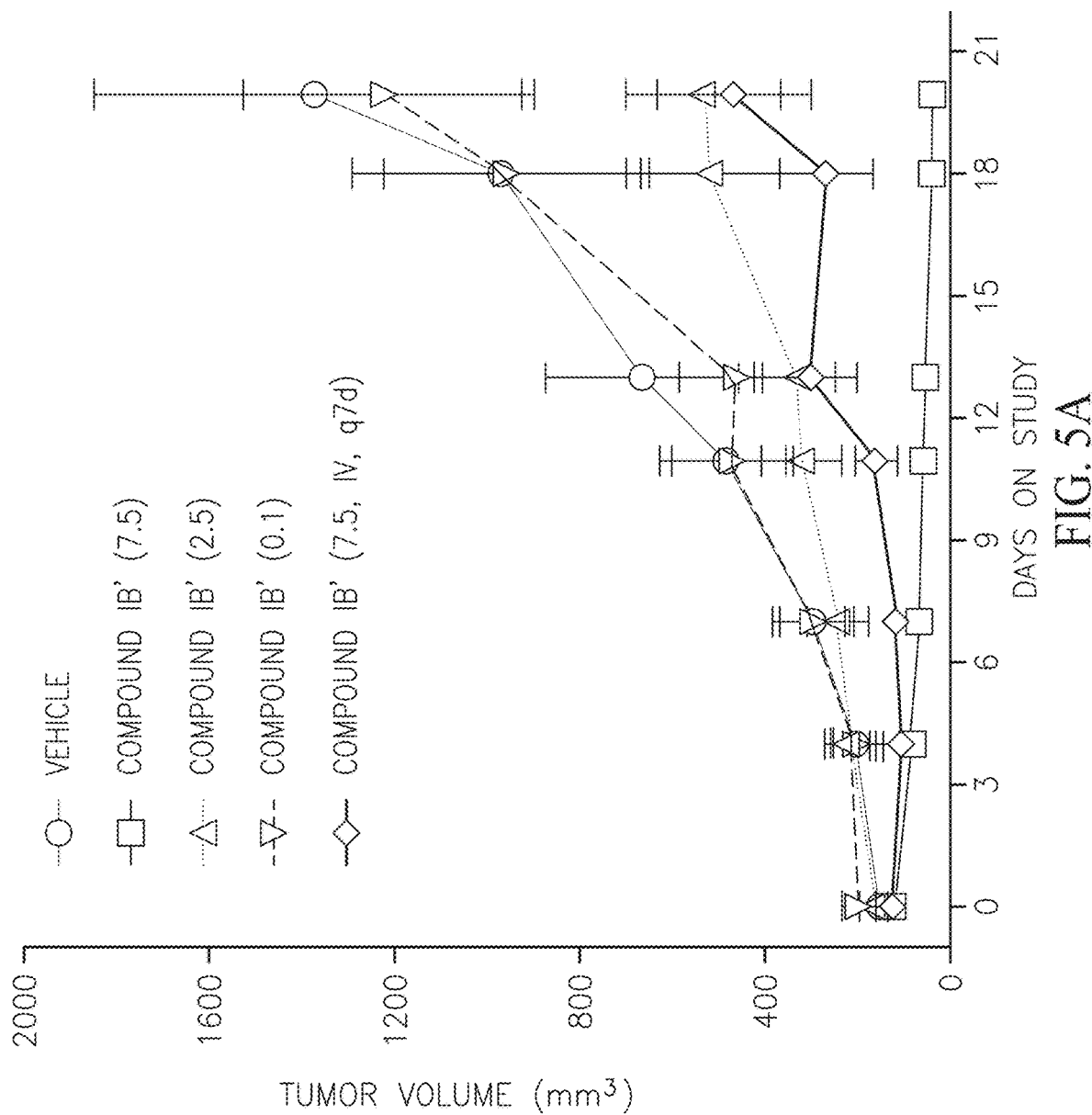
FIG. 5A-B show in vivo tumor volume and body weight after dosing with compound IB during a xenograft efficacy study.
Figure 5B:
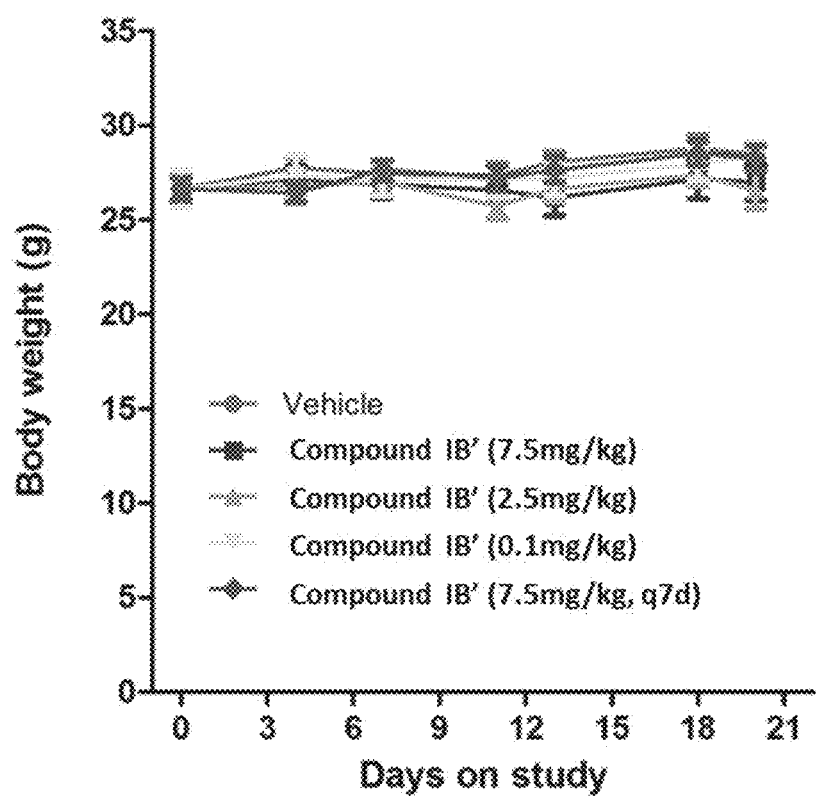

The in vivo activity of compound IB' was determined in a MV4-11 mouse xenograft model of acute myeloid leukemia (AML). Injection of $8\times10^6$ MV4-11 cells/mouse was followed by growth of tumors to approximately 100 mm³. After tumors reached the appropriate size, mice were randomized into the following treatment groups: Vehicle, compound IB' (7.5 mg/kg, qdx5x3), compound IB' (2.5 mg/kg, qdx5x3), compound IB' (0.1 mg/kg, qdx5x3) and compound IB (7.5 mg/kg, q7dx3). Vehicle and compound IB' were administered orally, except in the last arm of compound IB' (7.5 mg/kg, q7dx3), which was dosed intravenously. Treatment resulted in significant tumor growth inhibition (% TGI; see FIGS. 5A-B and Table 13).

TABLE 13

Tumor Growth Inhibition for Mouse Xenograft Efficacy Study

| Dosage of Compound IB' | Tumor Growth Inhibition (%) |
|---|---|
| Vehicle (i.e. no compound IB') | 0 |
| 7.5 mg/kg | 69 |
| 2.5 mg/kg | 12 |
| 7.5 mg/kg, q7dx3 | 74 |

Example 10

Mouse Xenograft Pharmacodynamic Study

Figure 6A:
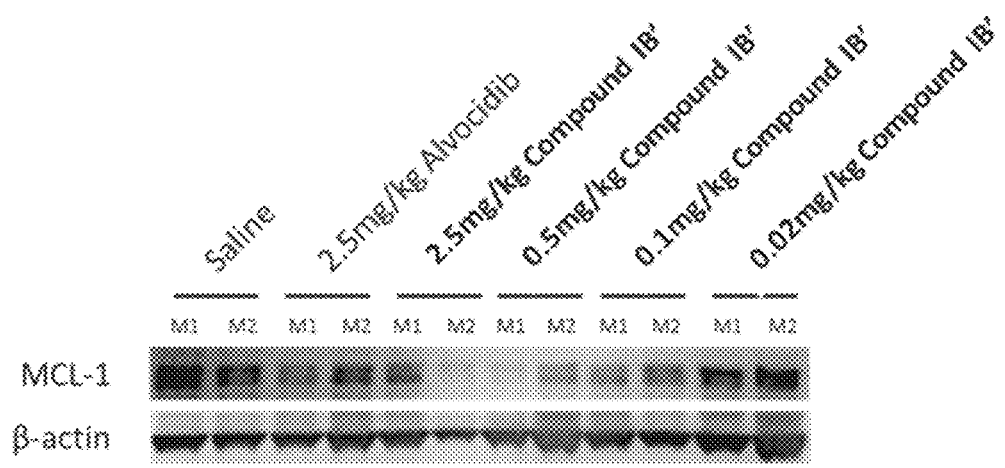
FIG. 6A-B depict reduction of MCL-1 protein expression following treatment with compound IB during a xenograft pharmacodynamic study.
Figure 6B:
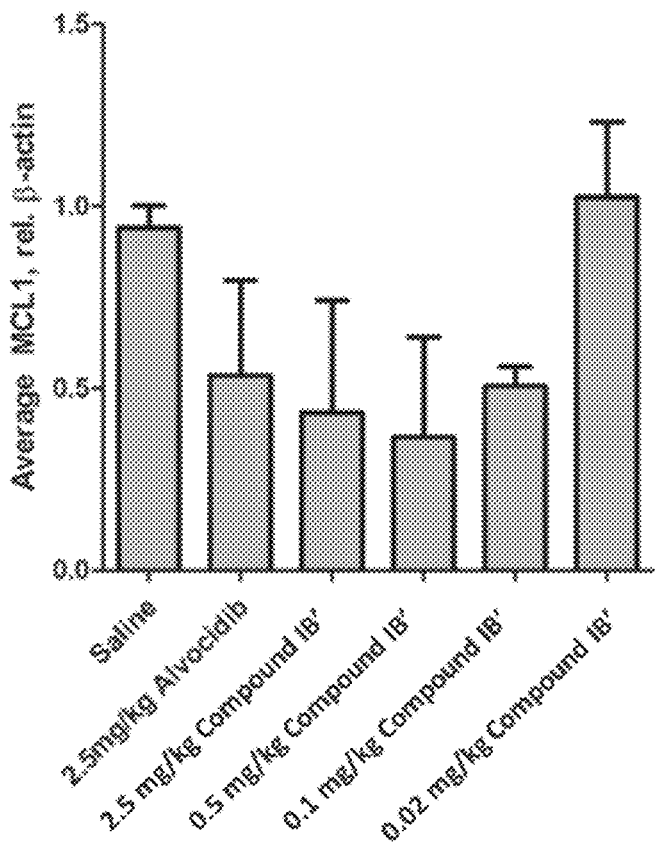

The in vivo pharmacodynamic activity of compound IB' was determined in a MV4-11 mouse xenograft model of AML (FIG. 6A-B). Injection of $8\times10^6$ cells/mouse was followed by growth of tumors to approximately 100 mm³. After tumors reached an appropriate size, mice were randomized into the following treatment groups: Vehicle, compound IB' (2.5 mg/kg), compound IB' (0.5 mg/kg), compound IB' (0.1 mg/kg), compound IB' (0.02 mg/kg). Mice were administered a single treatment dose and tumors were harvested 48 hours post-treatment. MCL-1 protein levels were assessed on harvested tumors using standard polyacrylamide gel electrophoresis and immunoblotting technique (FIG. 6A). Treatment resulted in reduction of MCL-1 protein expression (see FIG. 6B and Table 14 below).

TABLE 14

Reduction of MCL-1 Protein Expression

| Dosage of Compound IB' | Reduction of MCL-1 Expression (%) |
|---|---|
| Vehicle (i.e. no compound IB') | 0.0 |
| 2.5 mg/kg | 54 |
| 0.5 mg/kg | 61 |
| 0.1 mg/kg | 46 |
| 0.02 mg/kg | 0.0 |

All of the U.S. patents, U.S. patent application publications, U.S. patent applications, foreign patents, foreign patent applications and non-patent publications referred to in this specification, including U.S. Provisional Patent Application Ser. No. 62/163,188, filed May 18, 2015, are incorporated herein by reference, in their entirety to the extent not inconsistent with the present description.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for preparing a compound of structure (I):

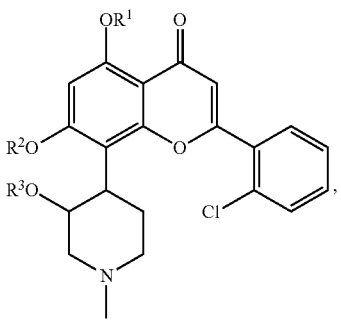

(I)

or a stereoisomer, tautomer or pharmaceutically acceptable salt thereof, wherein:

one of $R^1$, $R^2$ or $R^3$ is —P(=O)(OH)$_2$, and the other two of $R^1$, $R^2$ and $R^3$ are each H, the method comprising adding a phosphate group to one of three free hydroxyls of alvocidib, or a salt or solvate thereof.

2. The method of claim 1, wherein the compound has the following structure (I'):

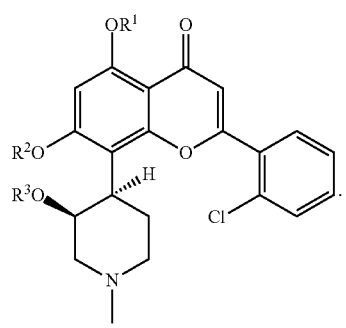

(I')

3. The method of claim 1, wherein the compound has the following structure (IA):

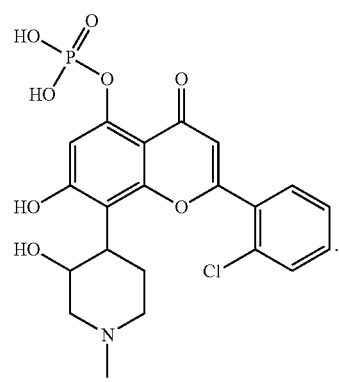

(IA)

4. The method of claim 3, wherein the compound has the following structure (IA'):

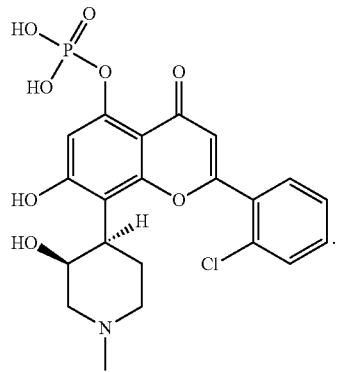

(IA')

5. The method of claim 1, wherein the compound has the following structure (IB):

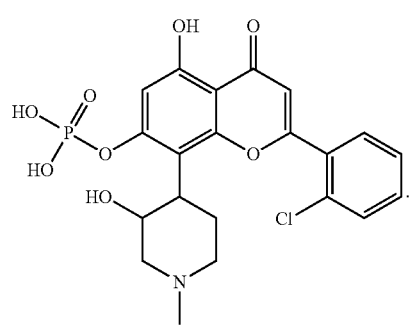

(IB)

6. The method of claim 5, wherein the compound has the following structure (IB'):

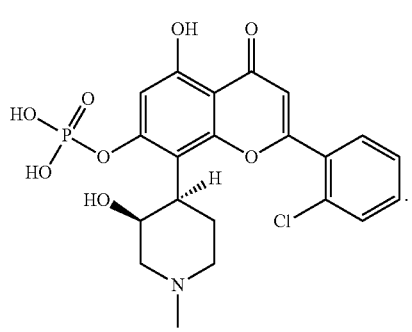
(IB')

7. The method of claim 1, wherein the compound has the following structure (IC):

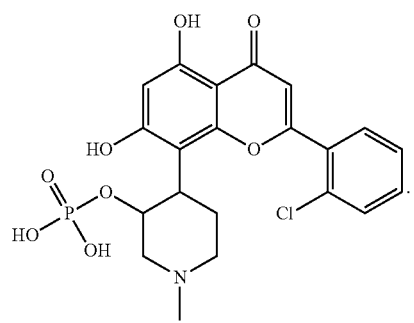
(IC)

8. The method of claim 7, wherein the compound has the following structure (IC'):

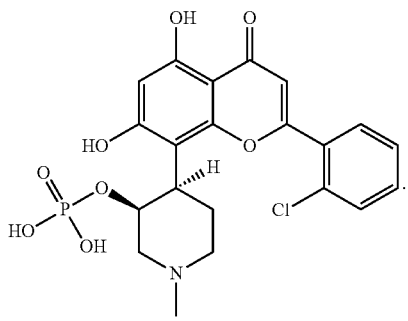
(IC')

9. The method of claim 1, further comprising treating the compound of structure (I) with an inorganic or organic base or acid to convert the compound of structure (I) to a pharmaceutically acceptable salt of the compound of structure (I).

10. The method of claim 1, further comprising converting a salt of the compound of structure (I) to its free base or acid form.

* * * * *